(12) United States Patent
Rajagopalan

(10) Patent No.: US 9,186,349 B2
(45) Date of Patent: Nov. 17, 2015

(54) DIAZA HETEROCYCLIC COMPOUNDS FOR PHOTOTHERAPY

(75) Inventor: Raghavan Rajagopalan, St. Peters, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 24 days.

(21) Appl. No.: 13/319,771

(22) PCT Filed: May 12, 2010

(86) PCT No.: PCT/US2010/034523
§ 371 (c)(1),
(2), (4) Date: Nov. 10, 2011

(87) PCT Pub. No.: WO2010/132554
PCT Pub. Date: Nov. 18, 2010

(65) Prior Publication Data
US 2012/0058954 A1 Mar. 8, 2012

Related U.S. Application Data

(60) Provisional application No. 61/177,334, filed on May 12, 2009.

(51) Int. Cl.
| A61K 31/495 | (2006.01) |
| A61N 5/06 | (2006.01) |
| A61K 31/397 | (2006.01) |
| A61K 31/415 | (2006.01) |
| A61K 31/502 | (2006.01) |
| A61K 31/5025 | (2006.01) |

(52) U.S. Cl.
CPC ............. *A61K 31/397* (2013.01); *A61K 31/415* (2013.01); *A61K 31/495* (2013.01); *A61K 31/502* (2013.01); *A61K 31/5025* (2013.01); *A61N 5/062* (2013.01)

(58) Field of Classification Search
None
See application file for complete search history.

(56) References Cited

U.S. PATENT DOCUMENTS

| 3,129,215 | A | 4/1964 | Horvitz |
| 5,409,900 | A | 4/1995 | Vogel et al. |
| 5,672,333 | A | 9/1997 | Rajagopalan et al. |
| 5,698,397 | A | 12/1997 | Zarling et al. |
| 5,714,342 | A | 2/1998 | Komoriya et al. |
| 6,167,297 | A | 12/2000 | Benaron |
| 6,228,344 | B1 | 5/2001 | Dorshow et al. |
| 6,258,378 | B1 | 7/2001 | Schneider et al. |
| 6,376,483 | B1 | 4/2002 | Robinson |
| 6,406,713 | B1 | 6/2002 | Janoff et al. |
| 6,468,995 | B1 | 10/2002 | Kawabata et al. |
| 6,485,704 | B1 | 11/2002 | Rajagopalan et al. |
| 6,747,151 | B2 | 6/2004 | Rajagopalan et al. |
| 6,748,259 | B1 | 6/2004 | Benaron et al. |
| 6,761,878 | B2 | 7/2004 | Achilefu et al. |
| 6,838,074 | B2 | 1/2005 | Carpenter, Jr. |
| 6,861,416 | B2 | 3/2005 | Wolfe et al. |
| 6,987,079 | B2 | 1/2006 | Wormsbecher |
| 7,011,817 | B2 | 3/2006 | Achilefu et al. |
| 7,030,110 | B2 | 4/2006 | Wang et al. |
| 7,128,896 | B2 | 10/2006 | Achilefu et al. |
| 7,198,778 | B2 | 4/2007 | Achilefu et al. |
| 7,201,892 | B2 | 4/2007 | Achilefu et al. |
| 7,230,088 | B2 | 6/2007 | Rajagopalan et al. |
| 7,235,685 | B2 | 6/2007 | Rajagopalan et al. |
| 7,252,815 | B2 | 8/2007 | Achilefu et al. |
| 7,303,926 | B2 | 12/2007 | Rajagopalan et al. |
| 7,351,807 | B2 | 4/2008 | Rajagopalan et al. |
| 7,375,119 | B2 * | 5/2008 | Kawaguchi et al. .......... 514/340 |
| 7,427,657 | B1 | 9/2008 | Rajagopalan et al. |
| 7,431,925 | B2 | 10/2008 | Rajagopalan et al. |
| 7,504,087 | B2 | 3/2009 | Achilefu et al. |
| 7,510,700 | B2 | 3/2009 | Achilefu et al. |
| 7,758,861 | B2 | 7/2010 | Rajagopalan et al. |
| 7,767,194 | B2 | 8/2010 | Achilefu et al. |
| 7,790,144 | B2 | 9/2010 | Achilefu et al. |
| 7,888,378 | B2 | 2/2011 | Rajagopalan et al. |
| 2002/0164287 | A1 | 11/2002 | Rajagopalan et al. |
| 2002/0169107 | A1 | 11/2002 | Rajagopalan et al. |
| 2003/0017164 | A1 | 1/2003 | Rajagopalan et al. |

(Continued)

FOREIGN PATENT DOCUMENTS

| RU | 2 223 274 | 2/2004 |
| WO | WO 90/08529 | 8/1990 |

(Continued)

OTHER PUBLICATIONS

Alder, K. et al. (Feb. 1954). Annalen Der Chemie, 585, 81.
Allinger, N.L. et al (1962), "Aromatic and Pseudoaromatic Non-benzenoid Systems. III. The Synthesis of some Ten p-Electron Systems," J. Am. Chem. Soc., 84, 1020-1026.
Barenholz, Y. (Aug. 26, 1992) "Liposome Production: Historic Aspects," In; Braun-Falco et al., (Eds.), Griesbach Conference, Liposome Dermatics, Springer-Verlag, Berlin, pp. 69-81.
Brede, O. et al. (2005), "Ionization of Cyclic Aromatic Amines by Free Electron Transfer: Products Are Governed by Molecule Flexibility," J. Phys. Chem., 109, 8081-8087-9672.
Breslow, R. et al. (1981), "Selective Functionalization of Doubly Coordinated Flexible Chains," J. Am. Chem. Soc., 103, 2905-2907.
Calberg-Bacq et al. (Jul. 1968), "Inactivation and mutagenesis due to the photodynamic action of acridines and related dyes on extracellular bacteriophage T4B," Mutation Research, vol. 6, No. 1, pp. 15-24.

(Continued)

*Primary Examiner* — Karlheinz R Skowronek
*Assistant Examiner* — Joseph Fischer

(57) ABSTRACT

The invention relates generally to optical agents, including phototherapeutic agents, for biomedical applications, including phototherapy. The invention includes optical agents, and related therapeutic methods, comprising alicyclic diaza compounds, including 1,2 diaza heterocyclic compounds, having a photolabile N—N bond directly or indirectly linked to at least one carbocyclic aromatic and/or heterocyclic aromatic group. In some embodiments, for example, the invention provides alicyclic diaza compounds for phototherapeutic methods having a photolabile N—N bond that undergoes photoactivated cleavage to produce reactive species, such as radicals, ions, etc., that achieve a desired therapeutic effect, such as selective and/or localized tissue damage and/or cell death.

7 Claims, 11 Drawing Sheets

(56) References Cited

U.S. PATENT DOCUMENTS

| | | | |
|---|---|---|---|
| 2003/0031627 A1 | 2/2003 | Rajagopalan et al. | |
| 2003/0036538 A1 | 2/2003 | Rajagopalan et al. | |
| 2003/0072763 A1 | 4/2003 | Rajagopalan et al. | |
| 2003/0105299 A1 | 6/2003 | Achilefu et al. | |
| 2003/0105300 A1 | 6/2003 | Achilefu et al. | |
| 2003/0152577 A1 | 8/2003 | Achilefu et al. | |
| 2003/0158127 A1 | 8/2003 | Rajagopalan et al. | |
| 2003/0185756 A1 | 10/2003 | Achilefu et al. | |
| 2004/0151667 A1 | 8/2004 | Rajagopalan et al. | |
| 2004/0156783 A1* | 8/2004 | Rajagopalan et al. | 424/9.6 |
| 2004/0161430 A1 | 8/2004 | Rajagopalan et al. | |
| 2004/0180864 A1 | 9/2004 | Rajagopalan et al. | |
| 2004/0234454 A1 | 11/2004 | Achilefu et al. | |
| 2004/0241095 A1 | 12/2004 | Achilefu et al. | |
| 2004/0253182 A1 | 12/2004 | Achilefu et al. | |
| 2005/0031542 A1 | 2/2005 | Achilefu et al. | |
| 2005/0271592 A1 | 12/2005 | Achilefu et al. | |
| 2005/0281741 A1 | 12/2005 | Achilefu et al. | |
| 2006/0020004 A1 | 1/2006 | Christensen et al. | |
| 2006/0177457 A1 | 8/2006 | Rajagopalan et al. | |
| 2006/0247210 A1 | 11/2006 | Zhang et al. | |
| 2007/0128115 A1 | 6/2007 | Achilefu et al. | |
| 2008/0139786 A1 | 6/2008 | Rajagopalan et al. | |
| 2008/0233050 A1 | 9/2008 | Achilefu et al. | |
| 2008/0275017 A1 | 11/2008 | Rajagopalan et al. | |
| 2009/0016965 A1 | 1/2009 | Rajagopalan et al. | |
| 2009/0035363 A1 | 2/2009 | Rajagopalan et al. | |
| 2009/0036502 A1 | 2/2009 | Rajagopalan et al. | |
| 2009/0304583 A1 | 12/2009 | Achilefu et al. | |
| 2010/0022449 A1 | 1/2010 | Achilefu et al. | |
| 2010/0105899 A1 | 4/2010 | Neumann et al. | |
| 2010/0222547 A1 | 9/2010 | Rajagopalan et al. | |
| 2010/0233091 A1 | 9/2010 | Neumann et al. | |
| 2010/0311903 A1 | 12/2010 | Rajagopalan et al. | |
| 2011/0130707 A1 | 6/2011 | Rajagopalan et al. | |
| 2011/0177006 A1 | 7/2011 | Rajagopalan et al. | |
| 2011/0177007 A1 | 7/2011 | Rajagopalan et al. | |
| 2011/0196231 A1 | 8/2011 | Rajagopalan et al. | |
| 2011/0257583 A2 | 10/2011 | Rajagopalan et al. | |
| 2011/0264026 A1 | 10/2011 | Rajagopalan | |
| 2011/0288033 A1 | 11/2011 | Rajagopalan | |
| 2012/0053511 A1 | 3/2012 | Rajagopalan | |

FOREIGN PATENT DOCUMENTS

| | | | |
|---|---|---|---|
| WO | WO 02/076177 | 10/2002 | |
| WO | WO 2004/035536 | 4/2004 | |
| WO | WO 2004/093803 | 11/2004 | |
| WO | WO 2004093803 A2 * | 11/2004 | A61K 31/41 |
| WO | WO 2005/037928 | 4/2005 | |
| WO | WO 2005/089813 | 9/2005 | |
| WO | WO 2006/017214 | 2/2006 | |
| WO | WO 2006/111971 | 10/2006 | |
| WO | WO 2007/106436 | 9/2007 | |
| WO | WO 2007/149478 | 12/2007 | |
| WO | WO 2008/108941 | 9/2008 | |
| WO | WO 2008/128538 | 10/2008 | |
| WO | WO 2010/037067 | 4/2010 | |
| WO | WO 2010/037068 | 4/2010 | |
| WO | WO 2010/132525 | 11/2010 | |
| WO | WO 2010/132547 | 11/2010 | |

OTHER PUBLICATIONS

Cann, M. C. (1988), "Formation of Acridine from the reaction of Dibenz[b,f]azepine with Silver(I): Formation of an Aromatic Nitrenium Ion?" J. Org. Chem. 53, 1112-1113.

Charbit, J. J. et al. (1989), "Preparation of Some New N-Substituted 9,10-Dihydroacridine Derivatives," J. Chem. Eng. Data, 34, 136-137.

Eyer, P. (1983), "The Red Cell as a Sensitive Target for Activated Toxic Arylamines," Archives of Toxicology, Supplement, 6, 3-12.

Gilbert, B. C. et al. (1970) "Electron Spin Resonance of Some Heterocyclic Radicals Containing Elements of Group VI," J. Chem. Soc. [Section. B]: Physical Organic, 9, 1700-1708.

Harada, A. (1990), "Cytotoxicity of Aniline Derivatives," Igakkai Zasshi, 99, 233-247.

Hassner, A. (Ed.) (1983) Small ring heterocycles: Azetidines, b-lactams, diazetidines, diaziridines. Heterocyclic Compounds John Wiley & Sons: New York, vol. 42.

Hopff, H. et al. (1963), "2-Vinylthianthrene and Its Polymerization Products," Makromolekulare Chemie, 60, 129-138.

Huang , A. (2005), "A Review of progress in Clinical Photodynamic Therapy," Technol. Cancer Res. Treat., 4, 283-293.

Janzen, E.G. (1973), "Radical Addition Reactions of 5,5-Dimethyl-I-pyrroline-I-oxide. ESR Spin Trapping with a Cyclic Nitrone," J. Mag. Res. 9, 510-512.

Karwa et al. (Sep. 13, 2011), "Type 1 Phototherapeutic Agents, Part I. Preparation and Cancer Cell Viability Studies of Novel Photolabile Sufenamides," ACS. Med. Chem. Lett., 2, 828-833.

Kriftner, R.W. (Aug. 26, 1992) "Liposome Priduction: The Ethanol Injuection Technique and the Devel;opment of the First Approved Liposome Dermatic," In; Braun-Falco et al., (Eds.), Griesbach Conference, Liposome Dermatics, Springer-Verlag, Berlin, pp. 91-100.

Lin, T.-S. et al. (1986), "ESR Studies of Photochemical Reactions of Diphenylamines, Phenothiazines and Phenoxazines," J. Phys. Chem. B, 90, 2687-2689.

Marshall (1979), "Solid Oral Dosage Forms," In; *Modern Pharmaceutics* (Banker and Rhodes, Eds.), 7:359-427.

Martin, M. et al. (1980), "Two-Photon Stepwise Dissociation of Carbazole in Solution," J. Phys. Chem. 84, 70-72.

Migita, C.T. et al. (2003), "Spin Trapping of the Nitrogen Radicals," Chem. Lett., 32 466-467.

Moor, A. C. E. et al. (2003), Mechanisms of Photodynamic Therapy. In Photodynamic Therapy, Patrice, T., (Ed.), RSC: Cambridge; pp. 19-57.

Moderhack, D. (May/Jun. 1993) Oxo- and imino-functionalized 1,2-oxazetidines: An Overview. Journal of Heterocyclic Chemistry, 30(3), 579-591.

Nogrady (1985), Medicinal Chemistry A Biochemical Approach, Oxford University Press, pp. 388-392, New York, NY.

Nyst, H. J. et al. (Mar. 2009), "Is Photodynamic Therapy a Good Alternative to Surgery and Radiotherapy in the Treatment of Head and Neck Cancer?" Photodiag. Photodyn Ther., 6, 3-11.

O'Connor, A. E. et al. (2009), "Porphyrin and Non-porphyrin Photosensitizes in Oncology: Preclinical and Clinical Advances in Photodynamic Therapy," Photochem. Photobiol., 85, 1053-1074.

Padwa, A. (1984) Intramolecular 1,3-dipolar cycloadditions. In 1,3-Dipolar Cycloaddition Chemistry, vol. 2, pp. 277-378. Padwa, A. (Ed.)., Wiley Interscience, New York, NY.

Patch, J.A. et al. (2004), "Versatile oligo(N-substituted)glycines: The many roles of peptoids in drug discovery," Pseudo-Peptides in Drug Discovery, Nielsen, P.E. (Ed.), Wiley-VCH, pp. 1-31, Weinheim.

Pinto-Basto, et al. (2009), "Antioxidant Activity of Synthetic Diarylamiines: A Mitochondrial and Cellular Approach," Mitochondrion, 9, 17-26.

Rahmanto, A. S. et al. (Nov. 30, 2010), Cellular Effects of Photogenerated Oxidants and Long-Lived, Reactive, Hydroperoxide Photoproducts, Free Radic. Biol. & Med., 49, 1505-1515.

Rahn, R. et al. (1989), "Intensity-Dependent Ultraviolet Laser Flash Excitation of Diphenylamine in Methanol: A Two-Photon Ionization Mechansim Involving the Triplet State," J. Phys. Chem., 93, 7841-7856.

Rajagopalan et al. (Feb. 16, 2012), "Type 1 Phototherapeutic Agents. 2. Cancer Cell Viability and ESR Studies of Tricyclic Diarylamines," ACS Med. Chem. Lett., 3 (4), pp. 284-288.

Röding, J. (Aug. 26, 1992) "Properties and Characterization of Pre-Liposome Systems," In; Braun-Falco et al., (Eds.), Griesbach Conference, Liposome Dermatics, Springer-Verlag, Berlin, pp. 110-117.

Schwan, A.L.; Warkentin, J. (1996) Four-membered ring with one oxygen and one nitrogen atom. Comprehensive Heterocyclic Chemistry II, 1B, 969-1007.

Shukla, D., et al. (1991), "Laser Flash Photolysis and Product Studies of the Photoionization of N-Methylacridan in aqueous solution," J. Phys. Chem., 95, 10240-10246.

Viola, G. et al. (2000), "In Vitro Studies of the Phototoxic Potential of the antidepressant drug amitriptyline and imipramine," Farmaco, 55, 211-218.

(56) References Cited

OTHER PUBLICATIONS

Wang, Z., et al. (1993) "One- and Two-Laser Photochemistry of Iminodibenzyl," J. Phys. Chem., 97, 9668-9672.
Wardman, P. et al. (1995), Radicals from One-electron Reduction of Nitro Compounds, Aromatic N-Oxides, and Quinones: The Kinetic Basis for Hypoxia-Selective, Bioreductive Drugs. In Free Radicals and Oxidative Stress: Environment, Drugs, and Food Additives. Rice-Evans, C., et al. (Eds.), Portland Press, pp. 171-194, London.
Weder, H.G. (Aug. 26, 1992) "Liposome Production: The Sizing-Up Technology Starting from Mixed Micelles and the Scaling-Up Procedure for the Topical Glucocorticoid Beta-methasone Dipropionate and Betamethasone," In; Braun-Falco et al., (Eds.), Griesbach Conference, Liposome Dermatics, Springer-Verlag, Berlin, pp. 101-109.
Wu, et al. (Oct. 2008), Peptidomimetics, Accounts of Chemical Research, vol. 41, No. 10, 1231-1232.
Xu, H.J. et al. (1989), "Radical Mechanism in the Photoinduced Oxygen Transfer from Acridine N-Oxide to Cyclohexene," J. Photochem. Photobiol., A: Chemistry, 48, 53-59.
Abu, Shady H. et al. (Jan. 1988), "Synthesis, Cytotoxic and Antimicrobial Activities of Some 9-Anilino Acridines and 9-(P-Arylidene Hydrazino) Acridines," Egyptian Journal of Pharmaceutical Sciences, vol. 29, No. 1-04, pp. 577-586.
Achilefu, S.A. et al. (Aug. 2000), Novel receptor-targeted fluorescent contrast agents for in vivo imaging of tumors, Investigative Radiology, 35(8), pp. 479-485.
Avaline, B.M. et al. (Sep. 1998), "Exclusive free radical mechanisms of cellular photosensitization," Photochemistry and Photobiology, vol. 68, No. 3, pp. 266-275.
Ballou et al. (Oct. 1995), Tumor labeling in vivo using cyanine conjugated monoclonal antibodies, Cancer Immunology and Immunotherapy, 41, pp. 257-263.
Barlin et al. (1979), "Tautomerism in N-Heterocycles. IV Pyrazino[2,3-d]pyridazine-5,8-diol," Aust. J. Chem., 32, 459-62.
Bassoli, A. et al. (1988), the heterolytic and homolytic cleavage of the oxygen-nitrogen bond in O,N-diacylhydroxylamines. Bulletin de la Societe Chimique de France, 2, 293-297.
Belinier, D.A. et al. (Sep. 1993), Murine pharmacokinetics and antitumor efficacy of the photodynamic sensitizer 2-[I-hexyloxyethyl]-2-devinyl pyropheophorbide-a, J. Photochem. Photobiol., 20(1), pp. 55-61.
Benaron, D.A. et al. (Mar. 5, 1993), Optical time-of-flight and absorbance imaging of biologic media, Science, 259, pp. 1463-1466.
Brown, S. et al. (Aug. 2004), "Photodiagnosis and Photodynamic Therapy." The present and future role of photodynamic therapy in cancer treatment. Lancet Oncol., 5:497-508.
Chen, B. et al. (Feb. 1, 2006), Tumor vascular permeabilization by vascular-targeting photosensitization: effects, mechanism, and therapeutic implications. Clinical Cancer Research, 12(3, Pt.1), 917-923.
Cheves, W. et al. (Apr. 5, 1960), The decomposition of diacyl hydroxylamines and hydrazines. J. Am. Chem. Soc., 82, 1820-1825.
Clennan et al. (Jun. 1990), "Hydrazines New Charge-Transfer Physical Quenchers of Singlet Oxygen," Journal of the American Chemical Society, vol. 112, No. 13, pp. 5080-5085.
Davies et al. (Mar. 15, 1989), "Inhibition of Myeloperoxidase by Salicylhydroxamic Acid," Biochemical Journal, vol. 258, No. 3, pp. 801-806.
Diwu et al. (Jan. 1994), "Phototherapeutic potential of alternative photosensitizers to porphyrins," Pharmacology and Therapeutics, vol. 63, No. 1, pp. 1-35.
Dougherty, T.J. et al. (Jun. 17, 1998), Photodynamic Therapy. J. Natl. Cancer Inst.; 90:899-905.
Dufes et al. (Oct. 2000), "Niosomes and Polymeric Chitosan Based Vasicles Bearing Transferrin and Glucose Ligands for Drug Targeting," Pharm. Res. 17:1250.
Fantini, S. et al. (Apr. 1, 1998), Assessment of the size, position, and optical properties of breast tumors in vivo by noninvasive optical methods, Appl. Opt., 37, pp. 1982-1989.
Feofanov, Alexie et al. (Feb. 2004), "Comparative study of photodynamic properties of 13,15-N-cyclomide derivative of chlorin p6," Photochemistry and Photobiology, vol. 79, No. 2, pp. 172-188.
Gillis, B.T. (1967) Azo compounds as dienophiles. In 1,4-Cycloaddition Reactions: The Diels-Alder Reaction in Heterocyclic Syntheses, Hamer, J. (Ed.)., Academic Press, vol. 8, pp. 143-175, New York, NY.
Grosjean, P. et al. (Jun. 1998), Clinical phototherapy for superficial cancer in the esophagus and the bronchi: 514 nm compared with 630 nm light irradiation after sensitization with Photofrin II. British Journal of Cancer, 77, 1989-1955.
Hamer, J. (Ed.) (1967) 1,4-Cycloaddition Reactions Academic Press: New York, vol. 8.
Hnatowich et al. (May 6, 1983), Radioactive Labeling of Antibody. A simple and efficient method. Science, 220, 613-615.
Karmakova, T. et al. (Jan. 2, 2006), "Tissue distribution and in vivo photosensitizing activity of 13,15-[N[(3-hydroxypropyl)]cycloimide chlorin p6 and 13,15-(N-methoxy)cycloimide chlorin p6 methyl ester," Journal of Photochemistry and Photobiology, Vo. 82, No. 1, pp. 28-36.
Karwa et al. (Jan. 23, 2010), "In vitro biological effects of novel type 1 photosensitizers and their mechanism of action," Optical Methods for Tumor Treatment and Detection: Mechanisms and Techniques in Photodynamic Therapy XIX, Proc. of SPIE vol. 7551 75510S-/1-7.
Li, L. et al. (2006), Clinical study of photofrin phototherapy for the treatment of relapse nasopharyngeal carcinoma. Photodiagnostics and Phototherapy, 3, 266-271.
Licha et al. (Jul. 2, 1999), New contrast agent for optical imaging: acid cleavable conjugates of cyanine dyes with biomolecules, in Biomedical Imaging: Reporters, Dyes and Instrumentation, Proceedings of SPIE, 3600, pp. 29-35.
Liu et al. (Dec. 20, 2005), "Synthesis of novel isoxazole-fused chlorins and bacteriochlorins via 1,3-dipolar cycloaddition reactions of nitrile oxides with porphyrins," Synthesis 20051220 Georg Thieme Verlag De, No. 20, pp. 3632-3638.
MacKenzie, J.C.J. et al. (Dec. 1952), Diels-Alder additions with dialkylazodicarboxylates and azo-bis-formamidine. Journal of Organic Chemistry, 17, 1666-1674.
Mitton, D. et al. (2006), Phototherapy of Barrett's oesophagus and oesophageal carcinoma—how I do it. Photodiagnostics and Phototherapy, 3, 96-98.
Mlkvy, P. et al. (1998), Phototherapy for gastrointestinal tumors using three photosensitizers—ALA induced PPIX, Photofrin, and MTHPC. A pilot study. Neoplasma, 45, 157-161.
Möller, Marrianne et al. (Nov. 15, 2002), "Studies on cytotoxic and genotoxic effects of N-hydroxypyridine-2-thione (Omadine) in L5178Y mouse lymphoma cells," Toxicology Letters, vol. 136, No. 1, pp. 77-84.
Nairn, J.G. (1985), Remington's Pharmaceutical Science, pp. 1492-1517 (A. Gennaro, ed., Mack Publishing Co., Easton, Pa.).
Pelegrin, A. et al. (1992), Photoimmunodiagnosis with antibody-fluorescein conjugates: in vitro and in vivo preclinical studies, J. Cell Pharmacol., 3, pp. 141-145.
Priya et al. (Jan. 1, 2006), "Delta.2-Isoxazoline derivatives as antimicrobials," Heterocyclic Communications, Freund Publishing House, Tel Aviv, Vo. 12, No. 1, pp. 35-42.
Rajagopalan et al. (Jan. 1, 2001), "Targeted Type 1 phototherapeutic agents using azido-peptide bioconjugates," Biomarkers and Biological Spectral Imaging, Proc. of SPIE vol. 4259, 129-132.
Rajagopalan et al. (Jun. 11, 2009) "Novel type 1 photosensitizers: viability of leukemia cells exposed to reactive intermediates generated in situ by in vitro photofragmentation (Proceedings Paper)"; Proc. of SPIE, vol. 7380, pp. 738027/1-738027/8.
Rajagopalan et al. (Jan. 23, 2010) "Novel visible light activated type 1 photosensitizers (Proceeding Paper)"; Proc. of SPIE, vol. 7551, pp. 7551R/1-7751R/6.
Reynolds, J.S. et al. (Jul. 1999), Imaging of spontaneous canine mammary tumors using fluorescent contrast agents, Photochem. Photobiol., 70, pp. 87-94.
Roberts et al. (Oct. 1979), Radiosensitization of E. coli B/r by 9-anilinoacridines, British Journal of Cancer, vol. 40, No. 4, pp. 641-648.
Schmidt-Drfurth, U. et al. (Dec. 1996), Photodynamic therapy in ocular vascular disease. IEEE Journal of Selected Topics in Quantum Electronics, 2, 988-996.

(56) References Cited

OTHER PUBLICATIONS

Spiegel, A.J., et al. (Oct. 1963), "Use of Nonaqueous Solvents in Parenteral Products," J. Pharma. Sciences, vol. 52, No. 10, pp. 917-927.
Stermitz, F.R. et al. (Apr. 18, 1973), Diacylamino and diacyl nitroxide radicals from triacylhydroxylamine photolyses. J. Am. Chem. Soc., 95(8), 2630-2634.
Tearney, G.J. et al. (Jun. 27, 1997), In vivo endoscopic optical biopsy with optical coherence tomography, Science, 276, pp. 2037-2039.
Tilly et al., Endocrinology 131: 799, Aug. 1, 1992.
Toshio, Mukai et al. (Jan. 1, 1981), "photochemical behavior of cyclic imino ethers: The N—O bond fission, syn-anti isomerization and cycloaddition reactions in the C=N—0 chomophore," Journal of Photochemistry, vol. 17, No. 2, pp. 365-368.
Triesscheijn M. et al. (Oct. 2006), "Photodynamic Therapy in Oncology"; The Oncologist.; 11:1034-1044.
Tromberg, B.J. et al. (Jun. 29, 1997), Non-invasive measurements of breast tissue optical properties using frequency-domain photon migration, Phil. Trans. Royal Society London B, 352, pp. 661-668.
Vallabhajosula et al. (1996), "Preclinical Evaluation of Technetium-99m-Labeled Somatostatin Receptor-Binding Peptides," J. Nuclear Med., 37:1016, 1996.
Vargas, F. et al. (Jan. 1, 1999), "Study of the photochemical and in vitro phototoxicity of chlorthalodone [2-chloro-5-(1-hydroxy-3-oxo-1-isoindoliny 1)benzene sulfonamide]," Die Pharmazie, Govi Verlag Pharazeutischer Verlag GmbH, Exchborn, DE, vol. 54, No. 12, pp. 920-922.

Wagnieres, G.A. et al. (Nov. 1998), In vivo fluorescence spectroscopy and imaging for oncological applications, Photochem. Photobiol., 68, pp. 603-632.
Watterson, A. et al. (Jan. 1975), Photochemistry of acid hydrazides. Determination of modes of reaction and identification of photoproducts. J. Org. Chem., 40(1), 19-24.
Zhang, C. et al. (Jul. 1, 2009), "Synthesis and activity of quinolinylmethyl P1' alpha-sulfone piperidine hydroxamate inhibitors of TACE," Bioorganic & Medicinal Chemistry Letters, vol. 19, No. 13, pp. 3445-3448.
Zheng Huang (Jun. 2005), "A Review of Progress in Clinical Photodynamic Therapy", Technol Cancer Res Treat., 4(3): 283-293.
Written Opinion of the International Searching Authority issued Nov. 12, 2011 for International Application No. PCT/US10/34465.
International Search Report mailed Aug. 3, 2010 for International Application No. PCT/US10/34465.
Written Opinion of the International Searching Authority issued Nov. 12, 2011 for International Application No. PCT/US10/34523.
International Search Report mailed Nov. 18, 2010 for International Application No. PCT/US10/34523.
Written Opinion of the International Searching Authority issued Nov. 12, 2011 for International Application No. PCT/US10/34512.
International Search Report mailed Nov. 24, 2010 for International Application No. PCT/US10/34512.
Written Opinion of the International Searching Authority issued Nov. 12, 2011 for International Application No. PCT/US10/34480.
International Search Report mailed Jul. 23, 2010 for International Application No. PCT/US10/34480.

* cited by examiner

Hydrazine Alkylation

X and Y are independently Cl, Br, I, or p-TsO⁻
$R^1$-$R^2$ may optionally be tethered to form rings Azo-Diene Hetero Diels-Alder Reaction $R^3$-$R^4$; $R^5$-$R^6$; $R^6$-$R^7$; or $R^7$-$R^8$ may optionally be tethered to form rings

DIAZA HETEROCYCLIC COMPOUNDS FOR PHOTOTHERAPY

CROSS-REFERENCE TO RELATED APPLICATIONS

This application is a U.S. National Stage Application under 35 U.S.C. §371 of International Application No. PCT/US10/34523, filed May 12, 2010, which claims priority from and the benefit of U.S. Provisional Patent Application No. 61/177,334, filed May 12, 2009, all of which are incorporated by reference to the extent not inconsistent herewith.

BACKGROUND

Optical agents currently play a central role in a large number of in vivo, in vitro and ex vivo clinical procedures including important diagnostic and therapeutic procedures. Photodiagnostic and phototherapeutic agents, for example, include a class of molecules capable of absorbing, emitting, or scattering electromagnetic radiation applied to a biological material, particularly in the visible and near infrared regions of the electromagnetic spectrum. This property of optical agents is used in a range of biomedical applications for visualizing, imaging or otherwise characterizing biological materials and/or achieving a desired therapeutic outcome. Recent developments in targeted administration and delivery of optical agents, and advanced systems and methods for applying and detecting electromagnetic radiation in biological environments has considerably expanded the applicability and effectiveness of optical agents for clinical applications.

Important applications of optical agents that absorb and/or emit in the visible and near-infrared (NIR) region of the electromagnetic spectrum include their use in biomedical imaging and visualization. For example, compounds absorbing and/or emitting light in these regions of the electromagnetic spectrum currently are useful for optical tomography, optoacoustic tomography, optical coherence tomography, confocal scanning laser tomography, optical coherence tomography, and fluorescence endoscopy; techniques which have emerged as essential molecular imaging techniques for imaging and visualizing biological processes at the organ, cellular and subcellular (e.g., molecular) levels. Biomedical images are generated, for example, by detecting electromagnetic radiation, nuclear radiation, acoustic waves, electrical fields, and/or magnetic fields transmitted, emitted and/or scattered by components of a biological sample. Modulation of the energy or intensity of the applied radiation yields patterns of transmitted, scattered and/or emitted radiation, acoustic waves, electrical fields or magnetic fields that contain useful anatomical, physiological, and/or biochemical information. A number of applications of biomedical imaging have matured into robust, widely used clinical techniques including planar projection and tomographic X-ray imaging, magnetic resonance imaging, ultrasound imaging, and gamma ray imaging.

Established optical imaging and visualization techniques are based on monitoring spatial variations in a variety of optical parameters including the intensities, polarization states, and frequencies of transmitted, reflected, and emitted electromagnetic radiation. Given that many biological materials of interest are incompatible with ultraviolet light, research is currently directed to developing and enhancing imaging techniques using visible and near infrared (NIR) radiation (from about 400 nm to about 900 nm). In particular, NIR light (700 nm to 900 nm) is useful for visualizing and imaging deeper regions than visible light because electromagnetic radiation of this wavelength range is capable of substantial penetration (e.g., up to four centimeters) in a range of biological media. Optical imaging and visualization using optical agents has potential to provide a less invasive and safer imaging technology, as compared to X-ray, and other widely used nuclear medicine technologies. Applications of optical imaging for diagnosis and monitoring of the onset, progression and treatment of various disease conditions, including cancer, are well established. (See, e.g., D. A. Benaron and D. K. Stevenson, *Optical time-of-flight and absorbance imaging of biologic media, Science,* 1993, 259, pp. 1463-1466; R. F. Potter (Series Editor), *Medical optical tomography: functional imaging and monitoring,* SPIE Optical Engineering Press, Bellingham, 1993; G. J. Tearney et al., *In vivo endoscopic optical biopsy with optical coherence tomography, Science,* 1997, 276, pp. 2037-2039; B. J. Tromberg et al., *Non-invasive measurements of breast tissue optical properties using frequency-domain photon migration, Phil. Trans. Royal Society London B,* 1997, 352, pp. 661-668; S. Fantini et al., *Assessment of the size, position, and optical properties of breast tumors in vivo by noninvasive optical methods, Appl. Opt.,* 1998, 37, pp. 1982-1989; A. Pelegrin et al., *Photoimmunodiagnosis with antibody-fluorescein conjugates: in vitro and in vivo preclinical studies, J. Cell Pharmacol.,* 1992, 3, pp. 141-145).

Optical agents for in vivo and in vitro biomedical imaging, anatomical visualization and monitoring organ function are described in International Patent Publication WO2008/108941; U.S. Pat. Nos. 5,672,333; 5,698,397; 6,167,297; 6,228,344; 6,748,259; 6,838,074; 7,011,817; 7,128,896, and 7,201,892. In this context, optical imaging agents are commonly used for enhancing signal-to-noise and resolution of optical images and extending these techniques to a wider range of biological settings and media. In addition, use of optical imaging agents having specific molecular recognition and/or tissue targeting functionality has also been demonstrated as effective for identifying, differentiating and characterizing discrete components of a biological sample at the organ, tissue, cellular, and molecular levels. Further, optical agents have been developed as tracers for real time monitoring of physiological function in a patient, including fluorescence-based monitoring of renal function. (See International Patent Publication PCT/US2007/0149478). Given their recognized utility, considerable research continues to be directed toward developing improved optical agents for biomedical imaging and visualization.

In addition to their important role in biomedical imaging and visualization, optical agents capable of absorption in the visible and NIR regions have also been extensively developed for clinical applications for phototherapy. The benefits of phototherapy using optical agents are widely acknowledged as this technique has the potential to provide efficacy comparable to radiotherapy, while entirely avoiding exposure of non-target organs and tissue to harmful ionizing radiation. Photodynamic therapy (PDT), in particular, has been used effectively for localized superficial or endoluminal malignant and premalignant conditions. The clinical efficacy of PDT has also been demonstrated for the treatment of various other diseases, injuries, and disorders, including cardiovascular disorders such as atherosclerosis and vascular restenosis, inflammatory diseases, ophthalmic diseases and dermatological diseases. Visudyne and Photofrin, for example, are two optical agents that have been developed for the treatment of macular degeneration of the eye and for ablation of several types of tumors, respectively. (See, e.g., Schmidt-Drfurth, U.; Bringruber, R.; Hasan, T. *Phototherapy in ocular vascular disease.* IEEE Journal of Selected Topics in Quantum Electronics 1996, 2, 988-996; Mlkvy, P.; Messmann, H.; Regula, J.; Conio, M.; Pauer, M.; Millson, C. E.; MacRobert, A. J.; Brown, S. G. *Phototherapy for gastrointestinal tumors using three photosensitizers—ALA induced PPIX, Photofrin, and MTHPC*. A pilot study. Neoplasma 1998, 45, 157-161; Grosjean, P.; Wagieres, G.; Fontolliet, C.; Van Den Bergh, H.; Monnier, P. *Clinical phototherapy for superficial cancer in the esophagus and the bronchi: 514 nm compared with 630 nm light irradiation after sensitization with Photofrin II*. British Journal of Cancer 1998, 77, 1989-1955; Mitton, D.; Ackroyd, R. Phototherapy of Barrett's oesophagus and oesophageal carcinoma—how I do it. Photodiagnostics and Phototherapy 2006, 3, 96-98; and Li, L.; Luo, R.; Liao, W.; Zhang, M.; Luo, Y.; Miao, J. Clinical study of photofrin phototherapy for the treatment of relapse nasopharyngeal carcinoma. Photodiagnostics and Phototherapy 2006, 3, 266-271; See, Zheng Huang "A Review of Progress in Clinical Photodynamic Therapy", Technol Cancer Res Treat. 2005 June; 4(3): 283-293; "Photodiagnosis And Photodynamic Therapy", Brown S, Brown E A, Walker I. The present and future role of photodynamic therapy in cancer treatment. Lancet Oncol. 2004; 5:497-508; Triesscheijn M, Baas P, Schellens J H M. "Photodynamic Therapy in Oncology"; The Oncologist. 2006; 11:1034-1044; and Dougherty T J, Gomer C J, Henderson B W, Jori G, Kessel D, Korbelik M, Moan J, Peng Q. Photodynamic Therapy. J. Natl. Cancer Inst. 1998; 90:899-905).

Phototherapy is carried out by administration and delivery of a photosensitizer to a therapeutic target tissue (e.g., tumor, lesion, organ, etc.) followed by photoactivation of the photosensitizer by exposure to applied electromagnetic radiation. Phototherapeutic procedures require photosensitizers that are relatively chemically inert, and become activated only upon irradiation with light of an appropriate wavelength. Selective tissue injury can be induced with light when photosensitizers bind to the target tissues, either directly or through attachment to a bioactive carrier or targeting moiety. Photosensitizers essentially operate via two different pathways, classified as Types 1 and 2. A primary distinction between these classes of photosensitizers is that the Type 1 process operates via direct energy or electron transfer from the photosensitizer to the cellular components thereby inducing cell death, whereas the Type 2 process involves first the conversion of singlet oxygen from the triplet oxygen found in the cellular environment followed by either direct reaction of singlet oxygen with the cellular components or further generating secondary reactive species (e.g. peroxides, hydroxyl radical, etc.) which will induce cell death.

The Type 1 mechanism proceeds via a multistep process involving activation of the photosensitizer by absorption of electromagnetic radiation followed by direct interaction of the activated photosensitizer, or reactive intermediates derived from the photosensitizer, with the target tissue, for example via energy transfer, electron transfer or reaction with reactive species (e.g., radicals, ions, nitrene, carbene etc.) resulting in tissue damage. The Type 1 mechanism can be schematically represented by the following sequence of reactions:

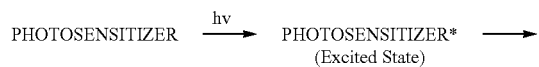

-continued

REACTIVE INTERMEDIATES
(e.g. Radicals)

CELL DEATH ←—Collision with Cell Components—— wherein hν indicates applied electromagnetic radiation and (PHOTOSENSITIZER)* indicates excited state of the photosensitizer. The Type 2 mechanism proceeds via a multi-step process involving activation of the photosensitizer by absorption of electromagnetic radiation followed by energy transfer from the activated photosensitizer to oxygen molecules in the environment of the target tissue. This energy transfer process generates excited state oxygen ($^1O_2$) which subsequently interacts with the target tissue so as to cause tissue damage. The Type 2 mechanism can be schematically represented by the following sequence of reactions:

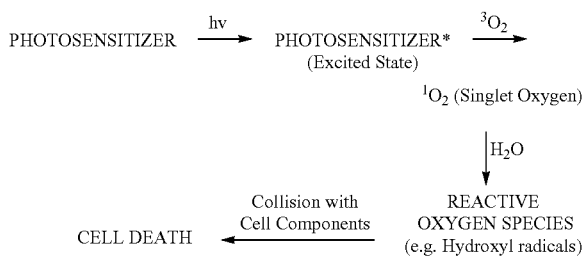

wherein hν indicates applied electromagnetic radiation, (PHOTOSENSITIZER)* indicates photoactivated photosensitizer, $^3O_2$ is ground state triplet oxygen, and $^1O_2$ is excited state singlet oxygen.

The biological basis of tissue injury brought about by tumor phototherapeutic agents has been the subject of intensive study. Various biochemical mechanisms for tissue damage have been postulated, which include the following: a) cancer cells up-regulate the expression of low density lipoprotein (LDL) receptors, and phototherapy (PDT) agents bind to LDL and albumin selectively; (b) porphyrin-like substances are selectively taken up by proliferative neovasculature; (c) tumors often contain increased number of lipid bodies and are thus able to bind to hydrophobic photosensitizers; (d) a combination of "leaky" tumor vasculature and reduced lymphatic drainage causes porphyrin accumulation referred to as "EPR" (enhanced permeability and retention) effect; (e) tumor cells may have increased capabilities for phagocytosis or pinocytosis of porphyrin aggregates; (f) tumor associated macrophages may be largely responsible for the concentration of photosensitizers in tumors; and (g) cancer cells may undergo apoptosis induced by photosensitizers. Among these mechanisms, (f) and (g) are the most general and, of these two alternatives, there is a general consensus that (f) is the most likely mechanism by which the phototherapeutic effect of porphyrin-like compounds is induced.

Much of the research in the past several decades has focused on developing phototherapeutic agents based on the Type 2 (PDT) mechanism. Surprisingly, there has been considerably less attention devoted to Type 1 phototherapeutic agents despite the fact that there are numerous classes of compounds that could potentially be useful for phototherapy that function via this mechanism. Unlike Type 2, the Type 1 process does not require oxygen; and hence Type 1 photosensitizers are expected to be potentially more effective than Type 2 photosensitizers under hypoxic environments typically found in solid tumors. Second, the Type 1 mechanism involves two steps (photoexcitation and direct energy transfer), whereas the Type 2 mechanism involves three steps (photoexcitation, singlet oxygen generation, and energy transfer). Further, studies have recently shown that production of high levels of reactive oxygen species can induce an anti-inflammatory response, which may result in blood vessels to become more "leaky," thereby increasing the risk of metastasis (Chen, B.; Pogue, B.; Luna, J. M.; Hardman, R. L.; Hoopes, P. J.; Hasan, T. Tumor vascular permeabilization by vascular-targeting photosensitization: effects, mechanism, and therapeutic implications. *Clinical Cancer Research* 2006, 12(3, Pt. 1), 917-923). Targeted Type 1 photosensitizers, by their very nature, are not expected to produce reactive oxygen species; rather, the reactive species produced by these photosensitizers will immediately react with the cellular component at the binding site and trigger cell death. Type 2 phototherapeutic agents, however, do have certain advantages over Type 1 agents. For example, Type 2 agents can potentially be catalytic, i.e., the Type 2 photosensitizer is regenerated once the energy transfer to the oxygen has taken place. In contrast, Type 1 process would generally be expected to require stoichiometric amounts of the photosensitizer in some clinical settings. Table I provides a summary of the attributes of Type 1 and Type 2 phototherapeutic agents. Given these attributes, it is clear that development of safe and effective Type 1 phototherapeutic agents would be useful to complement the existing therapeutic approaches provided by Type 2 agents, and to enhance the therapeutic portfolio available for clinicians.

TABLE 1

Comparison between Type 1 and Type 2 processes for phototherapy.

| TYPE 1 PROCESS | TYPE 2 PROCESS |
| --- | --- |
| Two-step process. | Three-step process. |
| Not well explored. | Very well studied. |
| Light of any wavelength can be used. | Requires red light for optimal performance. |
| Does not require oxygen. | Requires oxygen. |
| Large classes of compounds. | Limited classes of compounds. |
| Stoichiometric. | Potentially catalytic. |
| Intramolecular energy transfer to generate reactive species. | Intermolecular energy transfer to generate reactive oxygen species. |
| No products in the market. | Two products are in use. |

Specific optical, chemical and pharmacokinetic properties of optical agents are necessary for their effective use in Type 1 and Type 2 phototherapeutic applications. For example, optical agents for these applications preferably have strong absorption in the visible or NIR regions, and also exhibit low systemic toxicity, low mutagenicity, and rapid clearance from the blood stream. These optical agents must also be compatible with effective administration and delivery to the target tissue, for example by having reasonable solubilities and a low tendency for aggregation in solution. Upon excitation by absorption of visible and NIR electromagnetic radiation, optical agents for Type 1 and 2 phototherapy preferably provide large yields of singlet oxygen (Type 2) or other reactive species, such as free radicals or ions, capable of causing local tissue damage. Both Type 1 and Type 2 photosensitizers typically undergo photoactivation followed by intersystem crossing to their lowest triplet excited state, and therefore, a relatively long triplet lifetime is usually beneficial for providing effective tissue damage. Other useful properties of optical agents for these applications include chemical inertness and stability, insensitivity of optical properties to changes in pH, and compatibility with conjugation to ligands providing targeted delivery via molecular recognition functionality. Multifunctional optical agents have also been developed for phototherapy that are capable of providing both imaging and visual functionality upon excitation at a first range of wavelengths and phototherapeutic functionality upon excitation at a second range of wavelength. (See, U.S. Pat. No. 7,235,685 and International Patent Publication WO 2007/106436).

Optical agents for some phototherapeutic applications preferably exhibit a high degree of selectivity for the target tissue. Selectivity provided by optical agents facilitates effective delivery to a target tissue of interest and provides a means of differentiating different tissue classes during therapy. Selective tissue injury can be induced with light when photosensitizers bind to the target tissues either directly, as in the case of Photofrin, or through attachment to a bioactive carrier, or through in situ biochemical synthesis of the photosensitizer in localized area, as in the case of 2-aminolevulinic acid, which is an intermediate in the biosynthesis of porphyrin. Previous studies have shown that certain dyes selectively localize in tumors and serve as a powerful probe for the detection and treatment of small cancers. (D. A. Belinier et al., Murine pharmacokinetics and antitumor efficacy of the photodynamic sensitizer 2-[I-hexyloxyethyl]-2-devinyl pyropheophorbide-a, J. Photochem. Photobiol., 1993, 20, pp. 55-61; G. A. Wagnieres at al., In vivo fluorescence spectroscopy and imaging for oncological applications, Photochem. Photobiol., 1998, 68, pp. 603-632; J. S. Reynolds et al., Imaging of spontaneous canine mammary tumors using fluorescent contrast agents, Photochem. Photobiol., 1999, 70, pp. 87-94). It is recognized in some situations, however, that many dyes do not localize preferentially in malignant tissues. A number of strategies have been developed for imparting selectivity and/or targeting functionality by incorporation of a molecular recognition component in the optical agent. For example, targeting of fluorescent dyes to tumors has been demonstrated using dye conjugates with antibodies and peptides for diagnostic imaging of tumors. (See, Achilefu at al., Novel receptor-targeted fluorescent contrast agents for in vivo imaging of tumors, Investigative Radiology, 2000, 35, pp. 479-485; Ballou et al., Tumor labeling in vivo using cyanine conjugated monoclonal antibodies, Cancer Immunology and Immunotherapy, 1995, 41, pp. 257-263; and Licha at al., New contrast agent for optical imaging: acid cleavable conjugates of cyanine dyes with biomolecules, in Biomedical Imaging: Reporters, Dyes and Instrumentation, Proceedings of SPIE, 1999, 3600, pp. 29-35). Therefore, receptor-target mediated phototherapy agents provide a promising pathway for achieving site selective activation at various target tissues.

As will be generally recognized from the foregoing, a need currently exists for optical agents for biomedical applications. Specifically, optical agents for imaging, visualization and phototherapy are needed having enhanced specificity for important target tissue classes, such as tumors and other lesions. In addition, optical agents are needed having enhanced optical, physical, chemical and pharmacokinetic properties for administration, delivery and excitation with electromagnetic radiation.

SUMMARY

The invention relates generally to optical agents, including phototherapeutic agents, for biomedical applications, including phototherapy. The invention includes optical agents, and related therapeutic methods, comprising alicyclic diaza compounds, including 1,2 diaza heterocyclic compounds, having a photolabile N—N bond directly or indirectly linked to at least one carbocyclic or heterocyclic aromatic group such as a $C_5$-$C_{30}$ aryl or $C_5$-$C_{30}$ heteroaryl group, or optionally a $C_5$-$C_{20}$ aryl or $C_5$-$C_{20}$ heteroaryl group, or optionally a $C_5$-$C_{10}$ aryl or $C_5$-$C_{10}$ heteroaryl group. In some embodiments, for example, the invention provides acyclic diaza compounds for phototherapeutic methods having a photolabile N—N bond that undergoes photoactivated cleavage to produce reactive species, such as radicals, ions, etc., that achieve a desired therapeutic effect, such as selective and/or localized tissue damage and/or cell death. Optical agents of an aspect of the invention include compositions having one or more aromatic and/or heterocyclic aromatic groups, such as a $C_5$-$C_{30}$ aryl or $C_5$-$C_{30}$ heteroaryl group providing a chromophore directly or indirectly coupled to an alicyclic diaza ring having a N—N bond that undergoes photodissociation and/or photoactivation upon exposure to electromagnetic radiation having wavelengths in the visible and/or near infrared regions of the electromagnetic spectrum. Optical agents further include conjugates, for example, compositions including at least one targeting ligand such as a peptide, protein, oligonucleotide, or other biomolecule, or fragments thereof, capable of providing molecular recognition and/or targeting functionality. Optical agents further include multifunctional optical agents comprising a diaza photosensitizer component linked to an optical dye component providing tandem imaging and phototherapy functionality.

In an aspect, the invention provides diaza compounds containing an N—N bond provided in an alicyclic ring useful as optical agents for phototherapeutic methods, including Type 1 phototherapy. In an embodiment, for example, the invention provides a compound for use in a phototherapy procedure, the compound being of the formula (FX1):

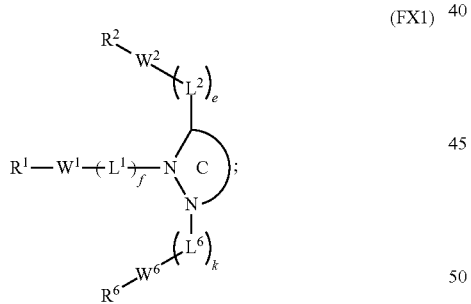

(FX1)

or a pharmaceutically acceptable salt or ester thereof, wherein ring C is:

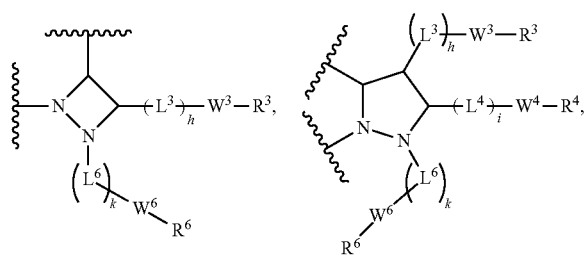

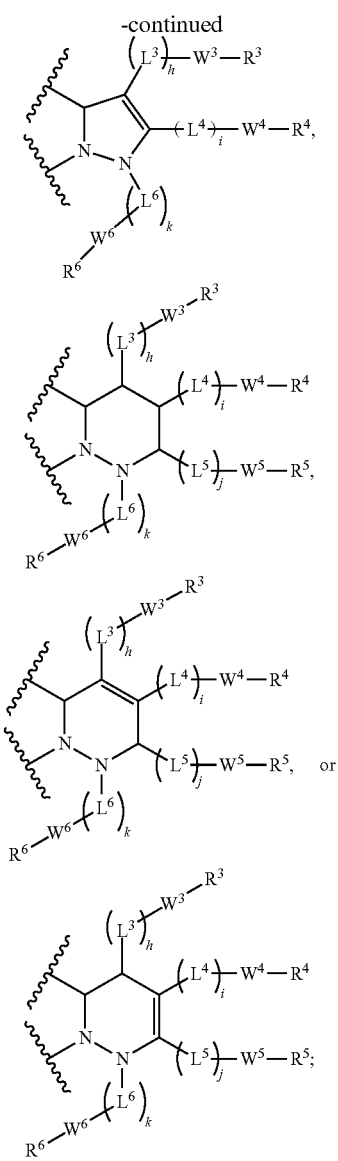

or a pharmaceutically acceptable salt or ester thereof;

each of $L^1$-$L^6$, if present, is independently $C_1$-$C_{10}$ alkylene, $C_3$-$C_{10}$ cycloalkylene, $C_2$-$C_{10}$ alkenylene, $C_3$-$C_{10}$ cycloalkenylene, $C_2$-$C_{10}$ alkynylene, ethenylene, ethynylene, phenylene, 1-aza-2,5-dioxocyclopentylene, —(CH$_2$CH$_2$O)$_m$—, —(CHOH)$_m$—, or 1,4-diazacyclohexylene;

each of $W^1$ and $W^6$ is independently a single bond, —(CH$_2$)$_n$—, —(HCCH)$_n$—, —O—, —S—, —SO—, —SO$_2$—, —SO$_3$—, —OSO$_2$—, —NR$^7$—, —CO—, —COO—, —OCO—, —OCOO—, —CONR$^8$—, —NR$^9$CO—, —OCONR$^{10}$—, —NR$^{11}$COO—, —NR$^{12}$CONR$^{13}$—, or —NR$^{14}$CSNR$^{15}$—;

each of $W^2$-$W^5$ is independently a single bond, a double bond, —(CH$_2$)$_n$—, —(HCCH)$_n$—, —O—, —S—, —SO—, —SO$_2$—, —SO$_3$—, —OSO$_2$—, —NR$^7$—, —CO—, —COO—, —OCO—, —OCOO—, —CONR$^8$—, —NR$^9$CO—, —OCONR$^{10}$—, —NR$^{11}$COO—, —NR$^{12}$CONR$^{13}$—, or —NR$^{14}$CSNR$^{15}$—;

each of $R^1$ and $R^6$ is independently hydrogen, $C_1$-$C_{20}$ alkyl, $C_3$-$C_{20}$ cycloalkyl, $C_5$-$C_{30}$ aryl, $C_5$-$C_{30}$ heteroaryl, $C_1$-$C_{20}$ acyl, $C_2$-$C_{20}$ alkenyl, $C_2$-$C_{20}$ alkynyl, $C_5$-$C_{20}$ alkylaryl, $C_1$-$C_6$ alkoxycarbonyl, halo, halomethyl, dihalomethyl, trihalomethyl, —CN, —CO$_2$R$^{16}$, —CONR$^{17}$R$^{18}$, —COR$^{19}$, —NO$_2$, —SOR$^{20}$, —OSR$^{21}$, —SO$_2$R$^{22}$, —SO$_2$OR$^{23}$, —SO$_2$NR$^{24}$R$^{25}$, —PO$_3$R$^{26}$R$^{27}$, —OR$^{28}$, —SR$^{29}$, —NR$^{30}$R$^{31}$, —NR$^{32}$COR$^{33}$, —(CHOH)$_m$R$^{34}$, —(CH$_2$CH$_2$O)$_m$R$^{35}$, —CH(R$^{36}$)CO$_2$H, —CH(R$^{37}$)NH$_2$, a dye, or Bm;

each of R$^2$-R$^5$ is independently hydrogen, C$_1$-C$_{20}$ alkyl, C$_3$-C$_{20}$ cycloalkyl, C$_5$-C$_{30}$ aryl, C$_5$-C$_{30}$ heteroaryl, C$_1$-C$_{20}$ acyl, C$_2$-C$_{20}$ alkenyl, C$_2$-C$_{20}$ alkynyl, C$_5$-C$_{20}$ alkylaryl, C$_1$-C$_6$ alkoxycarbonyl, halo, halomethyl, dihalomethyl, trihalomethyl, =O, =S, —CN, —CO$_2$R$^{16}$, —CONR$^{17}$R$^{18}$, —COR$^{19}$, —NO$_2$, —SOR$^{20}$, —OSR$^{21}$, —SO$_2$R$^{22}$, —SO$_2$OR$^{23}$, —SO$_2$NR$^{24}$R$^{25}$, —PO$_3$R$^{26}$R$^{27}$, —OR$^{28}$, —SR$^{29}$, —NR$^{30}$R$^{31}$, —NR$^{32}$COR$^{33}$, —(CHOH)$_m$R$^{34}$, —(CH$_2$CH$_2$O)$_m$R$^{36}$, —CH(R$^{36}$)CO$_2$H, —CH(R$^{37}$)NH$_2$, a dye, or Bm;

or wherein at least two of R$^1$-R$^6$ combine to form one or more alicyclic or aromatic, carbocyclic or heterocyclic 5 or 6 membered rings;

wherein at least one of R$^1$-R$^6$ is C$_5$-C$_{30}$ aryl or C$_5$-C$_{30}$ heteroaryl, or wherein at least two of R$^1$-R$^6$ combine to form C$_5$-C$_{30}$ aryl or C$_5$-C$_{30}$ heteroaryl;

each m is independently an integer selected from the range of 1 to 100;

each n is independently an integer selected from the range of 1 to 10;

each of f, e, h, i, j and k is independently 0 or 1;

each of R$^7$-R$^{33}$ is independently hydrogen, C$_1$-C$_{20}$ alkyl, C$_5$-C$_{30}$ aryl or C$_5$-C$_{30}$ heteroaryl;

each of R$^{34}$ and R$^{35}$ is independently hydrogen or C$_1$-C$_{10}$ alkyl;

each of R$^{36}$ and R$^{37}$ is independently a side chain residue of a natural α-amino acid; and each Bm is independently an amino acid, a peptide, a protein, a nucleoside, a nucleotide, an enzyme, a carbohydrate, a glycomimetic, an oligomer, a lipid, a polymer, an antibody, an antibody fragment, a mono- or polysaccharide comprising 1 to 50 carbohydrate units, a glycopeptide, a glycoprotein, a peptidomimetic, a drug, a steroid, a hormone, an aptamer, a receptor, a metal chelating agent, a polynucleotide comprising 2 to 50 nucleic acid units, a peptoid comprising 2 to 50 N-alkylaminoacetyl residues, a glycopeptide comprising 2 to 50 amino acid and carbohydrate units, or a polypeptide comprising 2 to 30 amino acid units.

As used throughout the present description, embodiments wherein at least two of R$^1$-R$^6$ combine to form one or more alicyclic or aromatic, carbocyclic or heterocyclic 5 or 6 membered rings refers to compounds of the present invention having a polycyclic fused ring structure, for example, wherein two or more adjacent R$^1$, R$^2$, R$^3$, R$^4$, R$^5$, and/or R$^6$, along with two or more of W$^1$, W$^2$, W$^3$, W$^4$, W$^5$, and/or W$^6$, and L$^1$, L$^2$, L$^3$, L$^4$, L$^5$, and/or L$^6$, if present, and atoms of the central alicyclic diaza ring, are bound to each other to form a carbocyclic or heterocyclic ring structure fused to the central alicyclic diaza ring. Such embodiments include compounds, for example, wherein two or more adjacent R$^1$, R$^2$, R$^3$, R$^4$, R$^5$, and/or R$^6$, along with two or more of W$^1$, W$^2$, W$^3$, W$^4$, W$^5$, and/or W$^6$ and L$^1$, L$^2$, L$^3$, L$^4$, L$^5$, and/or L$^6$, if present, are tethered to each other to form one or more alicyclic or aromatic ring structures fused to the central alicyclic diaza ring. In an embodiment, for example, R$^1$, R$^2$, W$^1$, W$^2$, and L$^1$ and L$^2$ (if present); or R$^2$, R$^3$, W$^2$, W$^3$, and L$^2$ and L$^3$ (if present); or R$^3$, R$^4$, W$^3$, W$^4$, and L$^3$ and L$^4$ (if present); or R$^4$, R$^5$, W$^4$, W$^5$, and L$^4$ and L$^5$ (if present); or R$^5$, R$^6$, W$^5$, W$^6$, and L$^5$ and L$^6$ (if present), along with atoms of the central alicyclic diaza ring, combine to form one or more alicyclic or aromatic, carbocyclic or heterocyclic 5 or 6 membered rings fused to the central alicyclic diaza ring.

In an embodiment, the invention provides compounds useful as optical agents for phototherapeutic methods having formula (FX1), wherein at least one of W$^1$-W$^6$ is a single bond, and wherein at least one of f, e, h, i, j and k is 0, thereby providing direct coupling of at least one of R$^1$-R$^6$ to the central diaza ring of the compound. In an embodiment, for example, the invention provides compounds useful as optical agents for phototherapeutic methods having formula (FX1), wherein f is 0 and W$^1$ is a single bond; or wherein e is 0 and W$^2$ is a single bond; or wherein h is 0 and W$^3$ is a single bond; or wherein i is 0 and W$^4$ is a single bond; or wherein j is 0 and W$^5$ is a single bond; wherein k is 0 and W$^6$ is a single bond. In an embodiment, the invention provides compounds useful as optical agents for phototherapeutic methods having formula (FX1), wherein each of f, e, h, i, j and k is 0, and wherein each of W$^1$-W$^6$ is a single bond. The present invention includes compositions comprising enantiomers, diastereomers and/or ionic forms (e.g., protonated and deprotonated forms) of the compounds of formula (FX1).

In an embodiment, the invention provides compounds useful as optical agents for phototherapeutic methods having formula (FX1), wherein at least one of W$^2$-W$^5$ is a double bond, and wherein at least one of e, h, i, and j is 0, thereby providing direct coupling of at least one of R$^2$-R$^5$ to the central diaza ring of the compound via a double bond. In an embodiment, for example, the invention provides compounds useful as optical agents for phototherapeutic methods having formula (FX1), wherein e is 0 and W$^2$ is a double bond; or wherein h is 0 and W$^3$ is a double bond; or wherein i is 0 and W$^4$ is a double bond; or wherein j is 0 and W$^5$ is a double bond. In an embodiment, the invention provides compounds useful as optical agents for phototherapeutic methods having formula (FX1), wherein each of e, h, i, and j is 0, and wherein each of W$^2$-W$^5$ is a double bond. In an embodiment, the invention provides compounds useful as optical agents for phototherapeutic methods having formula (FX1), wherein at least one of W$^2$-W$^5$ is a double bond, and wherein at least one of R$^2$-R$^5$ is =O or =S, and wherein at least one of e, h, i, and j is 0, thereby providing direct coupling of O or S to the central diaza ring of the compound via a double bond. In an embodiment, for example, the invention provides compounds useful as optical agents for phototherapeutic methods having formula (FX1), wherein e is 0, W$^2$ is a double bond, and R$^2$ is =O; or wherein h is 0, W$^3$ is a double bond, and R$^3$ is =O; or wherein i is 0, W$^4$ is a double bond, and R$^4$ is =O; or wherein j is 0, W$^5$ is a double bond, and R$^5$ is =O.

In an embodiment, the composition of R$^1$-R$^6$, W$^1$-W$^6$, and L$^1$-L$^6$ in formula (FX1) is selected such that the compound undergoes cleavage of a photolabile N—N bond of the central alicyclic diaza ring upon exposure to electromagnetic radiation having wavelengths selected over the range of 350 nanometers to 1300 nanometers, and optionally wavelengths selected over the range of 350 nanometers to 900 nanometers. In an embodiment, the invention provides compounds useful as optical agents for phototherapeutic methods having formula (FX1), wherein R$^1$ is C$_5$-C$_{30}$ aryl or C$_5$-C$_{30}$ heteroaryl, and each of R$^2$-R$^6$ is independently hydrogen, C$_1$-C$_{20}$ alkyl, C$_5$-C$_{30}$ aryl, C$_5$-C$_{30}$ heteroaryl, a dye, or Bm; or wherein R$^2$ is C$_5$-C$_{30}$ aryl or C$_5$-C$_{30}$ heteroaryl, and each of R$^1$ and R$^3$-R$^6$ is independently hydrogen, C$_1$-C$_{20}$ alkyl, C$_5$-C$_{30}$ aryl, C$_5$-C$_{30}$ heteroaryl, a dye, or Bm; or wherein R$^3$ is C$_5$-C$_{30}$ aryl or C$_5$-C$_{30}$ heteroaryl, and each of R$^1$-R$^2$ and R$^4$-R$^6$ is independently hydrogen, C$_1$-C$_{20}$ alkyl, C$_5$-C$_{30}$ aryl, C$_5$-C$_{30}$ heteroaryl, a dye, or Bm; or wherein R$^4$ is C$_5$-C$_{30}$ aryl or C$_5$-C$_{30}$ heteroaryl, and each of $R^1$-$R^3$ and $R^5$-$R^6$ is independently hydrogen, $C_1$-$C_{20}$ alkyl, $C_5$-$C_{30}$ aryl, $C_5$-$C_{30}$ heteroaryl, a dye, or Bm; or wherein $R^5$ is $C_5$-$C_{30}$ aryl or $C_5$-$C_{30}$ heteroaryl, and each of $R^1$-$R^4$ and $R^6$ is independently hydrogen, $C_1$-$C_{20}$ alkyl, $C_5$-$C_{30}$ aryl, $C_5$-$C_{30}$ heteroaryl, a dye, or Bm; or wherein $R^6$ is $C_5$-$C_{30}$ aryl or $C_5$-$C_{30}$ heteroaryl, and each of $R^1$-$R^5$ is independently hydrogen, $C_1$-$C_{20}$ alkyl, $C_5$-$C_{30}$ aryl, $C_5$-$C_{30}$ heteroaryl, a dye, or Bm. In an embodiment, the invention provides compounds useful as optical agents for phototherapeutic methods having formula (FX1), wherein each of $R^1$-$R^6$ is independently hydrogen, $C_1$-$C_{10}$ alkyl, $C_5$-$C_{30}$ aryl, $C_5$-$C_{30}$ heteroaryl, —CN, —$CONR^{17}R^{18}$, —$COR^{19}$, —$NO_2$, —$SO_2R^{22}$, —$SO_2NR^{24}R^{25}$, —$OR^{28}$, —$NR^{30}R^{31}$, —$NR^{32}COR^{33}$, —$SR^{29}$, a dye, or Bm. In an embodiment, the invention provides compounds useful as optical agents for phototherapeutic methods having formula (FX1), wherein each of $R^1$-$R^6$ is independently hydrogen, $C_1$-$C_{10}$ alkyl, $C_5$-$C_{30}$ aryl, $C_5$-$C_{30}$ heteroaryl, a dye, or Bm.

In an embodiment, the invention provides compounds useful as optical agents for phototherapeutic methods having formula (FX1), wherein one or more of $R^1$-$R^6$ is independently, or at least two or more of $R^1$-$R^6$ combine to form one or more carbocyclic and/or heterocyclic aromatic groups providing a chromophore capable of excitation upon exposure to electromagnetic radiation having wavelengths selected over the range of 350 nanometers to 1300 nanometers, and optionally wavelengths selected over the range of 350 nanometers to 900 nanometers. The invention includes compounds wherein one or more of $R^1$-$R^6$ is independently, or at least two or more of $R^1$-$R^6$ combine to form, a $C_5$-$C_{30}$ aryl or $C_5$-$C_{30}$ heteroaryl, optionally a $C_5$-$C_{20}$ aryl or $C_5$-$C_{30}$ heteroaryl, or a $C_5$-$C_{10}$ aryl or $C_5$-$C_{30}$ heteroaryl, providing an aromatic antenna for photosensitization, for example, useful for coupling electromagnetic radiation into a phototherapeutic agent to initiate generation of reactive species in a phototherapeutic procedure. In an embodiment, for example, the invention provides compounds useful as optical agents for phototherapeutic methods having formula (FX1), wherein one or more of $R^1$-$R^6$ is independently, or at least two or more of $R^1$-$R^6$ combine to form, a group corresponding to benzene, naphthalene, naphthoquinone, diphenylmethane, fluorene, anthracene, anthraquinone, phenanthrene, tetracene, naphthacenedione, pyridine, quinoline, isoquinoline, indole, isoindole, pyrrole, imidazole, oxazole, thiazole, pyrazole, pyrazine, pyrimidine, purine, benzimidazole, furan, benzofuran, dibenzofuran, carbazole, acridine, acridone, phenanthridine, thiophene, benzothiophene, dibenzothiophene, xanthene, xanthone, flavone, coumarin, azulene, azaazulene or anthracycline. As used throughout the present description, the expression "a group corresponding to" an indicated species expressly includes an aromatic group or heterocyclic aromatic group of the species or group of species provided in a covalently bonded configuration, optionally with one or more substituents, including but not limited to electron donating groups, electron withdrawing groups and/or targeting ligands. In an embodiment, for example, the invention provides compounds useful as optical agents for phototherapeutic methods having formula (FX1), wherein one or more of $R^1$-$R^6$ is independently, or at least two or more of $R^1$-$R^6$ combine to form, $C_5$-$C_{30}$ aryl or $C_5$-$C_{30}$ heteroaryl, optionally a $C_5$-$C_{20}$ aryl or $C_5$-$C_{20}$ heteroaryl, or a $C_5$-$C_{10}$ aryl or $C_5$-$C_{10}$ heteroaryl, comprising one or more carbocyclic or heterocyclic aromatic rings having at least one electron donating group as a substituent, or having at least one electron withdrawing group as a substituent, or having at least one electron withdrawing group and at least one electron donating group as substituents.

The present invention includes compounds useful as optical agents for phototherapeutic methods having formula (FX1) wherein ring C is a four membered alicyclic ring. In an embodiment, for example, the invention provides a compound for phototherapy being of the formula (FX2):

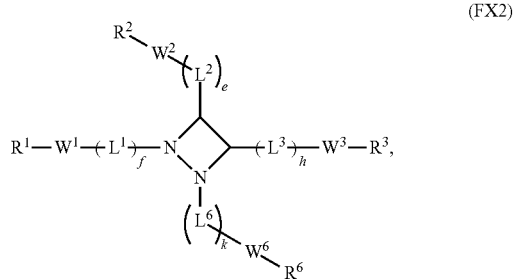

or a pharmaceutically acceptable salt or ester thereof, wherein e, f, h, k, $R^1$-$R^3$, $R^6$, $W^1$-$W^3$, $W^6$, $L^1$-$L^3$ and $L^6$ are as defined in the context of formula (FX1). The present invention includes compounds useful as optical agents for phototherapeutic methods having formula (FX1) wherein ring C is a five membered alicyclic ring. In an embodiment, for example, the invention provides a compound for phototherapy being of the formula (FX3) or (FX4):

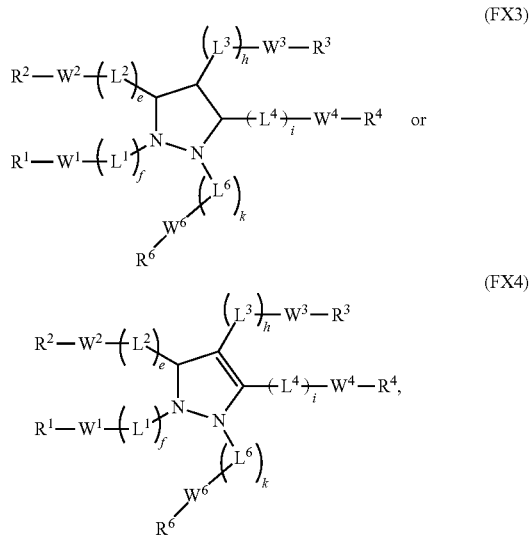

or a pharmaceutically acceptable salt or ester thereof; wherein e, f, h, i, k, $R^1$-$R^4$, $R^6$, $W^1$-$W^4$, $W^6$, $L^1$-$L^4$ and $L^6$ are as defined in the context of formula (FX1). The present invention includes compounds useful as optical agents for phototherapeutic methods having formula (FX1) wherein ring C is a six membered alicyclic ring. In an embodiment, for example, the invention provides a compound for phototherapy being of the formula being of the formula (FX5), (FX6), or (FX7):

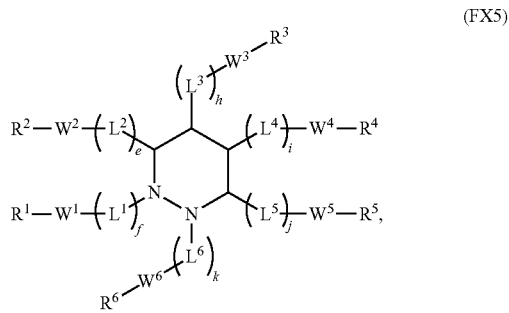

-continued

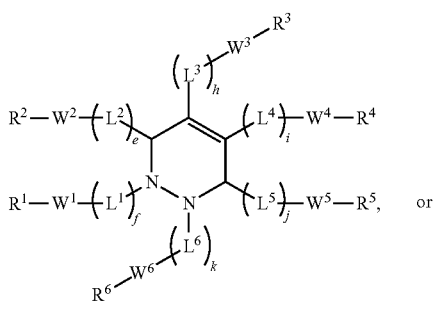

(FX6)

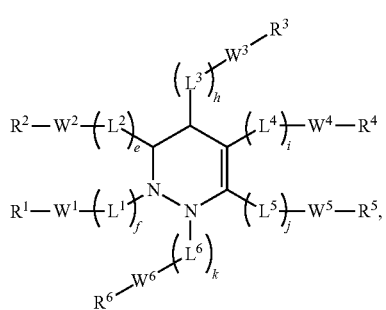

(FX7)

or a pharmaceutically acceptable salt or ester thereof, wherein, e, f, h, i, j, k, $R^1$-$R^6$, $W^1$-$W^6$ and $L^1$-$L^6$ are as defined in the context of formula (FX1). The present invention includes compositions comprising enantiomers, diastereomers and/or ionic forms (e.g., protonated and deprotonated forms) of the compounds of formula (FX2)-(FX7).

The invention includes compounds for use in a phototherapeutic method having any one of formulae (FX1)-(FX7), wherein two or more of $R^1$-$R^6$, together with any of $W^1$-$W^6$ and $L^1$-$L^6$, if present, and atoms of the central alicyclic diaza ring combine to form one or more alicyclic or aromatic rings fused to the central alicyclic diaza ring. The invention includes compounds for use in a phototherapeutic method having any one of formulae (FX1)-(FX7), wherein $R^1$, $R^2$, $W^1$, $W^2$, together with $L^1$ and $L^2$, if present; or $R^2$, $R^3$, $W^2$, $W^3$, together with $L^2$ and $L^3$, if present; or $R^3$, $R^4$, $W^3$, $W^4$, together with $L^3$ and $L^4$, if present; or $R^4$, $R^6$, $W^4$, $W^6$, together with $L^4$ and $L^6$, if present; or $R^4$, $R^5$, $W^4$, $W^5$, together with $L^4$ and $L^5$, if present; or $R^5$, $R^6$, $W^5$, $W^6$, together with $L^5$ and $L^6$, if present; combine to form —(CH$_2$)$_p$—, —(CH$_2$)$_q$R(CH$_2$)$_r$—, —C($R^{45}$)═C($R^{46}$)—C($R^{47}$)═C($R^{48}$)—, —N═C($R^{49}$)—C($R^{50}$)═C($R^{51}$)—, —C($R^{52}$)═N—C($R^{53}$)═C($R^{54}$)—, —C($R^{55}$)═C($R^{56}$)—N═C($R^{57}$)—, —C($R^{58}$)═C($R^{59}$)—C($R^{60}$)═N—, —C($R^{61}$)═C($R^{62}$)—N($R^{63}$)—, —C($R^{64}$)═C($R^{65}$)—O—, —C($R^{66}$)═C($R^{67}$)—S—, —N═C($R^{68}$)—N($R^{69}$)—, —C═C($R^{70}$)—O—, —N═C($R^{71}$)—S—, —C($R^{72}$)═N—N($R^{73}$)—, —C($R^{74}$)═N—N($R^{75}$)—, —C($R^{76}$)═N—O—, —N═N—N($R^{77}$)—, —N═N—O—, or —N═N—S—; wherein p is 1, 2, 3, 4, or 5, each of q and r is independently 0, 1, 2, or 3, and wherein the sum of q and r is 2, 3, 4, 5, or 6; and wherein R is —O—, —N($R^{78}$)—, —S—, —SO— or —SO$_2$—; wherein each of $R^{45}$-$R^{78}$ is independently hydrogen, $C_1$-$C_{10}$ alkyl, $C_5$-$C_{10}$ aryl or $C_5$-$C_{10}$ heteroaryl.

Compounds of this aspect of the invention have a polycyclic fused ring structure that includes ring C. In an embodiment of this aspect wherein $R^1$ and $R^2$ together with $W^1$, $W^2$, and $L^1$, and $L^2$, if present, together with atoms of the central diaza ring combine to form ring B, for example, the invention provides a compound for phototherapy being of the formula (FX8):

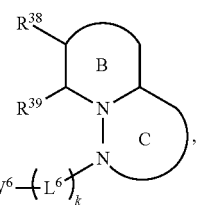

(FX8)

or a pharmaceutically acceptable salt or ester thereof; wherein ring C is as defined in the context of formula (FX1), wherein ring B is a 5 or 6 membered alicyclic or aromatic, carbocyclic or heterocyclic ring, and wherein each of $R^{38}$-$R^{39}$ is independently hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_2$-$C_{10}$ alkenyl, $C_2$-$C_{10}$ alkynyl, $C_6$-$C_{10}$ alkylaryl, $C_1$-$C_6$ alkoxycarbonyl, halo, halomethyl, dihalomethyl, trihalomethyl, —CN, —CO$_2$$R^{16}$, —CONR$^{17}$$R^{18}$, —COR$^{19}$, —NO$_2$, —SOR$^{20}$, —OSR$^{21}$, —SO$_2$$R^{22}$, —SO$_2$OR$^{23}$, —SO$_2$NR$^{24}$$R^{25}$, —PO$_3$$R^{26}$$R^{27}$, —OR$^{28}$, —SR$^{29}$, —NR$^{30}$$R^{31}$, or —NR$^{32}$COR$^{33}$. In an embodiment of this aspect wherein $R^2$ and $R^3$ together with $W^2$, $W^3$, $L^2$, and $L^3$, if present, together with atoms of the central diaza ring, combine to form a 6 membered carbocyclic or heterocyclic aromatic ring, the invention provides a compound for phototherapy being of the formula (FX9):

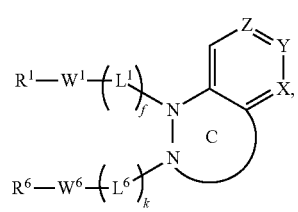

(FX9)

or a pharmaceutically acceptable salt or ester thereof, wherein ring C, f, k and $R^1$, $R^6$, $W^1$, $W^6$, $L^1$ and $L^6$ are as defined in the context of formula (FX1), wherein X is —CR$^{41}$— or —N—; wherein Y is —CR$^{42}$— or —N—; wherein Z is —CR$^{43}$— or —N—; wherein each of $R^{41}$-$R^{43}$ is independently hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_2$-$C_{10}$ alkenyl, $C_2$-$C_{10}$ alkynyl, $C_5$-$C_{10}$ alkylaryl, $C_1$-$C_6$ alkoxycarbonyl, halo, halomethyl, dihalomethyl, trihalomethyl, —CN, —CO$_2$$R^{16}$, —CONR$^{17}$$R^{18}$, —COR$^{19}$, —NO$_2$, —SOR$^{20}$, —OSR$^{21}$, —SO$_2$$R^{22}$, —SO$_2$OR$^{23}$, —SO$_2$NR$^{24}$$R^{25}$, —PO$_3$$R^{26}$$R^{27}$, —OR$^{28}$, —SR$^{29}$, —NR$^{30}$$R^{31}$, or —NR$^{32}$COR$^{33}$.

In an embodiment of this aspect wherein $R^1$ and $R^2$ together with $W^1$, $W^2$, and $L^1$ and $L^2$, if present, together with atoms of the central diaza ring combine to form ring B, and $R^2$ and $R^3$ combine to form a 6 membered carbocyclic or heterocyclic aromatic ring, the invention provides a compound for phototherapy being of the formula (FX10):

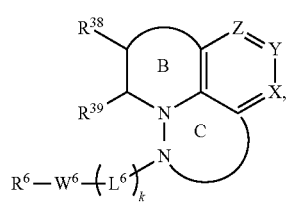

(FX10)

or a pharmaceutically acceptable salt or ester thereof; wherein ring C is defined in the context of formula (FX1), wherein ring B is an alicyclic or aromatic, carbocyclic or heterocyclic 5 membered or 6 membered ring; wherein X is —$CR^{41}$— or —N—; wherein Y is —$CR^{42}$— or —N—; wherein Z is —$CR^{43}$— or —N—; wherein each of $R^{38}$, $R^{39}$, and $R^{41}$-$R^{43}$ is independently hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_2$-$C_{10}$ alkenyl, $C_2$-$C_{10}$ alkynyl, $C_5$-$C_{10}$ alkylaryl, $C_1$-$C_6$ alkoxycarbonyl, halo, halomethyl, dihalomethyl, trihalomethyl, —CN, —$CO_2R^{16}$, —$CONR^{17}R^{18}$, —$COR^{19}$, —$NO_2$, —$SOR^{20}$, —$OSR^{21}$, —$SO_2R^{22}$, —$SO_2OR^{23}$, —$SO_2NR^{24}R^{25}$, —$PO_3R^{26}R^{27}$, —$OR^{28}$, —$SR^{29}$, —$NR^{30}R^{31}$, or —$NR^{32}COR^{33}$. The present invention includes compositions comprising enantiomers, diastereomers and/or ionic forms (e.g., protonated and deprotonated forms) of the compounds of formula (FX8)-(FX10).

In an embodiment of this aspect wherein ring B is a five membered ring, the invention provides a compound for use in a phototherapeutic method being of the formula (FX11) or (FX12):

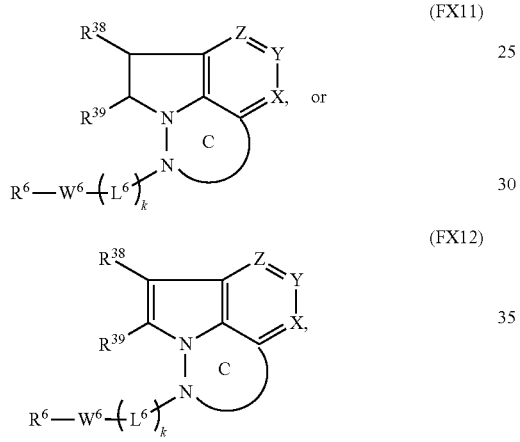

or a pharmaceutically acceptable salt or ester thereof, wherein ring C is defined in the context of formula (FX1), wherein $R^6$, $W^6$, $L^6$, X, Y, Z, and $R^{38}$-$R^{39}$ are as defined in the context of formulae (FX9) and (FX10). The invention of this aspect include compounds being of the formula (FX13), (FX14), (FX15), (FX16), (FX17), (FX18), (FX19), or (FX20):

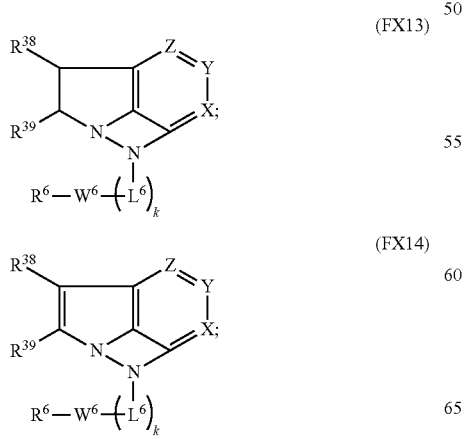

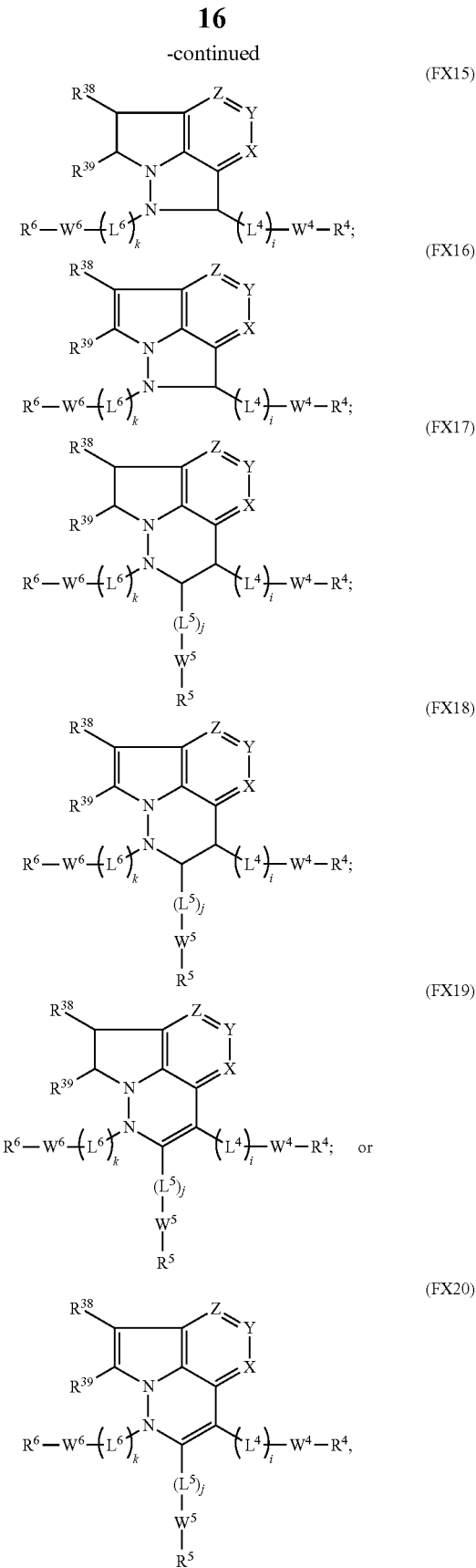

or a pharmaceutically acceptable salt or ester thereof, wherein i, j, k, $R^4$, $R^5$, $R^6$, $W^4$, $W^5$, $W^6$, $L^4$, $L^5$ and $L^6$ are as defined in the context of formula (FX1), and X, Y, Z, and $R^{38}$-$R^{39}$ are as defined in the context of formulae (FX9) and (FX10). The present invention includes compositions comprising enantiomers, diastereomers and/or ionic forms (e.g., protonated and deprotonated forms) of the compounds of formula (FX11)-(FX20).

In an embodiment of this aspect wherein ring B is a six membered ring, the invention provides compounds for use in a phototherapeutic method being of the formula (FX21), (FX22), or (FX23):

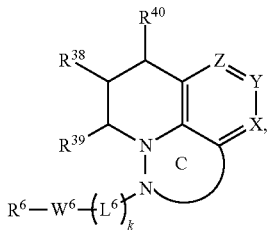
(FX21)

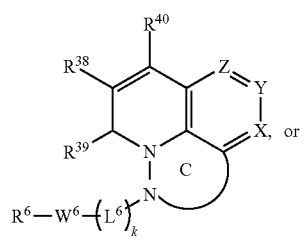
(FX22)

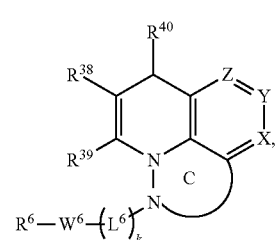
(FX23)

or a pharmaceutically acceptable salt or ester thereof, wherein ring C is defined in the context of formula (FX1), wherein k, $R^6$, $W^6$, $L^6$, X, Y, Z, and $R^{38}$-$R^{39}$ are as defined in the context of formulae (FX9) and (FX10), and wherein $R^{40}$ is hydrogen, $C_1$-$C_{10}$ alkyl, $C_3$-$C_{10}$ cycloalkyl, $C_5$-$C_{10}$ aryl, $C_5$-$C_{10}$ heteroaryl, $C_1$-$C_{10}$ acyl, $C_2$-$C_{10}$ alkenyl, $C_2$-$C_{10}$ alkynyl, $C_5$-$C_{10}$ alkylaryl, $C_1$-$C_6$ alkoxycarbonyl, halo, halomethyl, dihalomethyl, trihalomethyl, —CN, —$CO_2R^{16}$, —$CONR^{17}R^{18}$, —$COR^{19}$, —$NO_2$, —$SOR^{20}$, —$OSR^{21}$, —$SO_2R^{22}$, —$SO_2OR^{23}$, —$SO_2NR^{24}R^{25}$, —$PO_3R^{26}R^{27}$, —$OR^{28}$, —$SR^{29}$, —$NR^{30}R^{31}$, or —$NR^{32}COR^{33}$. The invention of this aspect includes compounds being of the formula (FX24), (FX25), (FX26), (FX27), (FX28), (FX29), (FX30), (FX31), (FX32), (FX33), (FX34), or (FX35):

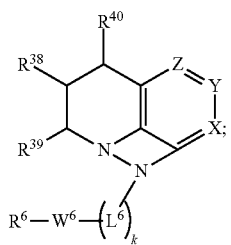
(FX24)

-continued

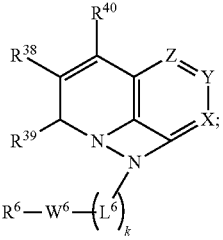
(FX25)

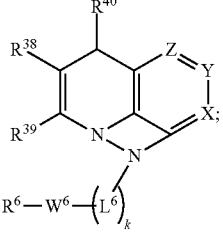
(FX26)

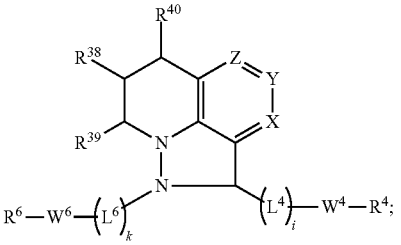
(FX27)

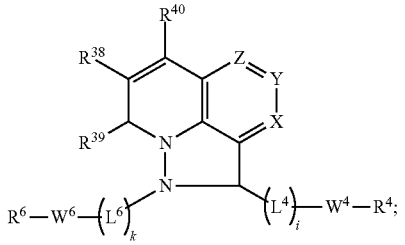
(FX28)

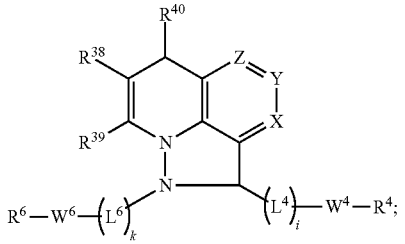
(FX29)

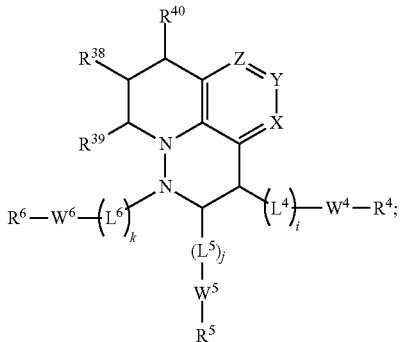
(FX30)

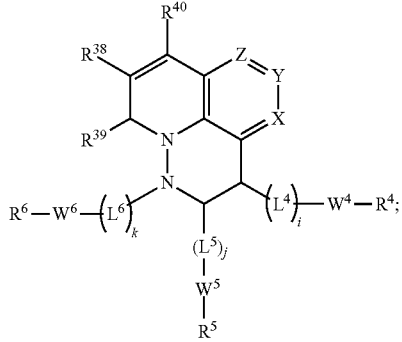

(FX31)

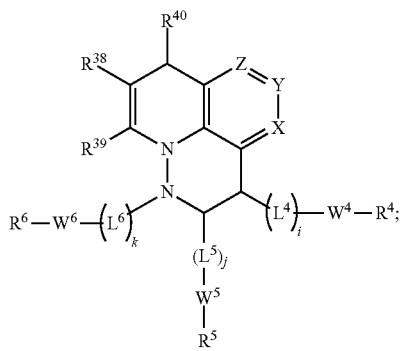

(FX32)

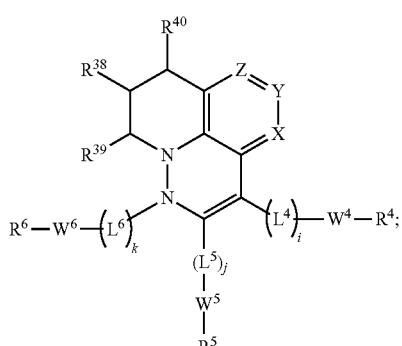

(FX33)

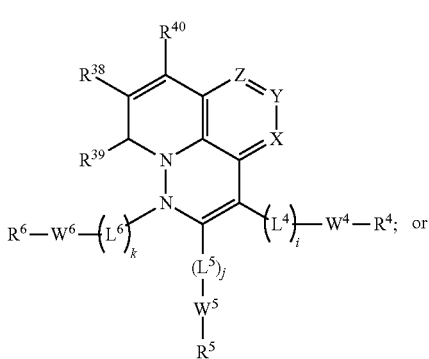

(FX34)

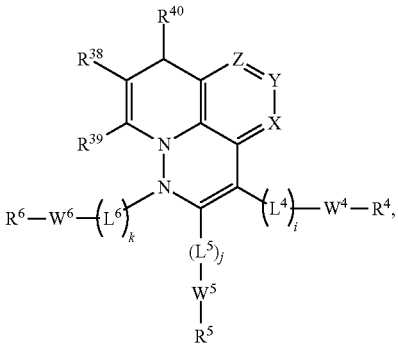

(FX35)

or a pharmaceutically acceptable salt or ester thereof, wherein i, j, k, $R^4$, $R^5$, $R^6$, $W^4$, $W^5$, $W^6$, $L^4$, $L^5$ and $L^6$ are as defined in the context of formula (FX1), and X, Y, Z, and $R^{36}$-$R^{40}$ are as defined in the context of formulae (FX21), (FX22) and (FX23). The present invention includes compositions comprising enantiomers, diastereomers and/or ionic forms (e.g., protonated and deprotonated forms) of the compounds of formula (FX21)-(FX35).

In an embodiment, the invention provides compounds useful as optical agents for phototherapeutic methods having any of formula (FX9)-(FX35), wherein at least one $R^{41}$-$R^{43}$ is an electron withdrawing group and at least one of $R^{41}$-$R^{43}$ is an electron donating group. In an embodiment, the invention provides compounds useful as optical agents for phototherapeutic methods having any of formula (FX9) to (FX35), wherein each of $R^{41}$-$R^{43}$ is independently hydrogen, $C_1$-$C_5$ alkyl, halo, halomethyl, dihalomethyl, trihalomethyl, —CN, —$CO_2R^{16}$, —$CONR^{17}R^{18}$, —$COR^{19}$, —$NO_2$, —$SOR^{20}$, —$OSR^{21}$, —$SO_2R^{22}$, —$SO_2OR^{23}$, —$SO_2NR^{24}R^{25}$, —$PO_3R^{26}R^{27}$, —$OR^{28}$, —$SR^{29}$, —$NR^{30}R^{31}$, or —$NR^{32}COR^{33}$. In an embodiment, the invention provides compounds useful as optical agents for phototherapeutic methods having any of formula (FX9) to (FX35), wherein at least one of $R^{41}$-$R^{43}$ is —$NR^{30}R^{31}$, —$OR^{28}$, —$NR^{32}COR^{33}$ or —$SR^{29}$. In an embodiment, the invention provides compounds useful as optical agents for phototherapeutic methods having any of formula (FX9) to (FX35), wherein at least one of $R^{41}$-$R^{43}$—CN, —$COR^{19}$, —$CONR^{17}R^{18}$, —$NO_2$, —$SO_2R^{22}$, or —$SO_2NR^{24}R^{25}$. In an embodiment, the invention provides compounds useful as optical agents for phototherapeutic methods having any of formula (FX9) to (FX35), wherein at least one of $R^{41}$-$R^{43}$ is —$NR^{30}R^{31}$; and wherein each of $R^{30}$ and $R^{31}$ is independently hydrogen or $C_1$-$C_5$ alkyl. In an embodiment, the invention provides compounds useful as optical agents for phototherapeutic methods having any of formula (FX9) to (FX35), wherein at least one of $R^{41}$-$R^{43}$ is —$SO_2R^{22}$, or —$SO_2NR^{24}R^{25}$; and wherein each of $R^{22}$, $R^{24}$ and $R^{25}$ is independently hydrogen or $C_1$-$C_5$ alkyl. In an embodiment, the invention provides compounds useful as optical agents for phototherapeutic methods having any of formula (FX9) to (FX35), wherein at least one of $R^{41}$-$R^{43}$ is —$NR^{30}R^{31}$, wherein at least one of $R^{41}$-$R^{43}$ is —$SO_2R^{22}$, or —$SO_2NR^{24}R^{25}$; and wherein each of $R^{22}$, $R^{24}$, $R^{25}$, $R^{30}$, $R^{31}$ is independently hydrogen or $C_1$-$C_5$ alkyl.

In an embodiment, provided are compounds of formula (FX9)-(FX35) wherein:

(a) any one of $R^{41}$ and $R^{42}$ is $C_1$-$C_6$ alkyl, —$OR^{46}$, —$SR^{47}$, —$NR^{48}R^{49}$, or —$NR^{50}COR^{51}$; and the other of $R^{41}$ and $R^{42}$ is —CN, —$CO_2R^{44}$, —$SO_2OR^{60}$, —$CONR^{52}R^{53}$, —COR$^{54}$, —NO$_2$, —SOR$^{45}$, —SO$_2$R$^{55}$, —PO$_3$R$^{56}$R$^{57}$, halo, C$_1$-C$_6$ acyl, trihalomethyl, or —SO$_2$NR$^{58}$R$^{59}$;

(b) any one of R$^{41}$ and R$^{43}$ is C$_1$-C$_6$ alkyl, —OR$^{46}$, —SR$^{47}$, —NR$^{48}$R$^{49}$, or —NR$^{50}$COR$^{51}$; and the other of R$^{41}$ and R$^{43}$ is —CN, —CO$_2$R$^{44}$, —SO$_2$OR$^{60}$, —CONR$^{52}$R$^{53}$, —COR$^{54}$, —NO$_2$, —SOR$^{45}$, —SO$_2$R$^{55}$, —PO$_3$R$^{56}$R$^{57}$, halo, C$_1$-C$_6$ acyl, trihalomethyl, or —SO$_2$NR$^{58}$R$^{59}$;

(c) any one of R$^{42}$ and R$^{43}$ is C$_1$-C$_6$ alkyl, —OR$^{46}$, —SR$^{47}$, —NR$^{48}$R$^{49}$, or —NR$^{50}$COR$^{51}$; and the other of R$^{42}$ and R$^{43}$ is —CN, —CO$_2$R$^{44}$, —SO$_2$OR$^{60}$, —CONR$^{52}$R$^{53}$, —COR$^{54}$, —NO$_2$, —SOR$^{45}$, —SO$_2$R$^{55}$, —PO$_3$R$^{56}$R$^{57}$, halo, C$_1$-C$_6$ acyl, trihalomethyl, or —SO$_2$NR$^{58}$R$^{59}$;

(d) any two of R$^{41}$, R$^{42}$ and R$^{43}$ is C$_1$-C$_6$ alkyl, —OR$^{46}$, —SR$^{47}$, —NR$^{48}$R$^{49}$, or —NR$^{50}$COR$^{51}$; and the other of R$^{41}$, R$^{42}$ and R$^{43}$ is —CN, —CO$_2$R$^{44}$, —SO$_2$OR$^{60}$, —CONR$^{52}$R$^{53}$, —COR$^{54}$, —NO$_2$, —SOR$^{45}$, —SO$_2$R$^{55}$, —PO$_3$R$^{56}$R$^{57}$, halo, C$_1$-C$_6$ acyl, trihalomethyl, or —SO$_2$NR$^{58}$R$^{59}$; or (e) any two of R$^{41}$, R$^{42}$ and R$^{43}$ is —CN, —CO$_2$R$^{44}$, —SO$_2$OR$^{60}$, —CONR$^{52}$R$^{53}$, —COR$^{54}$, —NO$_2$, —SOR$^{45}$, —SO$_2$R$^{55}$, —PO$_3$R$^{56}$R$^{57}$, halo, C$_1$-C$_6$ acyl, trihalomethyl, or —SO$_2$NR$^{58}$R$^{59}$;

wherein in this embodiment each of R$^{44}$-R$^{60}$ is independently hydrogen, C$_1$-C$_{20}$ alkyl, C$_5$-C$_{30}$ aryl or C$_5$-C$_{30}$ heteroaryl.

The invention includes therapeutic agents for biomedical applications, including phototherapy, comprising purified stereoisomers (e.g., enantiomers and diastereomers), tautomers (diaza and azo tautomers), salts (including quarternary salts), and/or ionic forms (e.g., protonated and deprotonated forms) of the compounds of any of formula (FX1)-(FX41), and mixtures thereof. As will be understood by those having general skill in the art, acidic functional groups and basic functional groups of the compounds of any of formula (FX1)-(FX41) may be in protonated or deprotonated states depending on the molecular environment (e.g., pH, ionic strength, composition, etc.), for example during synthesis, formulation and/or administration.

In an embodiment, the invention includes optical agents having formula (FX1), wherein at least two of R$^1$-R$^6$, along with any of W$^1$-W$^6$ and L$^1$-L$^6$, if present, combine to form one or more alicyclic or aromatic, carbocyclic or heterocyclic 5 or 6 membered rings. In the context of the present description, the expression "combine to form one or more alicyclic or aromatic, carbocyclic or heterocyclic 5 or 6 membered rings" refers to compounds wherein at least two of R$^1$-R$^6$, for example neighboring R$^1$-R$^6$ groups, are covalently bonded to each other, thereby resulting in formation of one or more ring structures, for example, 5 or 6 membered ring structures fused to the central diaza ring of formula (FX1). In an embodiment, for example, at least two of R$^1$-R$^6$, for example neighboring R$^1$-R$^6$ groups, are covalently bonded to form one or more alicyclic, carbocyclic or heterocyclic 5 or 6 membered ring structures fused to the central diaza backbone of formula (FX1), such as a C$_3$-C$_{30}$ cycloalkyl, optionally a C$_3$-C$_{20}$ cycloalkyl, or optionally a C$_3$-C$_{10}$ cycloalkyl. In an embodiment, for example, at least two of R$^1$-R$^6$, for example neighboring R$^1$-R$^6$ groups, are covalently bonded to form one or more aromatic, carbocyclic or heterocyclic 5 or 6 membered ring structures fused to the central diaza backbone of formula (FX1), such as a C$_5$-C$_{30}$ aryl or C$_5$-C$_{30}$ heteroaryl, optionally a C$_5$-C$_{20}$ aryl or C$_5$-C$_{20}$ heteroaryl, or optionally a C$_5$-C$_{10}$ aryl or C$_5$-C$_{10}$ heteroaryl.

In an embodiment, for example, the invention includes optical agents having formula (FX1), wherein at least two of R$^1$-R$^6$, for example neighboring R$^1$-R$^6$ groups, combine via a covalent bond, thereby resulting in formation of a group corresponding to benzene, naphthalene, naphthoquinone, diphenylmethane, fluorene, anthracene, anthraquinone, phenanthrene, tetracene, naphthacenedione, pyridine, quinoline, isoquinoline, indole, isoindole, pyrrole, imidazole, oxazole, thiazole, pyrazole, pyrazine, pyrimidine, purine, benzimidazole, furan, benzofuran, dibenzofuran, carbazole, acridine, acridone, phenanthridine, thiophene, benzothiophene, dibenzothiophene, xanthene, xanthone, flavone, coumarin, azulene or anthracycline, for example, fused to the central diaza backbone of formula (FX1).

In an embodiment, R$^1$, R$^2$, W$^1$, and W$^2$, and L$^1$ and L$^2$, if present, combine to form a group covalently linked to the central diaza backbone of formula (FX1), via two covalent bonds, wherein the group is —CH$_2$CH$_2$CH$_2$CH$_2$— or —CH$_2$CH$_2$CH$_2$—, wherein optionally any —CH$_2$— can be replaced by —NH—, —S—, or —O—, thereby resulting in a compound having an alicyclic, carbocyclic or heterocyclic 5 or 6 membered ring fused to the central diaza ring. In an embodiment, for example, R$^1$, R$^2$, W$^1$, and W$^2$, and L$^1$ and L$^2$, if present, combine to form a group covalently linked to the central diaza backbone of formula (FX1), via two covalent bonds, wherein the group is —CH$_2$CH$_2$CH$_2$CH$_2$—, —NHCH$_2$CH$_2$CH$_2$—, —CH$_2$NHCH$_2$CH$_2$—, —CH$_2$CH$_2$NHCH$_2$—, —CH$_2$CH$_2$CH$_2$NH—, —OCH$_2$CH$_2$CH$_2$—, —CH$_2$OCH$_2$CH$_2$—, —CH$_2$CH$_2$OCH$_2$—, —CH$_2$CH$_2$CH$_2$O—, —SCH$_2$CH$_2$CH$_2$—, —CH$_2$SCH$_2$CH$_2$—, —CH$_2$CH$_2$SCH$_2$—, —CH$_2$CH$_2$CH$_2$S—, —CH$_2$CH$_2$CH$_2$—, —NHCH$_2$CH$_2$—, —CH$_2$NHCH$_2$—, —CH$_2$CH$_2$NH—, —OCH$_2$CH$_2$—, —CH$_2$OCH$_2$—, —CH$_2$CH$_2$O—, —SCH$_2$CH$_2$—, —CH$_2$SCH$_2$—, or —CH$_2$CH$_2$S—.

In an embodiment, R$^1$, R$^6$, W$^1$, and W$^6$, and L$^1$ and L$^6$, if present, combine to form a group covalently linked to the central diaza backbone of formula (FX1), via two covalent bonds, wherein the group is —CH$_2$CH$_2$CH$_2$CH$_2$— or —CH$_2$CH$_2$CH$_2$—, wherein optionally any —CH$_2$— can be replaced by —NH—, —S—, or —O—, thereby resulting in a compound having an alicyclic, carbocyclic or heterocyclic 5 or 6 membered ring fused to the central diaza ring. In an embodiment, for example, R$^1$, R$^6$, W$^1$, and W$^6$, and L$^1$ and L$^6$, if present, combine to form a group covalently linked to the central diaza backbone of formula (FX1), via two covalent bonds, wherein the group is —CH$_2$CH$_2$CH$_2$CH$_2$—, —NHCH$_2$CH$_2$CH$_2$—, —CH$_2$NHCH$_2$CH$_2$—, —CH$_2$CH$_2$NHCH$_2$—, —CH$_2$CH$_2$CH$_2$NH—, —OCH$_2$CH$_2$CH$_2$—, —CH$_2$OCH$_2$CH$_2$—, —CH$_2$CH$_2$OCH$_2$—, —CH$_2$CH$_2$CH$_2$O—, —SCH$_2$CH$_2$CH$_2$—, —CH$_2$SCH$_2$CH$_2$—, —CH$_2$CH$_2$SCH$_2$—, —CH$_2$CH$_2$CH$_2$S—, —CH$_2$CH$_2$CH$_2$—, —NHCH$_2$CH$_2$—, —CH$_2$NHCH$_2$—, —CH$_2$CH$_2$NH—, —OCH$_2$CH$_2$—, —CH$_2$OCH$_2$—, —CH$_2$CH$_2$O—, —SCH$_2$CH$_2$—, —CH$_2$SCH$_2$—, or —CH$_2$CH$_2$S—.

In an embodiment, R$^2$, R$^3$, W$^2$, and W$^3$, and L$^2$ and L$^3$, if present, combine to form a group covalently linked to the central diaza backbone of formula (FX1), via two covalent bonds, wherein the group is —CH$_2$CH$_2$CH$_2$CH$_2$— or —CH$_2$CH$_2$CH$_2$—, wherein optionally any —CH$_2$— can be replaced by —NH—, —S—, or —O—, thereby resulting in a compound having an alicyclic, carbocyclic or heterocyclic 5 or 6 membered ring fused to the central diaza ring. In an embodiment, for example, R$^2$, R$^3$, W$^2$, and W$^3$, and L$^2$ and L$^3$, if present, combine to form a group covalently linked to the central diaza backbone of formula (FX1), via two covalent bonds, wherein the group is —CH$_2$CH$_2$CH$_2$CH$_2$—, —NHCH$_2$CH$_2$CH$_2$—, —CH$_2$NHCH$_2$CH$_2$—, —CH$_2$CH$_2$NHCH$_2$—, —CH$_2$CH$_2$CH$_2$NH—, —OCH$_2$CH$_2$CH$_2$—, —CH$_2$OCH$_2$CH$_2$—, —CH$_2$CH$_2$OCH$_2$—, —CH$_2$CH$_2$CH$_2$O—, —SCH$_2$CH$_2$CH$_2$—, —CH$_2$SCH$_2$CH$_2$—, —CH$_2$CH$_2$SCH$_2$—, —CH$_2$CH$_2$CH$_2$S—, —CH$_2$CH$_2$CH$_2$—, —NHCH$_2$CH$_2$—, —CH$_2$NHCH$_2$—, —CH$_2$CH$_2$NH—, —OCH$_2$CH$_2$—, —CH$_2$OCH$_2$—, —CH$_2$CH$_2$O—, —SCH$_2$CH$_2$—, —CH$_2$SCH$_2$—, or —CH$_2$CH$_2$S—, thereby resulting in a compound having a alicyclic, carbocyclic or heterocyclic 5 or 6 membered ring fused to the central diaza ring.

In an embodiment, $R^2$, $R^3$, $W^2$, and $W^3$, and $L^2$ and $L^3$, if present, combine to form a group covalently linked to the central diaza backbone of formula (FX1), via two covalent bonds, wherein the group is a aromatic, carbocyclic or heterocyclic 5 or 6 membered ring fused to the central diaza ring. In an embodiment, for example, $R^2$, $R^3$, $W^2$, and $W^3$, and $L^2$ and $L^3$, if present, combine to form a group covalently linked to the central diaza backbone of formula (FX1), via two covalent bonds, wherein the group is —CHCHCHCH—, —NCHCHCH—, —CHNCHCH—, —CHCHNCH—, —CHCHCHN—, —NNCHCH—, —NCHNCH—, —NCHCHN—, —CHNNCH—, —CHCHNN—, —CHNCHN—, —CHOCH—, —CHNCH— or —CHSCH—, thereby resulting in a compound having an aromatic, carbocyclic or heterocyclic 5 or 6 membered ring fused to the central diaza ring. In an embodiment, for example, $R^2$, $R^3$, $W^2$, and $W^3$, and $L^2$ and $L^3$, if present, combine to form a group covalently linked to the central diaza backbone of formula (FX1), via two covalent bonds, wherein the group is —(CH$_2$)$_p$—, —(CH$_2$)$_q$R(CH$_2$)$_r$—, —C(R$^{45}$)=C(R$^{46}$)—C(R$^{47}$)=C(R$^{48}$)—, —N=C(R$^{49}$)—C(R$^{50}$)=C(R$^{51}$)—, —C(R$^{52}$)=N—C(R$^{53}$)=C(R$^{54}$)—, —C(R$^{55}$)=C(R$^{56}$)—N=C(R$^{57}$)—, —C(R$^{58}$)=C(R$^{59}$)—C(R$^{60}$)=N—, —C(R$^{61}$)=C(R$^{52}$)—N(R$^{63}$)—, —C(R$^{64}$)=C(R$^{65}$)—O—, —C(R$^{66}$)=C(R$^{67}$)—S—, —N=C(R$^{68}$)—N(R$^{69}$)—, —N=C(R$^{70}$)—O—, —N=C(R$^{71}$)—S—, —C(R$^{72}$)=N—N(R$^{73}$)—, —C(R$^{74}$)=N—N(R$^{75}$)—, —C(R$^{76}$)=N—O—, —N=N—N(R$^{77}$)—, —N=N—O—, or —N=N—S—; wherein p is 1, 2, 3, 4, or 5, each of q and r is independently 0, 1, 2, or 3, and wherein the sum of q and r is 2, 3, 4, 5, or 6; and wherein R is —O—, —N(R$^{78}$)—, —S—, —SO— or —SO$_2$—; wherein each of R$^{45}$-R$^{78}$ is independently hydrogen, $C_1$-$C_{10}$ alkyl, $C_5$-$C_{10}$ aryl or $C_5$-$C_{10}$ heteroaryl.

In an embodiment, $R^3$, $R^4$, $W^3$, and $W^4$, and $L^3$ and $L^4$, if present, combine to form a group covalently linked to the central diaza backbone of formula (FX1), via two covalent bonds, wherein the group is —CH$_2$CH$_2$CH$_2$CH$_2$— or —CH$_2$CH$_2$CH$_2$—, wherein optionally any —CH$_2$— can be replaced by —NH—, —S—, or —O—, thereby resulting in a compound having an alicyclic, carbocyclic or heterocyclic 5 or 6 membered ring fused to the central diaza ring. In an embodiment, for example, $R^3$, $R^4$, $W^3$, and $W^4$, and $L^3$ and $L^4$, if present, combine to form a group covalently linked to the central diaza backbone of formula (FX1), via two covalent bonds, wherein the group is —CH$_2$CH$_2$CH$_2$CH$_2$—, —NHCH$_2$CH$_2$CH$_2$—, —CH$_2$NHCH$_2$CH$_2$—, —CH$_2$CH$_2$NHCH$_2$—, —CH$_2$CH$_2$CH$_2$NH—, —OCH$_2$CH$_2$CH$_2$—, —CH$_2$OCH$_2$CH$_2$—, —CH$_2$CH$_2$OCH$_2$—, —CH$_2$CH$_2$CH$_2$O—, —SCH$_2$CH$_2$CH$_2$—, —CH$_2$SCH$_2$CH$_2$—, —CH$_2$CH$_2$SCH$_2$—, —CH$_2$CH$_2$CH$_2$S—, —CH$_2$CH$_2$CH$_2$—, —NHCH$_2$CH$_2$—, —CH$_2$NHCH$_2$—, —CH$_2$CH$_2$NH—, —OCH$_2$CH$_2$—, —CH$_2$OCH$_2$—, —CH$_2$CH$_2$O—, —SCH$_2$CH$_2$—, —CH$_2$SCH$_2$—, or —CH$_2$CH$_2$S—, thereby resulting in a compound having an alicyclic, carbocyclic or heterocyclic 5 or 6 membered ring fused to the central diaza ring.

In an embodiment, $R^3$, $R^4$, $W^3$, and $W^4$, and $L^3$ and $L^4$, if present, combine to form a group covalently linked to the central diaza backbone of formula (FX1), via two covalent bonds, wherein the group is an aromatic, carbocyclic or heterocyclic 5 or 6 membered ring fused to the central diaza ring. In an embodiment, for example, $R^3$, $R^4$, $W^3$, and $W^4$, and $L^3$ and $L^4$, if present, combine to form a group covalently linked to the central diaza backbone of formula (FX1), via two covalent bonds, wherein the group is —CHCHCHCH—, —NCHCHCH—, —CHNCHCH—, —CHCHNCH—, —CHCHCHN—, —NNCHCH—, —NCHNCH—, —NCHCHN—, —CHNNCH—, —CHCHNN—, —CHNCHN—, —CHOCH—, —CHNCH— or —CHSCH—, thereby resulting in a compound having an aromatic, carbocyclic or heterocyclic 5 or 6 membered ring fused to the central diaza ring. In an embodiment, for example, $R^3$, $R^4$, $W^3$, and $W^4$, and $L^3$ and $L^4$, if present, combine to form a group covalently linked to the central diaza backbone of formula (FX1), via two covalent bonds, wherein the group is —(CH$_2$)$_p$—, —(CH$_2$)$_q$R(CH$_2$)$_r$—, —C(R$^{45}$)=C(R$^{46}$)—C(R$^{47}$)=C(R$^{48}$)—, —N=C(R$^{49}$)—C(R$^{50}$)=C(R$^{51}$)—, —C(R$^{52}$)=N—C(R$^{53}$)=C(R$^{54}$)—, —C(R$^{55}$)=C(R$^{56}$)—N=C(R$^{57}$)—, —C(R$^{58}$)=C(R$^{59}$)—C(R$^{60}$)=N—, —C(R$^{61}$)=C(R$^{52}$)—N(R$^{63}$)—, —C(R$^{64}$)=C(R$^{65}$)—O—, —C(R$^{66}$)=C(R$^{67}$)—S—, —N=C(R$^{68}$)—N(R$^{69}$)—, —N=C(R$^{70}$)—O—, —N=C(R$^{71}$)—S—, —C(R$^{72}$)=N—N(R$^{73}$)—, —C(R$^{74}$)=N—N(R$^{75}$)—, —C(R$^{76}$)=N—O—, —N=N—N(R$^{77}$)—, —N=N—O—, or —N=N—S—; wherein p is 1, 2, 3, 4, or 5, each of q and r is independently 0, 1, 2, or 3, and wherein the sum of q and r is 2, 3, 4, 5, or 6; and wherein R is —O—, —N(R$^{78}$)—, —S—, —SO— or —SO$_2$—; wherein each of R$^{45}$-R$^{78}$ is independently hydrogen, $C_1$-$C_{10}$ alkyl, $C_5$-$C_{10}$ aryl or $C_5$-$C_{10}$ heteroaryl.

In an embodiment, $R^4$, $R^5$, $W^4$, and $W^5$, and $L^4$ and $L^5$, if present, combine to form a group covalently linked to the central diaza backbone of formula (FX1), via two covalent bonds, wherein the group is —CH$_2$CH$_2$CH$_2$CH$_2$— or —CH$_2$CH$_2$CH$_2$—, wherein optionally any —CH$_2$— can be replaced by —NH—, —S—, or —O—, thereby resulting in a compound having an alicyclic, carbocyclic or heterocyclic 5 or 6 membered ring fused to the central diaza ring. In an embodiment, for example, $R^4$, $R^5$, $W^4$, and $W^5$, and $L^4$ and $L^5$, if present, combine to form a group covalently linked to the central diaza backbone of formula (FX1), via two covalent bonds, wherein the group is —CH$_2$CH$_2$CH$_2$CH$_2$—, —NHCH$_2$CH$_2$CH$_2$—, —CH$_2$NHCH$_2$CH$_2$—, —CH$_2$CH$_2$NHCH$_2$—, —CH$_2$CH$_2$CH$_2$NH—, —OCH$_2$CH$_2$CH$_2$—, —CH$_2$OCH$_2$CH$_2$—, —CH$_2$CH$_2$OCH$_2$—, —CH$_2$CH$_2$CH$_2$O—, —SCH$_2$CH$_2$CH$_2$—, —CH$_2$SCH$_2$CH$_2$—, —CH$_2$CH$_2$SCH$_2$—, —CH$_2$CH$_2$CH$_2$S—, —CH$_2$CH$_2$CH$_2$—, —NHCH$_2$CH$_2$—, —CH$_2$NHCH$_2$—, —CH$_2$CH$_2$NH—, —OCH$_2$CH$_2$—, —CH$_2$OCH$_2$—, —CH$_2$CH$_2$O—, —SCH$_2$CH$_2$—, —CH$_2$SCH$_2$—, or —CH$_2$CH$_2$S—, thereby resulting in a compound having an alicyclic, carbocyclic or heterocyclic 5 or 6 membered ring fused to the central diaza ring.

In an embodiment, $R^4$, $R^5$, $W^4$, and $W^5$, and $L^4$ and $L^5$, if present, combine to form a group covalently linked to the central diaza backbone of formula (FX1), via two covalent bonds, wherein the group is an aromatic, carbocyclic or heterocyclic 5 or 6 membered ring fused to the central diaza ring. In an embodiment, for example, $R^4$, $R^5$, $W^4$, and $W^5$, and $L^4$ and $L^5$, if present, combine to form a group covalently linked to the central diaza backbone of formula (FX1), via two covalent bonds, wherein the group is —CHCHCHCH—, —NCHCHCH—, —CHNCHCH—, —CHCHNCH—, —CHCHCHN—, —NNCHCH—, —NCHNCH—, —NCHCHN—, —CHNNCH—, —CHCHNN—, —CHNCHN—, —CHOCH—, —CHNCH— or —CHSCH—, thereby resulting in a compound having an aromatic, carbocyclic or heterocyclic 5 or 6 membered ring fused to the central diaza ring. In an embodiment, for example, $R^4$, $R^5$, $W^4$, and $W^5$, and $L^4$ and $L^5$, if present, combine to form a group covalently linked to the central diaza backbone of formula (FX1), via two covalent bonds, wherein the group is —$(CH_2)_p$—, —$(CH_2)_qR(CH_2)_r$—, —$C(R^{45})$=C$(R^{46})$—$C(R^{47})$=C$(R^{48})$—, —N=$C(R^{49})$—$C(R^{50})$=C$(R^{51})$—, —$C(R^{52})$=N—$C(R^{53})$=C$(R^{54})$—, —$C(R^{55})$=C$(R^{56})$—N=$C(R^{57})$—, —$C(R^{58})$=C$(R^{59})$—$C(R^{60})$=N—, —$C(R^{61})$=$C(R^{52})$—$N(R^{63})$—, —$C(R^{64})$=$C(R^{65})$—O—, —$C(R^{66})$=$C(R^{67})$—S—, —N=$C(R^{68})$—$N(R^{69})$—, —N=$C(R^{70})$—O—, —N=$C(R^{71})$—S—, —$C(R^{72})$=N—$N(R^{73})$—, —$C(R^{74})$=N—$N(R^{75})$—, —$C(R^{76})$=N—O—, —N=N—$N(R^{77})$—, —N=N—O—, or —N=N—S—; wherein p is 1, 2, 3, 4, or 5, each of q and r is independently 0, 1, 2, or 3, and wherein the sum of q and r is 2, 3, 4, 5, or 6; and wherein R is —O—, —$N(R^{78})$—, —S—, —SO— or —$SO_2$—; wherein each of $R^{45}$-$R^{78}$ is independently hydrogen, $C_1$-$C_{10}$ alkyl, $C_5$-$C_{10}$ aryl or $C_5$-$C_{10}$ heteroaryl.

In an embodiment, $R^6$, $R^5$, $W^6$, and $W^5$, and $L^6$ and $L^5$, if present, combine to form a group covalently linked to the central diaza backbone of formula (FX1), via two covalent bonds, wherein the group is —$CH_2CH_2CH_2CH_2$— or —$CH_2CH_2CH_2$—, wherein optionally any —$CH_2$— can be replaced by —NH—, —S—, or —O—, thereby resulting in a compound having an alicyclic, carbocyclic or heterocyclic 5 or 6 membered ring fused to the central diaza ring. In an embodiment, for example, $R^6$, $R^5$, $W^6$, and $W^5$, and $L^6$ and $L^5$, if present, combine to form a group covalently linked to the central diaza backbone of formula (FX1), via two covalent bonds, wherein the group is —$CH_2CH_2CH_2CH_2$—, —$NHCH_2CH_2CH_2$—, —$CH_2NHCH_2CH_2$—, —$CH_2CH_2NHCH_2$—, —$CH_2CH_2CH_2NH$—, —$OCH_2CH_2CH_2$—, —$CH_2OCH_2CH_2$—, —$CH_2CH_2OCH_2$—, —$CH_2CH_2CH_2O$—, —$SCH_2CH_2CH_2$—, —$CH_2SCH_2CH_2$—, —$CH_2CH_2SCH_2$—, —$CH_2CH_2CH_2S$—, —$CH_2CH_2CH_2$—, —$NHCH_2CH_2$—, —$CH_2NHCH_2$—, —$CH_2CH_2NH$—, —$OCH_2CH_2$—, —$CH_2OCH_2$—, —$CH_2CH_2O$—, —$SCH_2CH_2$—, —$CH_2SCH_2$—, or —$CH_2CH_2S$—, thereby resulting in a compound having an alicyclic, carbocyclic or heterocyclic 5 or 6 membered ring fused to the central diaza ring.

In an embodiment, $R^6$, $R^5$, $W^6$, and $W^5$, and $L^6$ and $L^5$, if present, if present, combine to form a group covalently linked to the central diaza backbone of formula (FX1), via two covalent bonds, wherein the group is an aromatic, carbocyclic or heterocyclic 5 or 6 membered ring fused to the central diaza ring. In an embodiment, for example, $R^6$, $R^5$, $W^6$, and $W^5$, and $L^6$ and $L^5$, if present, combine to form a group covalently linked to the central diaza backbone of formula (FX1), via two covalent bonds, wherein the group is —CHCHCHCH—, —NCHCHCH—, —CHNCHCH—, —CHCHNCH—, —CHCHCHN—, —NNCHCH—, —NCHNCH—, —NCHCHN—, —CHNNCH—, —CHCHNN—, —CHNCHN—, —CHOCH—, —CHNCH— or —CHSCH—, thereby resulting in a compound having an aromatic, carbocyclic or heterocyclic 5 or 6 membered ring fused to the central diaza ring. In an embodiment, for example, $R^4$, $R^5$, $W^4$, and $W^5$, and $L^4$ and $L^5$, if present, combine to form a group covalently linked to the central diaza backbone of formula (FX1), via two covalent bonds, wherein the group is —$(CH_2)_p$—, —$(CH_2)_qR(CH_2)_r$—, —$C(R^{45})$=C$(R^{46})$—$C(R^{47})$=C$(R^{48})$—, —N=$C(R^{49})$—$C(R^{50})$=C$(R^{51})$—, —$C(R^{52})$=N—$C(R^{53})$=C$(R^{54})$—, —$C(R^{55})$=C$(R^{56})$—N=$C(R^{57})$—, —$C(R^{58})$=C$(R^{59})$—$C(R^{60})$=N—, —$C(R^{61})$=$C(R^{52})$—$N(R^{63})$—, —$C(R^{64})$=$C(R^{65})$—O—, —$C(R^{66})$=$C(R^{67})$—S—, —N=$C(R^{68})$—$N(R^{69})$—, —N=$C(R^{70})$—O—, —N=$C(R^{71})$—S—, —$C(R^{72})$=N—$N(R^{73})$—, —$C(R^{74})$=N—$N(R^{75})$—, —$C(R^{76})$=N—O—, —N=N—$N(R^{77})$—, —N=N—O—, or —N=N—S—; wherein p is 1, 2, 3, 4, or 5, each of q and r is independently 0, 1, 2, or 3, and wherein the sum of q and r is 2, 3, 4, 5, or 6; and wherein R is —O—, —$N(R^{78})$—, —S—, —SO— or —$SO_2$—; wherein each of $R^{45}$-$R^{78}$ is independently hydrogen, $C_1$-$C_{10}$ alkyl, $C_5$-$C_{10}$ aryl or $C_5$-$C_{10}$ heteroaryl.

The invention provides compounds of any one of formula (FX1)-(FX35) and (FX38), wherein at least one of $R^1$-$R^6$ and $R^{38}$-$R^{43}$ is independently, or at least two or more of $R^1$-$R^6$ combine to form, a group comprising one or more aromatic rings or heterocyclic aromatic rings, optionally two or more fused aromatic rings and/or heterocyclic aromatic rings. In an embodiment, for example, the invention provides compounds of any one of formula (FX1)-(FX35) and (FX38), wherein at least one of $R^1$-$R^6$ and $R^{38}$-$R^{43}$ is independently, or at least two or more of $R^1$-$R^6$ combine to form, a group corresponding to benzene, naphthalene, naphthoquinone, diphenylmethane, fluorene, anthracene, anthraquinone, phenanthrene, tetracene, naphthacenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline, optionally having one or more electron donating groups, electron withdrawing groups, or targeting ligands provided as one or more substituents. In an embodiment, the invention provides a compound for use in a phototherapy procedure having any one of formula (FX1) to (FX35) and (FX38); wherein at least one of $R^1$-$R^6$ and $R^{38}$-$R^{43}$ is independently, or at least two or more of $R^1$-$R^6$ combine to form, benzene or a derivative thereof. In an embodiment, the invention provides a compound for use in a phototherapy procedure having any one of formula (FX1) to (FX35) and (FX38); wherein at least one of $R^1$-$R^6$ and $R^{38}$-$R^{43}$ is independently, or at least two or more of $R^1$-$R^6$ combine to form, a polycyclic aromatic group corresponding to naphthalene, diphenylmethane, fluorene, anthracene, phenanthrene, tetracene, naphthoquinone, anthraquinone, naphthacenedione, azulene, or anthracycline. In an embodiment, the invention provides a compound for use in a phototherapy procedure having any one of formula (FX1) to (FX35) and (FX38); wherein at least one of $R^1$-$R^6$ and $R^{36}$-$R^{43}$ is independently, or at least two or more of $R^1$-$R^6$ combine to form, a heterocyclic aromatic group having a six member nitrogen-containing ring, wherein the heterocyclic aromatic group corresponds to pyridine, pyrimidine, pyrazine, quinoline, isoquinoline, purine, acridine, acridone, or phenanthridine. In an embodiment, the invention provides a compound for use in a phototherapy procedure having any one of formula (FX1) to (FX35) and (FX38); wherein at least one of $R^1$-$R^6$ and $R^{38}$-$R^{43}$ is independently, or at least two or more of $R^1$-$R^6$ combine to form, a heterocyclic aromatic group having a five member nitrogen-containing ring, wherein the heterocyclic aromatic group corresponds to pyrrole, pyrazole, indole, isoindole, imidazole, oxazole, thiazole, purine, benzimidazole, or carbazole. In an embodiment, the invention provides a compound for use in a phototherapy procedure having any one of formula (FX1) to (FX35) and (FX38); wherein at least one of $R^1$-$R^6$ and $R^{38}$-$R^{43}$ is independently, or at least two or more of $R^1$-$R^6$ combine to form, a heterocyclic aromatic group having a five or six member oxygen-containing ring, wherein the heterocyclic aromatic group corresponds to furan, oxazole, benzofuran, dibenzofuran, xanthene, xanthone, flavone, or coumarin. In an embodiment, the invention provides a compound for use in a phototherapy procedure having any one of formula (FX1) to (FX35) and (FX38); wherein at least one of $R^1$-$R^6$ and $R^{38}$-$R^{43}$ is independently, or at least two or more of $R^1$-$R^6$ combine to form, a heterocyclic aromatic group having a five member sulfur-containing ring, wherein the heterocyclic aromatic group corresponds to thiophene, thiazole, benzothiophene, or dibenzothiophene.

The invention includes compounds of any one of formula (FX1)-(FX35) and (FX38), wherein at least one of $R^1$-$R^6$ and $R^{38}$-$R^{43}$ is independently, or at least two or more of $R^1$-$R^6$ combine to form, a dye. As used herein, the term "dye" refers to a functional group providing a chromophore and/or fluorophore capable of excitation upon exposure to electromagnetic radiation having wavelengths over the range of 350 nm to 1300 nanometers, and optionally wavelengths selected over the range of 350 nm to 900 nanometers. In an embodiment, for example, the any one of formula (FX1)-(FX35) and (FX38), wherein at least one of $R^1$-$R^6$ and $R^{38}$-$R^{43}$ is independently, a aromatic or heteroaromatic dye, such as a $C_5$-$C_{30}$ aryl or $C_5$-$C_{30}$ heteroaryl chromophore or fluorophore, optionally a $C_5$-$C_{20}$ aryl or $C_5$-$C_{20}$ heteroaryl chromophore or fluorophore and/or $C_5$-$C_{10}$ aryl or $C_5$-$C_{10}$ heteroaryl chromophore or fluorophore. Compounds of this aspect of the present invention include bifunctional optical agents, capable of providing tandem photosensitizer and imaging functionality. In an embodiment, for example, the invention provides a compound having any one of formula (FX1)-(FX35) and (FX38) that functions as a photosensitizer upon exposure to electromagnetic radiation having a first distribution of wavelengths, and wherein at least one of $R^1$-$R^6$ and $R^{38}$-$R^{43}$ is independently, or at least two or more of $R^1$-$R^6$ combine to form, a fluorophore that is excited upon exposure to electromagnetic radiation having a second distribution of wavelengths that is different from the first distribution of wavelengths, for example, wherein the first and second distributions of wavelengths have different absorption maxima and, optionally wherein the first and second distributions of wavelengths are characterized by absorption peaks that are not overlapping. In an embodiment, for example, at least one of $R^1$-$R^6$ and $R^{38}$-$R^{43}$ is independently, or at least two of $R^1$-$R^6$ combine to form, a $C_5$-$C_{30}$ aryl or $C_5$-$C_{30}$ heteroaryl fluorophore, optionally a $C_5$-$C_{20}$ aryl or $C_5$-$C_{20}$ heteroaryl fluorophore, having one or more electron donating groups as substituents, having one or more electron withdrawing groups as substituents, or having both electron donating and electron withdrawing groups as substituents. In an embodiment, at least one of $R^1$-$R^6$ and $R^{38}$-$R^{43}$, is independently, or at least two or more of $R^1$-$R^6$ combine to form, a fluorophore group corresponding to a pyrazine, a thiazole, a phenylxanthene, a phenothiazine, a phenoselenazine, a cyanine, an indocyanine, a squaraine, a dipyrrolo pyrimidone, an anthraquinone, a tetracene, a quinoline, an acridine, an acridone, a phenanthridine, an azo dye, a rhodamine, a phenoxazine, an azulene, an azaazulene, a triphenyl methane dye, an indole, a benzoindole, an indocarbocyanine, a Nile Red dye, or a benzoindocarbocyanine, optionally having one or more electron donating groups, electron withdrawing groups, or targeting ligands provided as one or more substituents.

In an embodiment, the invention provides optical agents for phototherapy having a targeting ligand or other molecular recognition component for delivering the optical agent to a selected organ, tissue, or other cell material. Incorporation of a targeting ligand or molecular recognition component in some compounds and methods of the invention enables targeted delivery such that at least a portion of phototherapeutic agent administered to a subject accumulates at a desired site, such as the site of an organ, tissue, tumor or other lesion, prior to or during exposure to electromagnetic radiation. The invention includes, for example, compounds of any one of formula (FX1)-(FX35) and (FX38), wherein at least one of $R^1$-$R^6$ and $R^{38}$-$R^{43}$ is independently a targeting ligand (abbreviated as "Bm" throughout this description). In some embodiments, at least two of $R^1$-$R^6$ combine to form a group, such as a $C_5$-$C_{30}$ aryl or $C_5$-$C_{30}$ heteroaryl, that includes at least one targeting ligand (Bm). Targeting ligands for the present compounds include one or more biomolecules, or fragments or derivatives thereof, which include hormones, amino acids, peptides, peptidomimetics, proteins, nucleosides, nucleotides, nucleic acids, oligonucleotides, polynucleotides, enzymes, carbohydrates, glycomimetics, lipids, albumins, mono- and polyclonal antibodies, receptors, drugs, inclusion compounds such as cyclodextrins, and receptor binding molecules.

In an embodiment, the invention provides compounds of any one of formulae (FX1)-(FX35) and (FX38), wherein each of $R^7$-$R^{37}$ is independently hydrogen or a $C_1$-$C_{10}$ alkyl, and optionally wherein each of $R^7$-$R^{37}$ is hydrogen or a $C_1$-$C_5$ alkyl, and optionally wherein each of $R^7$-$R^{37}$ is hydrogen. In an embodiment, the invention provides compounds of any one of formulae (FX1)-(FX35) and (FX38), wherein each of $R^{34}$ and $R^{35}$ is hydrogen.

$L^1$-$L^6$ and $W^1$-$W^6$ groups may be spacer and attaching groups, respectively, for providing an appropriate linkage between $R^1$-$R^6$ and the central alicyclic diaza ring of the compounds of (FX1)-(FX35) and (FX38). In some embodiments, the invention provides compounds of any one of formulae (FX1)-(FX35) and (FX38), wherein any one of $L^1$-$L^6$ is independently a spacer moiety for establishing the steric environment between $R^1$-$R^6$ and the central alicyclic diaza ring. In some embodiments, the invention provides compounds of any one of formulae (FX1)-(FX35) and (FX38), wherein any one of $W^1$-$W^6$ is independently an attaching moiety for attaching $R^1$-$R^6$ directly or indirectly to the central alicyclic diaza ring. In an embodiment, at least one of $W^1$-$W^6$ is independently —$(CH_2)_n$—, —$(HCCH)_n$—, —$(CHOH)_m$—, or —$(CH_2CH_2O)_m$—, wherein each of m is independently an integer selected from the range of 1 to 100, optionally from the range of 1 to 10, and each n is independently an integer selected from the range of 1-10, optionally selected from the range of 1 to 5. In an embodiment, the invention provides compounds of any one of formulae (FX1)-(FX35) and (FX38), wherein at least one of $W^1$-$W^6$ is independently a single bond, —O—, —CO—, —COO—, —OCO—, —OCOO—, —$NR^7$—, —$CONR^8$—, —$NR^9CO$—; —$NR^{12}CONR^{13}$—, or —$NR^{14}CSNR^{15}$—. In an embodiment, the invention provides compounds of any one of formulae (FX1)-(FX35) and (FX38), wherein at least one of: $L^1$ and $W^1$, $L^2$ and $W^2$, $L^3$ and $W^3$, $L^4$ and $W^4$, $L^5$ and $W^5$, and $L^6$ and $W^6$ combine to form: —$(CH_2)_d$—, —O$(CH_2)_d$—, —$CO(CH_2)_d$—, —$OCO(CH_2)_d$—, —$COO(CH_2)_d$—, —$OCOO(CH_2)_d$—, —$N(R^7)(CH_2)_d$—, —$CONR^8(CH_2)_d$—, —$NR^9CO(CH_2)_d$—, —$OCONR^{10}(CH_2)_d$—, —$NR^{11}COO(CH_2)_d$—, —$NR^{12}CONR^{13}(CH_2)_d$—, or —$NR^{14}CSNR^{15}(CH_2)_d$—, wherein each d is independently an integer selected from the range of 1 to 100.

Reference to f, e, h, i, j, and k respectively, equal to 1 in the context of the compounds of formulae (FX1)-(FX35) refers to compounds of the invention wherein $L^1$, $L^2$, $L^3$, $L^4$, $L^5$, and/or $L^6$, respectively, is present in the compound. Reference to f, e, h, i, j, and k, respectively, equal to 0 in the context of formula (FX1)-(FX35) refers to embodiments wherein $L^1$, $L^2$, $L^3$, $L^4$, $L^5$, and/or $L^6$, respectively, is not present in the compound. As used herein, reference to f, e, h, i, j, and k as 0 refers to configurations wherein $W^1$, $W^2$, $W^3$, $W^4$, $W^5$, and/or $W^6$, respectively, is directly bonded by a single bond or double bond to the central alicyclic diaza ring of the compound. As used herein, reference $W^1$, $W^2$, $W^3$, $W^4$, $W^5$, and/or $W^6$ as a single bond and f, e, h, i and j, respectively, equal to 1, refers to configurations wherein $L^1$, $L^2$, $L^3$, $L^4$, $L^5$, and/or $L^6$, respectively, is directly bonded by a single bond to $R^1$, $R^2$, $R^3$, $R^4$, $R^5$, and/or $R^6$, respectively. As used herein, reference to f, e, h, i, j, and k, respectively, as equal to 0 and $W^1$, $W^2$, $W^3$, $W^4$, $W^5$, and/or $W^6$, respectively, as a single bond refers to configurations wherein to $R^1$, $R^2$, $R^3$, $R^4$, $R^5$, and/or $R^6$, respectively, is directly bonded by a single bond to the central alicyclic diaza ring of the compound. For example, $R^1$ is directly bonded to the central alicyclic diaza ring by a single bond for the case when f is equal to 0 and $W^1$ is designated as single bond; $R^2$ is directly bonded to the central alicyclic diaza ring by a single bond for the case when e is equal to 0 and $W^2$ is designated as single bond; $R^3$ is directly bonded to the central alicyclic diaza ring portion by a single bond for the case when h is equal to 0 and $W^3$ is designated as single bond; $R^4$ is directly bonded to the central alicyclic diaza ring by a single bond for the case when i is equal to 0 and $W^4$ is designated as single bond; $R^5$ is directly bonded to the central alicyclic diaza ring by a single bond for the case when j is equal to 0 and $W^5$ is designated as single bond; and $R^6$ is directly bonded to the central alicyclic diaza ring by a single bond for the case when k is equal to 0 and $W^6$ is designated as single bond For example, $R^2$ is directly bonded to the central diaza ring by a double bond for the case when e is equal to 0 and $W^2$ is designated as double bond; $R^3$ is directly bonded to the central diaza ring portion by a double bond for the case when h is equal to 0 and $W^3$ is designated as double bond; $R^4$ is directly bonded to the central diaza ring by a double bond for the case when i is equal to 0 and $W^4$ is designated as double bond; $R^5$ is directly bonded to the central diaza ring by a double bond for the case when j is equal to 0 and $W^5$ is designated as double bond; and $R^6$ is directly bonded to the central diaza ring by a double bond for the case when k is equal to 0 and $W^6$ is designated as double bond. This description scheme in relation f, e, h, i, j, k, $L^1$-$L^6$, $W^1$-$W^6$ and $R^1$-$R^6$ is used throughout the present description including in the description of embodiments of formulae (FX1)-(F35).

In an embodiment, for example, the invention provides a compound for phototherapy having any one of formula (FX1)-(FX35) and (FX38), wherein $R^1$-$R^6$, and optionally $R^{38}$-$R^{43}$, do not include an azo group. In an embodiment, for example, the invention provides a compound for phototherapy having any one of formula (FX1)-(FX35) and (FX38), wherein $R^1$-$R^6$, and optionally $R^{38}$-$R^{43}$, do not include an azide group. In an embodiment, for example, the invention provides a compound for phototherapy having any one of formula (FX1)-(FX35) and (FX38), wherein $R^1$-$R^6$, and optionally $R^{38}$-$R^{43}$, do not include a sulfenate group. In an embodiment, for example, the invention provides a compound for phototherapy having any one of formula (FX1)-(FX35) and (FX38), wherein $R^1$-$R^6$, and optionally $R^{38}$-$R^{43}$, do not include a thiadiazole group. In an embodiment, for example, the invention provides a compound for phototherapy having any one of formula (FX1)-(FX35) and (FX38), wherein $R^1$-$R^6$, and optionally $R^{38}$-$R^{43}$, do not include a cyanate group. In an embodiment, for example, the invention provides a compound for phototherapy having any one of formula (FX1)-(FX35) and (FX38), wherein $R^1$-$R^6$, and optionally $R^{38}$-$R^{43}$, do not include an isocyanide group. In an embodiment, for example, the invention provides a compound for phototherapy having any one of formula (FX1)-(FX35) and (FX38), wherein $R^1$-$R^6$, and optionally $R^{38}$-$R^{43}$, do not include an isocyanate group. In an embodiment, for example, the invention provides a compound for phototherapy having any one of formula (FX1)-(FX35) and (FX38), wherein $R^1$-$R^6$, and optionally $R^{38}$-$R^{43}$, do not include an isothiocyanate group. In an embodiment, for example, the invention provides a compound for phototherapy having any one of formula (FX1)-(FX35) and (FX38), wherein $R^1$-$R^6$, and optionally $R^{38}$-$R^{43}$, do not include a thiocyanate group.

In some embodiments, compounds of the invention may optionally include a poly(ethylene glycol) (abbreviated as PEG) component. In an embodiment, for example, the invention provides a composition having any one of the formula (FX1)-(FX35) and (FX38), wherein at least one of $R^1$-$R^6$, $L^1$-$L^6$ and $R^{38}$-$R^{43}$ is a substituent comprising —$(CH_2 OCH_2)_m$— or a derivative thereof, wherein m is an integer selected from the range of 1 to 100. Incorporation of a poly (ethylene glycol) glycol component in some compositions of the invention provides pharmacokinetic, chemical, and/or physical properties useful for bioanalytical, diagnostic and/or phototherapeutic applications. Poly(ethylene glycol) containing compounds of some embodiments of the present invention, for example, provide enhanced biocompatibility, low toxicity and suppress immune responses upon administration. Poly(ethylene glycol) containing compounds of some embodiments of the invention facilitate formulation, administration and/or delivery, for example, by enhancing solubility.

In an embodiment, the invention provides an optical agent having any one of formula (FX1)-(FX35) and (FX38), wherein each of $R^7$-$R^{33}$ is independently hydrogen or $C_1$-$C_{10}$ alkyl, and optionally wherein each of $R^7$-$R^{33}$ is independently hydrogen or $C_1$-$C_5$ alkyl, and optionally wherein each of $R^7$-$R^{33}$ is hydrogen. In an embodiment, the invention provides an optical agent having any one of formula (FX1)-(FX35) and (FX38), wherein each m or n is independently an integer selected from the range of 1 to 50, and optionally wherein each m or n is independently an integer selected from the range of 1 to 20, and wherein each m or n is independently an integer selected from the range of 1 to 20. In an embodiment, the invention provides an optical agent having any one of formula (FX19)-(FX35) and (FX38), wherein each of $R^{38}$-$R^{43}$ is independently hydrogen or $C_1$-$C_{10}$ alkyl, and optionally wherein each of $R^{38}$-$R^{43}$ is independently hydrogen or $C_1$-$C_5$ alkyl, and optionally wherein each of $R^{38}$-$R^{43}$ is hydrogen.

The invention further provides a phototherapeutic agent comprising the compound having any one of formula (FX1)-(FX41) or a pharmaceutical formulation thereof, for use in a medical phototherapy procedure, such as a Type 1 or Type 2 phototherapy procedure. In an embodiment, the invention provides a phototherapeutic agent comprising a pharmaceutically acceptable formulation, wherein an active ingredient of the formulation provided in a therapeutically effective amount is a compound having any one of formula (FX1)-(FX41). The invention includes, for example, formulations further comprising a compound having any one of formula (FX1)-(FX41) and one or more pharmaceutically acceptable carriers or excipients. In an embodiment, the medical phototherapy procedure comprises: (i) administering to a subject in need of treatment a therapeutically effective amount of the phototherapeutic agent comprising the compound having any one of formula (FX1)-(FX41); and (ii) exposing the phototherapeutic agent administered compound to the patient to a therapeutically effective amount of electromagnetic radiation. In an embodiment, the administered compound is exposed to electromagnetic radiation having wavelengths selected over a range of 350 nanometers to 1300 nanometers, optionally having wavelengths selected over a range of 350 nanometers to 900 nanometers. In an embodiment, exposing the administered compound to the patient to electromagnetic radiation cleaves a N—N bond of the central alicyclic diaza ring of the compound. In an embodiment, exposing the administered compound to the patient to a therapeutically effective amount of electromagnetic radiation generates a therapeutically effective amount of photoactivated compound. In an embodiment, exposing the administered compound to a therapeutically effective amount of electromagnetic radiation generates a therapeutically effective amount of reactive species causing localized cell death. In an embodiment, the medical phototherapy procedure further comprises administering or otherwise targeting the administered compound to a target tissue of the subject, such as a tumor or lesion, site of inflammation, vasculature tissue, or organ. In an embodiment, methods of the invention further comprises exposing the administered compound at the target tissue to light having sufficient power, fluence, intensity and/or dose (net number of photons provided to the target tissue) to result in injury, inactivation and/or death to cells at the target tissue. Methods of the invention include methods for treating cancer, inflammation and vascular disease.

Another aspect of the invention is directed to methods of using the compounds of any one of formulae (FX1)-(FX41) in medical procedures. The invention includes, for example, methods of using the compounds of any one of formulae (FX1)-(FX41) in a medical phototherapy procedure. In one such medical phototherapy procedure, a therapeutically effective amount of a compound of any one of formulae (FX1)-(FX41) is administered to a subject (e.g., via intravenous or intraarterial injection, oral administration, topical administration, etc.) and exposed to a therapeutically effective amount of electromagnetic radiation, such as electromagnetic radiation having wavelengths in the visible and near infrared regions of the electromagnetic spectrum (e.g., 350 nm to 1300 nm). In a method, the electromagnetic radiation exposed to the compound of any one of formulae (FX1)-(FX41) does not have wavelengths in the X-ray region of the electromagnetic spectrum. In a method, the electromagnetic radiation exposed to the compound of any one of formulae (FX1)-(FX41) does not have wavelengths in the ultraviolet region of the electromagnetic spectrum. In an embodiment, non-ionizing electromagnetic radiation is used in the present methods. "Non-ionizing electromagnetic radiation" herein refers to electromagnetic radiation wherein a single photon does not have enough energy to completely remove at least one electron from an atom or molecule of the subject's body.

Without wishing to be bound by any particular theory, there can be discussion herein of beliefs or understandings of underlying principles or mechanisms relating to the invention. It is recognized that regardless of the ultimate correctness of any explanation or hypothesis, an embodiment of the invention can nonetheless be operative and useful.

BRIEF DESCRIPTION OF THE FIGURES

FIGS. 1A and 1B provide schematic representations of reaction mechanisms for phototherapeutic agents comprising a compound having formula (FX5), and FIGS. 1C and 1D provide schematic representations of reaction mechanisms for phototherapeutic agents comprising a compound having formula (FX30).

STATEMENTS REGARDING CHEMICAL COMPOUNDS AND NOMENCLATURE

Figure 1A:
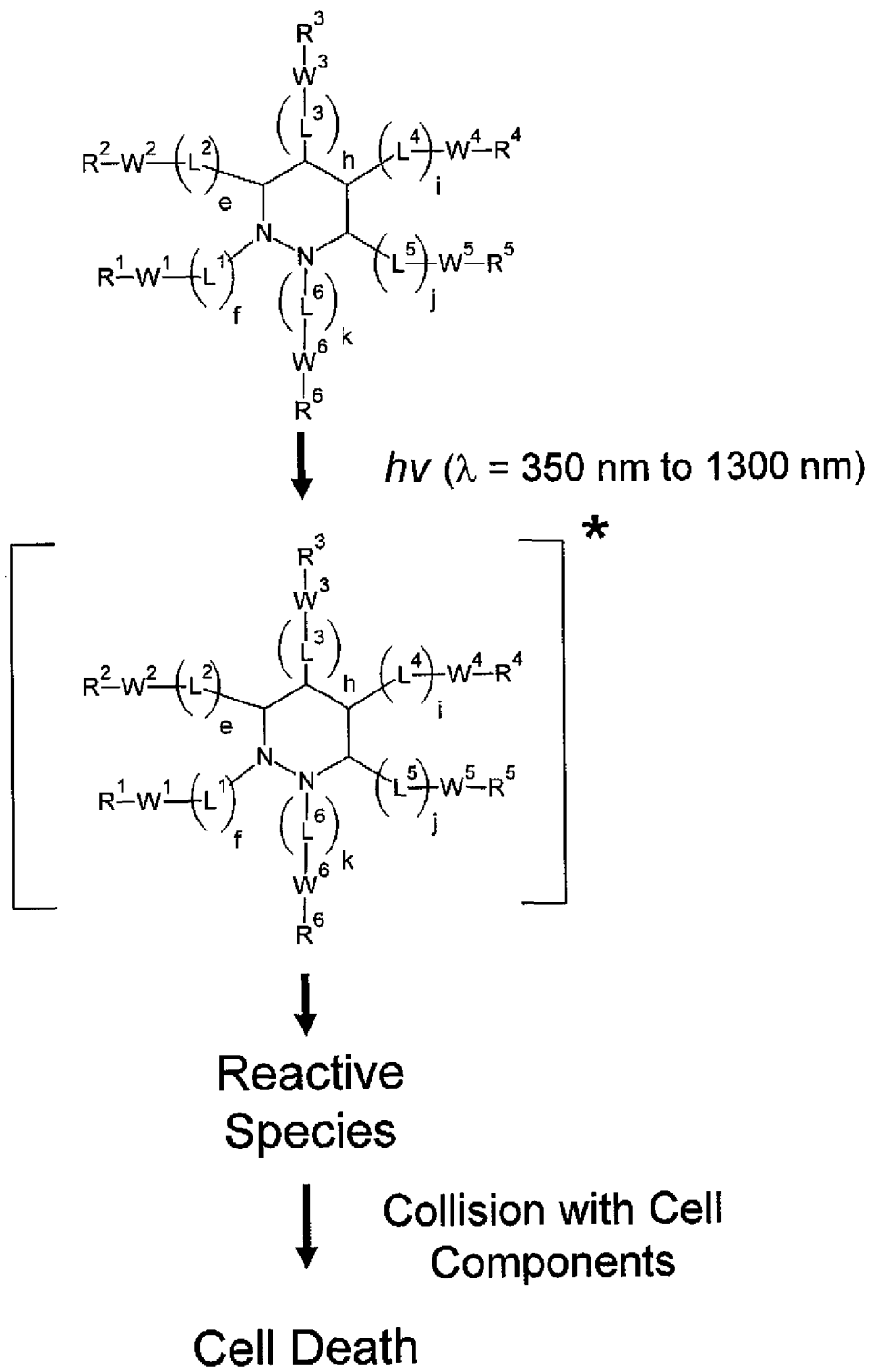
FIGS. 1A-1D provide schematic representations of reaction mechanisms for phototherapeutic agents having an alicyclic diaza ring with a photolabile N—N bond, wherein exposure to electromagnetic radiation activates the phototherapeutic agent, for example, resulting in bond cleavage and generating reactive species.

In an embodiment, a composition or compound of the invention is isolated or purified. In an embodiment, an isolated or purified compound is at least partially isolated or purified as would be understood in the art. In an embodiment, the composition or compound of the invention has a chemical purity of 90%, optionally for some applications 95%, optionally for some applications 99%, optionally for some applications 99.9%, optionally for some applications 99.99%, and optionally for some applications 99.999% pure.

Many of the molecules disclosed herein contain one or more ionizable groups. Ionizable groups include groups from which a proton can be removed (e.g., —COOH) or added (e.g., amines) and groups which can be quaternized (e.g., amines). All possible ionic forms of such molecules and salts thereof are intended to be included individually in the disclosure herein. With regard to salts of the compounds herein, one of ordinary skill in the art can select from among a wide variety of available counterions that are appropriate for preparation of salts of this invention for a given application. In specific applications, the selection of a given anion or cation for preparation of a salt can result in increased or decreased solubility of that salt.

The compounds of this invention can contain one or more chiral centers. Accordingly, this invention is intended to include racemic mixtures, diasteromers, enantiomers, tautomers and mixtures enriched in one or more stereoisomer. The scope of the invention as described and claimed encompasses the racemic forms of the compounds as well as the individual enantiomers and non-racemic mixtures thereof.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc. valence states.

As is customary and well known in the art, hydrogen atoms in formulas (FX1)-(FX41) are not always explicitly shown, for example, hydrogen atoms bonded to the carbon atoms of aromatic, alicyclic, carbocyclic and/or heterocyclic rings are not always explicitly shown in formulas (FX1)-(FX41). The structures provided herein, for example in the context of the description of formulas (FX1)-(FX41), are intended to convey to one of reasonable skill in the art the chemical composition of compounds of the methods and compositions of the invention, and as will be understood by one of skill in the art, the structures provided do not indicate the specific positions of atoms and bond angles between atoms of these compounds.

As used herein, the terms "alkylene" and "alkylene group" are used synonymously and refer to a divalent group derived from an alkyl group as defined herein. The invention includes compounds having one or more alkylene groups. Alkylene groups in some compounds function as attaching and/or spacer groups. Compounds of the invention may have substituted and/or unsubstituted $C_1$-$C_{20}$ alkylene, $C_1$-$C_{10}$ alkylene and $C_1$-$C_5$ alkylene groups.

As used herein, the terms "cycloalkylene" and "cycloalkylene group" are used synonymously and refer to a divalent group derived from a cycloalkyl group as defined herein. The invention includes compounds having one or more cycloalkylene groups. Cycloalkyl groups in some compounds function as attaching and/or spacer groups. Compounds of the invention may have substituted and/or unsubstituted $C_3$-$C_{20}$ cycloalkylene, $C_3$-$C_{10}$ cycloalkylene and $C_3$-$C_5$ cycloalkylene groups.

As used herein, the terms "arylene" and "arylene group" are used synonymously and refer to a divalent group derived from an aryl group as defined herein. The invention includes compounds having one or more arylene groups. In some embodiments, an arylene is a divalent group derived from an aryl group by removal of hydrogen atoms from two intra-ring carbon atoms of an aromatic ring of the aryl group. Arylene groups in some compounds function as attaching and/or spacer groups. Arylene groups in some compounds function as chromophore, fluorophore, aromatic antenna, dye and/or imaging groups. Compounds of the invention include substituted and/or unsubstituted $C_3$-$C_{30}$ arylene, $C_3$-$C_{20}$ arylene, $C_3$-$C_{10}$ arylene and $C_1$-$C_5$ arylene groups.

As used herein, the terms "heteroarylene" and "heteroarylene group" are used synonymously and refer to a divalent group derived from a heteroaryl group as defined herein. The invention includes compounds having one or more heteroarylene groups. In some embodiments, a heteroarylene is a divalent group derived from a heteroaryl group by removal of hydrogen atoms from two intra-ring carbon atoms or intra-ring nitrogen atoms of a heteroaromatic or aromatic ring of the heteroaryl group. Heteroarylene groups in some compounds function as attaching and/or spacer groups. Heteroarylene groups in some compounds function as chromophore, aromatic antenna, fluorophore, dye and/or imaging groups. Compounds of the invention include substituted and/or unsubstituted $C_3$-$C_{30}$ heteroarylene, $C_3$-$C_{20}$ heteroarylene, $C_1$-$C_{10}$ heteroarylene and $C_3$-$C_5$ heteroarylene groups.

As used herein, the terms "alkenylene" and "alkenylene group" are used synonymously and refer to a divalent group derived from an alkenyl group as defined herein. The invention includes compounds having one or more alkenylene groups. Alkenylene groups in some compounds function as attaching and/or spacer groups. Compounds of the invention include substituted and/or unsubstituted $C_2$-$C_{20}$ alkenylene, $C_2$-$C_{10}$ alkenylene and $C_2$-$C_5$ alkenylene groups.

As used herein, the terms "cylcoalkenylene" and "cylcoalkenylene group" are used synonymously and refer to a divalent group derived from a cylcoalkenyl group as defined herein. The invention includes compounds having one or more cylcoalkenylene groups. Cycloalkenylene groups in some compounds function as attaching and/or spacer groups. Compounds of the invention include substituted and/or unsubstituted $C_3$-$C_{20}$ cylcoalkenylene, $C_3$-$C_{10}$ cylcoalkenylene and $C_3$-$C_5$ cylcoalkenylene groups.

As used herein, the terms "alkynylene" and "alkynylene group" are used synonymously and refer to a divalent group derived from an alkynyl group as defined herein. The invention includes compounds having one or more alkynylene groups. Alkynylene groups in some compounds function as attaching and/or spacer groups. Compounds of the invention include substituted and/or unsubstituted $C_2$-$C_{20}$ alkynylene, $C_2$-$C_{10}$ alkynylene and $C_2$-$C_5$ alkynylene groups.

As used herein, the term "halo" refers to a halogen group such as a fluoro (—F), chloro (—Cl), bromo (—Br), iodo (—I) or astato (—At).

The term "heterocyclic" refers to ring structures containing at least one other kind of atom, in addition to carbon, in the ring. Examples of such atoms include nitrogen, oxygen and sulfur. Examples of heterocyclic rings include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups. Atoms of heterocyclic rings can be bonded to a wide range of other atoms and functional groups, for example, provided as substituents.

The term "carbocyclic" refers to ring structures containing only carbon atoms in the ring. Carbon atoms of carbocyclic rings can be bonded to a wide range of other atoms and functional groups, for example, provided as substituents.

The term "alicyclic" refers to a ring that is not an aromatic ring. Alicyclic rings include both carbocyclic and heterocyclic rings.

As used herein, the term "alkoxyalkyl" refers to a substituent of the formula alkyl-O-alkyl.

As used herein, the term "polyhydroxyalkyl" refers to a substituent having from 2 to 12 carbon atoms and from 2 to 5 hydroxyl groups, such as the 2,3-dihydroxypropyl, 2,3,4-trihydroxybutyl or 2,3,4,5-tetrahydroxypentyl residue.

As used herein, the term "polyalkoxyalkyl" refers to a substituent of the formula alkyl-(alkoxy)$_n$-alkoxy wherein n is an integer from 1 to 10, preferably 1 to 4, and more preferably for some embodiments 1 to 3.

Amino acids include glycine, alanine, valine, leucine, isoleucine, methionine, proline, phenylalanine, tryptophan, asparagine, glutamine, glycine, serine, threonine, serine, rhreonine, asparagine, glutamine, tyrosine, cysteine, lysine, arginine, histidine, aspartic acid and glutamic acid. As used herein, reference to "a side chain residue of a natural α-amino acid" specifically includes the side chains of the above-referenced amino acids.

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alkyl group having a ring structure such as ring structure comprising 3-30 carbon atoms, optionally 3-20 carbon atoms and optionally 2-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, or 7-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alkyl portion of the groups is substituted as provided herein in connection with the description of alkyl groups. As used herein MeO— refers to $CH_3O$—.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9- or 10-member carbon ring(s) and particularly those having a 3-, 4-, 5-, 6- or 7-member ring(s). The carbon rings in cycloalkenyl groups can also carry alkyl groups. Cycloalkenyl groups can include bicyclic and tricyclic alkenyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms.

Aryl groups include groups having one or more 5-, 6- or 7-member aromatic and/or heterocyclic aromatic rings. The term heteroaryl specifically refers to aryl groups having at least one 5-, 6- or 7-member heterocyclic aromatic rings. Aryl groups can contain one or more fused aromatic and heteroaromatic rings or a combination of one or more aromatic or heteroaromatic rings and one or more non-aromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those which are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein are provided in a covalently bonded configuration in the compounds of the invention at any suitable point of attachment. In embodiments, aryl groups contain between 5 and 30 carbon atoms. In embodiments, aryl groups contain one aromatic or heteroaromatic six-membered ring and one or more additional five- or six-membered aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms.

As to any of the groups described herein which contain one or more substituents, it is understood that such groups do not contain any substitution or substitution patterns which are sterically impractical and/or synthetically non-feasible. In addition, the compounds of this invention include all stereochemical isomers arising from the substitution of these compounds. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl and aryl group includes substitution with one or more of the following substituents, among others:

halogen, including fluorine, chlorine, bromine or iodine; pseudohalides, including —CN;

—COOR where R is a hydrogen or an alkyl group or an aryl group and more specifically where R is a methyl, ethyl, propyl, butyl, or phenyl group all of which groups are optionally substituted;

—COR where R is a hydrogen or an alkyl group or an aryl group and more specifically where R is a methyl, ethyl, propyl, butyl, or phenyl group all of which groups are optionally substituted;

—CON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—OCON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—N(R)$_2$ where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring which can contain one or more double bonds and can contain one or more additional carbon atoms;

—SR, where R is hydrogen or an alkyl group or an aryl group and more specifically where R is hydrogen, methyl, ethyl, propyl, butyl, or a phenyl group, which are optionally substituted;

—SO$_2$R, or —SOR where R is an alkyl group or an aryl group and more specifically where R is a methyl, ethyl, propyl, butyl, or phenyl group, all of which are optionally substituted;

—OCOOR where R is an alkyl group or an aryl group;

—SO$_2$N(R)$_2$ where each R, independently of each other R, is a hydrogen, or an alkyl group, or an aryl group all of which are optionally substituted and wherein R and R can form a ring which can contain one or more double bonds and can contain one or more additional carbon atoms;

—OR where R is H, an alkyl group, an aryl group, or an acyl group all of which are optionally substituted. In a particular example R can be an acyl yielding —OCOR" where R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

DETAILED DESCRIPTION

The following definitions and methods are provided to better define the invention and to guide those of ordinary skill in the art in the practice of the invention.

Referring to the drawings, like numerals indicate like elements and the same number appearing in more than one drawing refers to the same element. In general the terms and phrases used herein have their art-recognized meaning, which can be found by reference to standard texts, journal references and contexts known to those skilled in the art. The following definitions are provided to clarify their specific use in the context of the invention.

The term "inflammation" generally refers to a biological response of tissues to harmful stimuli, such as pathogens, damaged cells, irritants, etc. Inflammation can be either acute or chronic. Acute inflammation is an initial response of the body to harmful stimuli and can be achieved by the increased movement of plasma and leukocytes from the blood into injured tissues. An inflammatory response can involve the local vascular system, the immune system, and/or various cells within the injured tissue. Prolonged inflammation, referred to as chronic inflammation, can lead to a progressive shift in the type of cells which are present at the site of inflammation can be characterized by simultaneous destruction and healing of the tissue from the inflammatory process.

The term "amino acid" comprises naturally occurring amino acids as well as non-naturally occurring amino acids, including amino acid analogs and derivatives. One skilled in the art will recognize that reference herein to an amino acid includes, for example, naturally occurring proteogenic L-amino acids; D-amino acids; chemically modified amino acids such as amino acid analogs and derivatives; naturally occurring non-proteogenic amino acids, and chemically synthesized compounds having properties known in the art to be characteristic of amino acids.

The term "nucleic acid" as used herein generally refers to a molecule or strand of DNA, RNA, or derivatives or analogs thereof including one or more nucleobases. Nucleobases comprise purine or pyrimidine bases typically found in DNA or RNA (e.g., adenine, guanine, thymine, cytosine, and/or uracil). The term "nucleic acid" also comprises oligonucleotides and polynucleotides. Nucleic acids may be single-stranded molecules, or they may be double-, triple- or quadruple-stranded molecules that may comprise one or more complementary strands of a particular molecule. "Nucleic acid" includes artificial nucleic acids including peptide nucleic acids, morpholino nucleic acids, glycol nucleic acids and threose nucleic acids. Artificial nucleic acids may be capable of nucleic acid hybridization.

As used herein, "sequence" means the linear order in which monomers occur in a polymer, the order of amino acids in a polypeptide or the order of nucleotides in a polynucleotide for example.

"Optical agent" generally refers to compounds, compositions, preparations, and/or formulations that absorb, emit, or scatter electromagnetic radiation of wavelength generally in the range of 350-1300 nanometers, within a biologically relevant environment or condition. In some embodiments, optical agents of the invention, when excited by electromagnetic radiation, undergo emission via fluorescence or phosphorescence pathways. These pathways are useful for diagnostic imaging, visualization, or organ function monitoring. Compounds belonging to this class are commonly referred to as "optical imaging agents" or "optical contrast agents." In some other embodiments, optical agents of the invention absorb electromagnetic radiation and undergo photochemical reactions such as photofragmentation of one or more photolabile bonds to generate reactive species such as nitrenes, carbene, free radicals, ions, excited species, etc. This process is useful for a wide range of phototherapy applications, for example in the treatment of tumors or other lesions. Compounds belonging to this class are commonly referred to as "photosensitizers." The term "photosensitizer" refers to a phototherapeutic agent or a component thereof providing for photoactivation, for example, photoactivation resulting in generation of reactive species that locally kill, injure, inactivate or otherwise degrade cells (e.g., cancer cells, tumor cells, non-cancer cells, etc.). Photosensitizers of some embodiments undergo photoactivation that initiates bond cleavage reactions, such as photolysis and/or nitrogen extrusion reactions, thereby generating reactive species capable of causing localized cell death or injury. Optical agents include Type 1 and Type 2 phototherapeutic agents. Optical agents include, but are not limited to, phototherapeutic agents (Type 1 and 2), photosensitizers, imaging agents, dyes, detectable agents, photosensitizer agents, photoactivators, and photoreactive agents; and conjugates, complexes, and derivatives thereof.

As used herein, a "chromophore" is a compound or functional group of a compound that results in absorption of electromagnetic radiation, preferably for some applications electromagnetic radiation having wavelengths in the UV (e.g. 200 nm to 350 nm) or visible (e.g. 350 nm to 750 nm) of the electromagnetic spectrum.

As used herein, a "fluorophore" is a compound or functional group of a compound that results in absorption of electromagnetic radiation and subsequent fluorescence. Preferably for some applications incorporation of a fluorophore results in compounds of the invention that absorb electromagnetic radiation and generate fluorescence having wavelengths in the UV (e.g. 200 nm to 350 nm) or visible (e.g. 350 nm to 750 nm) of the electromagnetic spectrum. In some embodiment, incorporation of a fluorophore results in compounds having an appreciable quantum yield for fluorescence, such as a quantum yield over the range of 0.001 to 1, 0.01 to 1, optionally 0.1 to 1. Optical agents of the present invention can contain fluorophores. Fluorophores can be functional groups in a molecule which absorb electromagnetic radiation of first specific wavelengths and re-emit energy at second specific wavelengths. The amount and wavelengths of the emitted electromagnetic radiation depend on both the fluorophore and the chemical environment of the fluorophore. The term "fluorophore" may be abbreviated throughout the present description as "FL". In aspects of the invention, fluorophores emit energy in the visible (e.g. 350 nm to 750 nm) and NIR regions (e.g., 750-1300 nm) of the electromagnetic spectrum.

As used herein, the term "luminescence" refers to the emission of electromagnetic radiation from excited electronic states of atoms or molecules. Luminescence generally refers to electromagnetic radiation emission, such as photoluminescence, chemiluminescence, and electrochemiluminescence, among others. In photoluminescence, including fluorescence and phosphorescence, the excited electronic state is created by the absorption of electromagnetic radiation. Luminescence detection involves detection of one or more properties of the luminescence or associated luminescence process. These properties can include intensity, excitation and/or emission spectrum, polarization, lifetime, and energy transfer, among others. These properties can also include time-independent (steady-state) and/or time-dependent (time-resolved) properties of the luminescence. Representative luminescence techniques include fluorescence intensity (FLINT), fluorescence polarization (FP), fluorescence resonance energy transfer (FRET), fluorescence lifetime (FLT), total internal reflection fluorescence (TIRE), fluorescence correlation spectroscopy (FCS), fluorescence recovery after photobleaching (FRAP), and bioluminescence resonance energy transfer (BRET), among others. By way of example, when an optical agent is used in the present invention, it is desirable that the wavelength of radiation be non-ionizing and be such that it excites the optical agent. This excitation can cause a bond of the molecule to break and can lead to creation of one or more appropriate radical(s). This excitation can also cause the molecule to emit part of the absorbed energy at a different wavelength. Such emission can be detected using fluorometric techniques as described above. One skilled in the art can readily determine the most appropriate treatment and optional detection technique based, at least in part, on the specific phototherapeutic agent(s) administered and/or the particular use (e.g., tissue to be treated).

Optical agents include, but are not limited to, phototherapeutic agents (Type 1 and 2), photosensitizers, imaging agents, dyes, detectable agents, photosensitizer agents, photoactivators, and photoreactive agents; and conjugates, complexes, and derivatives thereof.

"Phototherapy procedure" refers to a therapeutic procedure involving administration of a phototherapeutic agent to a patient followed by subsequent excitation by exposure to applied electromagnetic radiation, such as electromagnetic radiation having wavelengths in the visible and/or near IR region of the electromagnetic spectrum such as wavelengths in the range of 350-1300 nanometers, so as to generate a therapeutically effective amount of excited phototherapeutic agent. Phototherapy includes, but is not limited to, photodynamic therapy. As used herein phototherapy includes procedures involving administration of Type 1 and/or Type 2 phototherapeutic agents, optionally further including administration of one or more additional therapeutic agents. In an embodiment, the invention provides methods for carrying out a phototherapy procedure for treatment of cancer, inflammation, stenosis and vascular disease.

As used herein, "targeting ligand" (abbreviated as Bm) refers to a chemical group and/or substituent having functionality for targeting a compound of any one of formula (FX1)-(FX41) to an anatomical and/or physiological site of a patient, such as a selected cell, tissue or organ. For some embodiments, a targeting ligand is characterized as a ligand that selectively or preferentially binds to a specific biological site(s) (e.g., enzymes, receptors, etc.) and/or biological surface(s) (e.g., membranes, fibrous networks, etc.). In an embodiment, the invention provides compounds having any one of formula (FX1)-(FX41), wherein Bm is an amino acid, or a polypeptide comprising 2 to 30 amino acid units. In an embodiment, the invention provides compounds having any one of formula (FX1)-(FX41), wherein Bm is a mono- or polysaccharide comprising 1 to 50 carbohydrate units. In an embodiment, the invention provides compounds having any one of formula (FX1)-(FX41), wherein Bm is a mono-, oligo- or poly-nucleotide comprising 1 to 50 nucleic acid units. In an embodiment, the invention provides compounds having any one of formula (FX1)-(FX41), wherein Bm is a protein, an enzyme, a carbohydrate, a peptidomimetic, a glycomimetic, a glycopeptide, a glycoprotein, a lipid, an antibody (polyclonal or monoclonal), or fragment thereof. In an embodiment, the invention provides compounds having any one of formula (FX1)-(FX41), wherein Bm is an aptamer. In an embodiment, the invention provides compounds having any one of formula (FX1)-(FX41), wherein Bm is a drug, a hormone, steroid or a receptor. In some embodiments, each occurrence of Bm in the compounds of (FX1)-(FX41) is independently a monoclonal antibody, a polyclonal antibody, a metal complex, an albumin, or an inclusion compound such as a cyclodextrin. In some embodiments, each occurrence of Bm in the compounds of (FX1)-(FX41) is independently integrin, selectin, vascular endothelial growth factor, fibrin, tissue plasminogen, thrombin, LDL, HDL, Sialyl LewisX or a mimic thereof, or an atherosclerotic plaque binding molecule. Throughout the present description, the term "biomolecule" can be a targeting ligand (Bm). In an embodiment, the invention provides compounds having any one of formula (FX1) (FX41), wherein Bm is a polysaccharide comprising 2 to 50 furanose or pyranose units.

In the compounds of any one of formulas (FX1)-(FX41), Bm is a targeting ligand, optionally providing molecular recognition functionality. In some embodiments, the targeting ligand is a particular region of the compound that is recognized by, and binds to, a target site on an organ, tissue, tumor or cell. Targeting ligands are often, but not always, associated with biomolecules or fragments thereof which include, but are not limited to, hormones, amino acids, peptides, peptidomimetics, proteins, nucleosides, nucleotides, nucleic acids, enzymes, carbohydrates, glycomimetics, lipids, albumins, mono- and polyclonal antibodies, receptors, inclusion compounds such as cyclodextrins, and receptor binding molecules. Targeting ligands for use in the invention can also include synthetic polymers. Examples of synthetic polymers that are useful for targeting ligands include polyaminoacids, polyols, polyamines, polyacids, oligonucleotides, aborols, dendrimers, and aptamers. Still other examples of useful targeting ligands can include integrin, selectin, vascular endothelial growth factor, fibrin, tissue plasminogen activator, thrombin, LDL, HDL, Sialyl LewisX and its mimics, and atherosclerotic plaque binding molecules.

Specific examples of targeting ligands include, but are not limited to: steroid hormones for the treatment of breast and prostate lesions; whole or fragmented somatostatin, bombesin, and neurotensin receptor binding molecules for the treatment of neuroendocrine tumors; whole or fragmented cholecystekinin receptor binding molecules for the treatment of lung cancer; whole or fragmented heat sensitive bacterioendotoxin (ST) receptor and carcinoembryonic antigen (CEA) binding molecules for the treatment of colorectal cancer; dihydroxyindolecarboxylic acid and other melanin producing biosynthetic intermediates for the treatment of melanoma; whole or fragmented integrin receptor and atherosclerotic plaque binding molecules for the treatment of vascular diseases; and whole or fragmented amyloid plaque binding molecules for the treatment of brain lesions. In some embodiments, Bm, if present, is selected from heat-sensitive bacterioendotoxin receptor binding peptide, carcinoembryonic antigen antibody (anti-CEA), bombesin receptor binding peptide, neurotensin receptor binding peptide, cholecystekinin receptor binding peptide, somastatin receptor binding peptide, ST receptor binding peptide, neurotensin receptor binding peptide, leukemia binding peptides, folate receptor binding agents, steroid receptor binding peptide, carbohydrate receptor binding peptide or estrogen. In another embodiment Bm, if present, is a ST enterotoxin or fragment thereof. In some embodiments, Bm, if present, is selected from octreotide and octreotate peptides. In another embodiment Bm, if present, is a synthetic polymer. Examples of synthetic polymers useful for some applications include polyaminoacids, polyols, polyamines, polyacids, oligonucleotides, aborols, dendrimers, and aptamers. In an embodiment, Bm, if present, is an antibody or an antibody fragment, such as an antibody $F_{ab}$ fragment, an antibody $F_{(ab2)'}$ fragment, and an antibody $F_c$ fragment. Examples of specific peptide targeting ligands are described in WO/2008/108941.

"Target tissue" refers to tissue of a subject to which an optical agent is administered or otherwise contacted, for example during a biomedical procedure such as an optical imaging, phototherapy or visualization procedure. Target tissue may be contacted with an optical agent of the invention under in vivo conditions or ex vivo conditions. Target tissues in some methods of the invention include cancerous tissue, cancer cells, precancerous tissue, a tumor, a lesion, a site of inflammation, stenosis, or vascular tissue. Target tissue in some methods of the invention includes a melanoma cell, a breast lesion, a prostate lesion, a lung cancer cell, a colorectal cancer cell, an atherosclerotic plaque, a brain lesion, a blood vessel lesion, a lung lesion, a heart lesion, a throat lesion, an ear lesion, a rectal lesion, a bladder lesion, a stomach lesion, an intestinal lesion, an esophagus lesion, a liver lesion, a pancreatic lesion, and a solid tumor. Target tissue in some embodiments refers to a selected organ of the subject or component thereof, such as lung, heart, brain, stomach, liver, kidneys, gallbladder, pancreas, intestines, rectum, skin, colon, prostate, ovaries, breast, bladder, blood vessel, throat, ear, or esophagus.

As used herein, "tumor-specific agent" refers to an entity, such as an optical agent, that preferentially accumulates in a tumor at a higher level than normal tissue regardless of the particular mechanism of uptake in the tumors, either receptor mediated or enhance permeability and retention, EPR. Optical agents of the present invention include tumor-specific agents, including tumor specific phototherapy agents, for example having a targeting ligand providing specificity in the administration, delivery and/or binding to tumor tissue.

The terms "peptide" and "polypeptide" are used synonymously in the present description, and refer to a class of compounds comprising of amino acid residues chemically bonded together by amide bonds (or peptide bonds), regardless of length, functionality, environment, or associated molecule(s). Peptides and polypeptides are polymeric compounds comprising at least two amino acid residues or modified amino acid residues. Modifications can be naturally occurring or non-naturally occurring, such as modifications generated by chemical synthesis. Modifications to amino acids in peptides include, but are not limited to, phosphorylation, glycosylation, lipidation, prenylation, sulfonation, hydroxylation, acetylation, methionine oxidation, alkylation, acylation, carbamylation, iodination and the addition of cofactors. Peptides include proteins and further include compositions generated by degradation of proteins, for example by proteolyic digestion. Peptides and polypeptides can be generated by substantially complete digestion or by partial digestion of proteins. Polypeptides comprising 2 to 100 amino acid units, optionally for some embodiments 2 to 50 amino acid units and, optionally for some embodiments 2 to 20 amino acid units can be used as polypeptide targeting ligands in the invention, for example, where the polypeptide preferentially binds to proteins, peptides or other biomolecules expressed, or otherwise generated by, a target tissue, such as a tumor, precancerous tissue, site of inflammation or other lesion. Typically, the polypeptide is at least four amino acid residues in length and can range up to a full-length protein.

"Protein" refers to a class of compounds comprising one or more polypeptide chains and/or modified polypeptide chains. Proteins can be modified by naturally occurring processes such as post-translational modifications or co-translational modifications. Exemplary post-translational modifications or co-translational modifications include, but are not limited to, phosphorylation, glycosylation, lipidation, prenylation, sulfonation, hydroxylation, acetylation, methionine oxidation, the addition of cofactors, proteolysis, and assembly of proteins into macromolecular complexes. Modification of proteins can also include non-naturally occurring derivatives, analogues and functional mimetics generated by chemical synthesis. Exemplary derivatives include chemical modifications such as alkylation, acylation, carbamylation, iodination or any modification that derivatizes the protein.

As used herein, "polynucleotide" and "oligonucleotide" are used interchangeably and refer to a class of compounds composed of nucleic acid residues chemically bonded together. The invention provides optical agents having an oligonucleotide or polynucleotide targeting ligand which comprises a plurality of nucleic acid residues, such as DNA or RNA residues, and/or modified nucleic acid residues that preferentially binds to proteins, peptides or other biomolecules expressed, or otherwise generated by, a target tissue, such as a tumor, precancerous tissue, site of inflammation or other lesion. Modifications to nucleic acid residues can be naturally occurring or non-naturally occurring, such as modifications generated by chemical synthesis. Oligo- or polynucleotide targeting ligands include, for example, oligo- or poly-nucleotides comprising 2 to 100 nucleic acid units, optionally for some embodiments 2 to 50 nucleic acid units and, optionally for some embodiments 2 to 20 nucleic acid units, and optionally for some embodiments 2 to 10 nucleic acid units. Polypeptide and oligonucleotide include a polymer of at least two nucleotides joined together by phosphodiester bonds and may consist of either ribonucleotides or deoxyribonucleotides.

The term "aptamer" refers to an oligo- or poly-nucleotide or polypeptide that binds to, or otherwise selectively or preferentially associates with, a specific target molecule. For example, the invention provides optical agents having an aptamer targeting ligand that preferentially binds to proteins, peptides or other biomolecules expressed, or otherwise generated by, a target tissue, such as a tumor, precancerous tissue, site of inflammation or other lesion.

"Peptidomimetic" refers to a molecule having activity, including biological activity, that resembles that of a polypeptide or is substantially the same as a polypeptide. Morphine, for example, is a peptidomimetic of endorphin peptide. In some embodiments, a peptidomimetic is a small protein-like polymer designed to mimic the functionality of a peptide. Peptidomimetics useful as targeting ligands for some compounds of the invention in the present invention include peptoids and β-peptides. The composition and biological activity of peptidomimetics and use of peptidomimetics in targeted diagnostics and therapeutics are further described in the following references: (1) A. Giannis and T. Kotter, *Peptidomi-*

*metics for Receptor Ligands—Discovery, Development, and Medical Perspectives*, Angewandte Chemie International Edition In English, vol. 32, 1993, pg. 1244-1267; (3) Peptidomimetics, Accounts of Chemical Research, Vol. 41, No. 10, October 208, 1231-1232, by Wu and Gellman; and (3) Patch, J. A. et al., *Versatile oligo(N-substituted)glycines: The many roles of peptoids in drug discovery.*, Pseudo-Peptides in Drug Discovery 2004, 1-31 P. E. Nielsen.

As used herein, "spacer moiety" refers to a component provided between the central diaza ring of some compounds of the invention and one or more pendant R groups. In some embodiments, any one of $L^1$-$L^6$ in formulas (FX1)-(FX35) is a spacer moiety. Spacer moieties useful for some embodiments are provided between a targeting ligand or dye and the central diaza ring provided to enhance the overall chemical, optical, physical and/or pharmakientic properties of an optical agent of the present invention. Useful spacer moieties for compounds of the invention having formulas (FX1)-(FX35) include, but are not limited to, $C_1$-$C_{10}$ alkylene, $C_3$-$C_{10}$ cycloalkylene, $C_2$-$C_{10}$ alkenylene, $C_3$-$C_{10}$ cycloalkenylene, $C_2$-$C_{10}$ alkynylene, ethenylene, ethynylene, phenylene, 1-aza-2,5-dioxocyclopentylene, —$(CH_2CH_2O)_m$—, —$(CHOH)_m$—, or 1,4-diazacyclohexylene, wherein each of m is independently an integer selected from the range of 1 to 100, optionally selected from the range of 1 to 10. The invention includes compounds having formulas (FX1)-(FX41), that do not have a spacer moiety.

As used herein, "attaching moiety" refers to a component provided to attach one or more R groups directly or indirectly to the central diaza ring in compounds of the invention. In some embodiments, any one of $W^1$-$W^6$ in formulas (FX1)-(FX35) is an attaching moiety. Attaching moieties may connect to the central diaza ring directly or may connect to the central diaza ring via a spacer moiety. Attaching moieties in some embodiments provide a means of derivatizing the central diaza ring so as to provide optical agents having useful overall chemical optical, physical and/or pharmakientic properties, including targeting and molecular recognition functionality. Attaching moieties useful in the present invention include, but are not limited to, a single bond, —$(CH_2)_n$—, —$(HCCH)_n$—, —O—, —S—, —SO—, —$SO_2$—, —$SO_3$—, —$OSO_2$—, —$NR^6$—, —CO—, —COO—, —OCO—, —OCOO—, —$CONR^7$—, —$NR^8CO$—, —$OCONR^9$—, —$NR^{10}COO$—, —$NR^{11}CONR^{12}$—, or —$NR^{13}CSNR^{14}$—, wherein each n is independently an integer selected from the range of 1 to 10.

As used herein, an "electron withdrawing group" (abbreviated as "EWG") refers to a chemical group that draws electrons or electron density from a center, such a $C_5$-$C_{30}$ aryl or $C_5$-$C_{30}$ heteroaryl of the diaza compounds of the invention. In some embodiments, the electron withdrawing group(s) are independently selected from cyano (—CN), carbonyl (—CO), carboxylate (—$CO_2R^a$), halo (—F, —Cl, —Br, —I, —At), carbamate (—$CONR^bR^c$), acyl (—$COR^d$), nitro (—$NO_2$), sulfinyl (—$SOR^e$), sulfonyl (—$SO_2R^f$, —$SO_2OR^g$, and —$PO_3R^hR^i$, wherein in the context of this description, $R^a$-$R^i$ are independently selected to enhance biological and/or physiochemical properties of the optical agents of the invention. In some instances, $R^a$-$R^i$ are independently selected from any one of a hydrogen atom, an anionic functional group (e.g., carboxylate, sulfonate, sulfate, phosphonate or phosphate) and a hydrophilic functional group (e.g., hydroxyl, carboxyl, sulfonyl, sulfonato or phosphonato). In other instances, $R^a$-$R^i$ are independently selected from hydrogen, $C_{1-10}$ alkyl, aryl, heteroaryl, —$(CH_2)_nOH$, —$(CH_2)_nCO_2H$, —$(CH_2)_nSO_3H$, —$(CH_2)_nSO_3^-$, —$(CH_2)_nOSO_3H$, —$(CH_2)_nOSO_3^-$, —$(CH_2)_nNHSO_3H$, —$(CH_2)_nNHSO_3^-$, —$(CH_2)_nPO_3H_2$, —$(CH_2)_nPO_3H^-$, —$(CH_2)_nPO_3^=$, —$(CH_2)_nOPO_3H_2$, —$(CH_2)_nOPO_3H^-$ and —$(CH_2)_nOPO_3^=$, wherein n is an integer from 1 to 10. In one example of this embodiment, the EWG(s) are independently selected from is —CN, halo, —$CO_2R^{76}$, —$COR^{77}$, —$NO_2$, —$SO_2R^{78}$, or —$SO_2NR^{79}R^{80}$, wherein each of $R^{76}$-$R^{80}$ is independently H or $C_1$-$C_{10}$ alkyl. In an embodiment, an EWG is located at the terminus of a substituent arm of a $C_5$-$C_{30}$ aryl or $C_5$-$C_{30}$ heteroaryl of the diaza compounds of formulas (FX1)-(FX41).

As used herein, an "electron donating group" (abbreviated as "EDG") refers to a chemical group that releases electrons or electron density to a center, such as a $C_5$-$C_{30}$ aryl or $C_5$-$C_{30}$ heteroaryl of the diaza compounds of the invention. In some embodiments, the electron donating group(s) are independently selected from $C_1$-$C_{10}$ alkyl, $C_5$-$C_{10}$ aryl, —$(CH_2)_zOH$, —$OR^j$, —$SR^k$, —$NR^lR^m$, —$N(R^n)COR^o$, and —$P(R^p)$, wherein in the context of this description, $R^j$-$R^p$ are independently selected to enhance biological and/or physiochemical properties of the optical agents of the invention and wherein z is selected from the range of 1 to 10. In some instances, $R^j$-$R^p$ are independently selected from any one of a hydrogen atom, an anionic functional group (e.g., carboxylate, sulfonate, sulfate, phosphonate or phosphate) and a hydrophilic functional group (e.g., hydroxyl, carboxyl, sulfonyl, sulfonato or phosphonato). In other instances, $R^j$-$R^p$ are independently selected from hydrogen, $C_{1-10}$ alkyl, aryl, heteroaryl, —$(CH_2)_nOH$, —$(CH_2)_zCO_2H$, —$(CH_2)_zSO_3H$, —$(CH_2)_nSO_3^-$, —$(CH_2)_zOSO_3H$, —$(CH_2)_zOSO_3^-$, —$(CH_2)_zNHSO_3H$, —$(CH_2)_zNHSO_3^-$, —$(CH_2)_zPO_3H_2$, —$(CH_2)_zPO_3H^-$, —$(CH_2)_zPO_3^=$, —$(CH_2)_zOPO_3H_2$, —$(CH_2)_zOPO_3H^-$ and —$(CH_2)_zOPO_3^=$ where z is an integer from 1 to 10. In one example of this embodiment, the EDG(s) are independently $C_1$-$C_6$ alkyl, —$OR^{70}$, —$SR^{71}$, —$NR^{72}R^{73}$, or —$NR^{74}COR^{75}$, wherein each of $R^{70}$-$R^{75}$ is independently H or $C_1$-$C_{10}$ alkyl. In an embodiment, an EDG is located at the terminus of a substituent arm of a $C_5$-$C_{30}$ aryl or $C_5$-$C_{30}$ heteroaryl of the diaza compounds of formulas (FX1)-(FX41) of the invention.

In embodiments, two substituents, such as EDG and EWG substituents, on a compound of the invention can act in what is known as a "push-pull" arrangement. In embodiments of the "push-pull" arrangement, the electron density of the compound or a portion thereof, such as an aryl or heteroaryl group, is polarized due in part to the location of an EWG and EDG on the compound. In embodiments of the "push-pull" arrangement, an EWG is positioned at a terminus of a substituent arm of the structure and an EDG is positioned at a terminus of a different substituent arm of the structure. In embodiments of the "push-pull" arrangement, an EWG is positioned at one end of a π bond and an EDG is positioned at the other end of a π bond. In an embodiment, an EWG is positioned pars- to an EDG in a six-membered ring structure. In an embodiment, an EWG is positioned trans- to an EDG in an alkylene structure. In some embodiments, compounds having the "push-pull" arrangement exhibit a shift in the optical absorbance and emission spectrum as compared to compounds not having the "push-pull" arrangement.

When used herein, the terms "diagnosis", "diagnostic" and other root word derivatives are as understood in the art and are further intended to include a general monitoring, characterizing and/or identifying a state of health or disease. The term is meant to encompass the concept of prognosis. For example, the diagnosis of cancer can include an initial determination and/or one or more subsequent assessments regardless of the outcome of a previous finding. The term does not necessarily imply a defined level of certainty regarding the prediction of a particular status or outcome.

Amino acids include glycine, alanine, valine, leucine, isoleucine, methionine, praline, phenylalanine, tryptophan, asparagine, glutamine, glycine, serine, threonine, serine, rhreonine, asparagine, glutamine, tyrosine, cysteine, lysine, arginine, histidine, aspartic acid and glutamic acid. As used herein, reference to "a side chain residue of a natural α-amino acid" specifically includes the side chains of the above-referenced amino acids.

Methods of this invention comprise the step of administering an "effective amount" of the present diagnostic and therapeutic compositions, formulations and preparations containing the present compounds or compositions, to diagnose, image, monitor, evaluate, treat, reduce, alleviate, ameliorate or regulate a biological condition and/or disease state in a patient. The term "effective amount," as used herein, refers to the amount of the diagnostic and therapeutic formulation, that, when administered to the individual is effective to diagnose, image, monitor, evaluate, treat, reduce alleviate, ameliorate or regulate a biological condition and/or disease state. As is understood in the art, an effective amount of a given composition or formulation will depend at least in part upon the mode of administration (e.g. intravenous, oral, topical administration), any carrier or vehicle employed, and the specific individual to whom the formulation is to be administered (age, weight, condition, sex, etc.). The dosage requirements needed to achieve the "effective amount" vary with the particular formulations employed, the route of administration, and clinical objectives. Based on the results obtained in standard pharmacological test procedures, projected daily dosages of active compound or composition can be determined as is understood in the art.

In an embodiment, an effective amount of a compound or composition of the invention is a therapeutically effective amount. As used herein, the phrase "therapeutically effective" qualifies the amount of compound or composition administered in the therapy. This amount achieves the goal of ameliorating, suppressing, eradicating, preventing, reducing the risk of, or delaying the onset of a targeted condition. In an embodiment, an effective amount of a compound or composition of the invention is a diagnostically effective amount. As used herein, the phrase "diagnostically effective" qualifies the amount of compound or composition administered in diagnosis, for example of a disease state or other pathological condition. The amount achieves the goal of being detectable while avoiding adverse side effects found with higher doses. In an embodiment, an active ingredient or other component is included in a therapeutically acceptable amount. In an embodiment, an active ingredient or other component is included in a diagnostically acceptable amount.

It is contemplated that the compounds and pharmaceutically acceptable salts of the invention can be used as part of a combination. The term "combination" means the administration of two or more compounds directed to a target condition. The treatments of the combination generally can be co-administered in a simultaneous manner. Two compounds can be co-administered as, for example: (a) a single formulation (e.g., a single capsule) having a fixed ratio of active ingredients; or (b) multiple, separate formulations (e.g., multiple capsules) for each compound. The treatments of the combination can alternatively (or additionally) be administered at different times.

In certain embodiments, the invention encompasses administering optical agents useful in the invention to a patient or subject. A "patient" or "subject", used equivalently herein, refers to an animal. In particular, an animal refers to a mammal, preferably a human. The subject can either: (1) have a condition able to be monitored, diagnosed, prevented and/or treated by administration of an optical agent of the invention; or (2) is susceptible to a condition that is able to be monitored, diagnosed, prevented and/or treated by administering an optical agent of the invention.

When used herein, the terms "diagnosis", "diagnostic" and other root word derivatives are as understood in the art and are further intended to include a general monitoring, characterizing and/or identifying a state of health or disease. The term is meant to encompass the concept of prognosis. For example, the diagnosis of cancer can include an initial determination and/or one or more subsequent assessments regardless of the outcome of a previous finding. The term does not necessarily imply a defined level of certainty regarding the prediction of a particular status or outcome.

As defined herein, "administering" means that a compound or formulation thereof of the invention, such as an optical agent, is provided to a patient or subject, for example in a therapeutically effective amount. The invention includes methods for a biomedical procedure wherein a therapeutically or diagnostically effective amount of a compound having any one of formulas (FX1)-(FX41) is administered to a patient in need of treatment, for example to a patient undergoing treatment for a diagnosed diseased state including cancer, inflammation and vascular diseases. Administering can be carried out by a range of techniques known in the art including parenteral administration including intravenous, intraperitoneal or subcutaneous injection or infusion, oral administration, topical or transdermal absorption through the skin, or by inhalation, for example. The chosen route of administration may depend on such factors as solubility of the compound or composition, location of targeted condition, and other factors which are within the knowledge of one having ordinary skill in the relevant art.

"Topical administration" includes the use of transdermal administration, such as transdermal patches or iontophoresis devices.

"Parenteral administration" includes subcutaneous injections, intravenous injections, intraarterial injections, intraorbital injections, intracapsular injections, intraspinal injections, intraperitoneal injections, intramuscular injections, intrasternal injections, and infusion. Dosage forms suitable for parenteral administration include solutions, suspensions, dispersions, emulsions, and any other dosage form that can be administered parenterally.

As used herein, the term "controlled-release component" refers to an agent that facilitates the controlled-release of a compound including, but not limited to, polymers, polymer matrices, gels, permeable membranes, liposomes, microspheres, or the like, or any combination thereof. Methods for producing compounds in combination with controlled-release components are known to those of skill in the art.

As used herein, the term "pharmaceutically acceptable" means approved by a regulatory agency of an appropriate federal or state government; or listed in the U.S. Pharmacopoeia or other generally recognized pharmacopoeia for use in animals, and more particularly in humans; or does not impart significant deleterious or undesirable effect on a subject to whom it is administered and in the context in which it is administered.

As will be clear to those of ordinary skill in the art, the groups and structures described herein as portions of the compounds of the invention may be defined as if they are separate valence-satisfied chemical structures. It is intended that when a group is described or shown as being a substituent of another group, that the group be viewed as having a valency to allow this binding to occur.

The invention is further detailed in the following Examples, which are offered by way of illustration and are not intended to limit the scope of the invention in any manner.

EXAMPLE 1

Compounds for Phototherapy 1.a Type 1 Phototherapeutic Agents

The invention provides Type 1 phototherapeutic agents, including compositions, preparations and formulations, and methods of using and making Type 1 phototherapeutic agents. Type 1 phototherapeutic agents of the invention include alicyclic diaza compounds, including 1,2 diaza heterocyclic compounds, having a photolabile N—N bond directly or indirectly linked to a $C_5$-$C_{30}$ aryl or $C_5$-$C_{30}$ heteroaryl, optionally $C_5$-$C_{20}$ aryl or $C_5$-$C_{20}$ heteroaryl, optionally $C_5$-$C_{10}$ aryl or $C_5$-$C_{10}$ heteroaryl. Incorporation of a $C_5$-$C_{30}$ aryl or $C_5$-$C_{30}$ heteroaryl, comprising aromatic and/or heterocyclic aromatic groups in some compounds provides a chromophore moiety capable of absorption of electromagnetic radiation, preferably for some applications electromagnetic radiation having wavelengths in the visible (e.g. 350 nm to 750 nm) and NIR regions (e.g., 750-1300 nm) of the electromagnetic spectrum. The $C_5$-$C_{30}$ aryl or $C_5$-$C_{30}$ heteroaryl group(s) of some compositions of the invention function as an aromatic antenna group for coupling energy from incident electromagnetic radiation into the phototherapeutic agent. In some phototherapeutic agents of the present invention, energy coupled into the phototherapeutic agent is subsequently transferred to the surroundings to achieve a desired therapeutic outcome. Incorporation of an aromatic antenna group comprising a $C_5$-$C_{30}$ aryl or $C_5$-$C_{30}$ heteroaryl having one or more aromatic and/or heterocyclic aromatic groups is useful in some embodiments for initiating cleavage of a photolabile N—N bond of an alicyclic diaza ring upon absorption of electromagnetic radiation and subsequent internal energy transfer process(es). Cleavage of the photolabile N—N bond generates one or more reactive species capable of causing localized tissue damage, such as cell death.

Figure 1B:
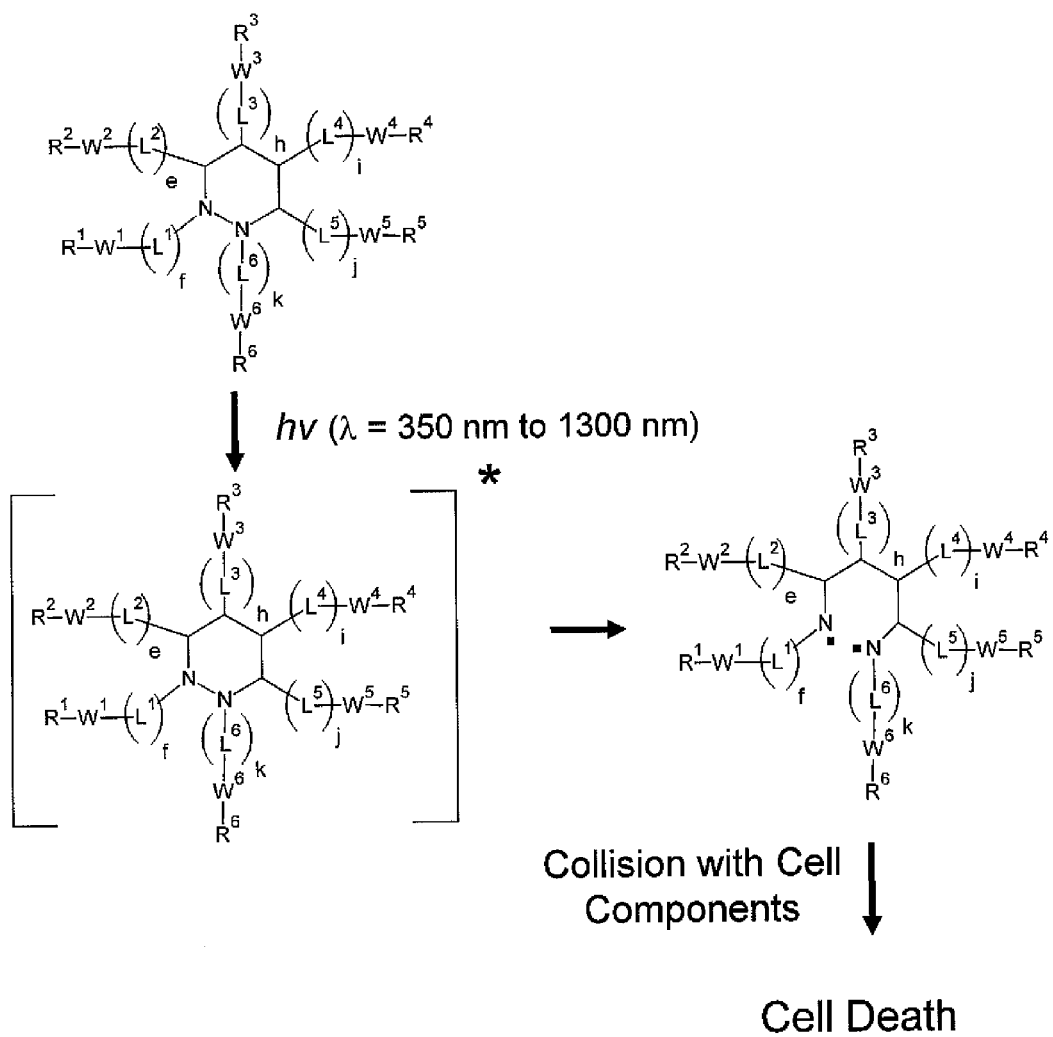
Figure 1C:
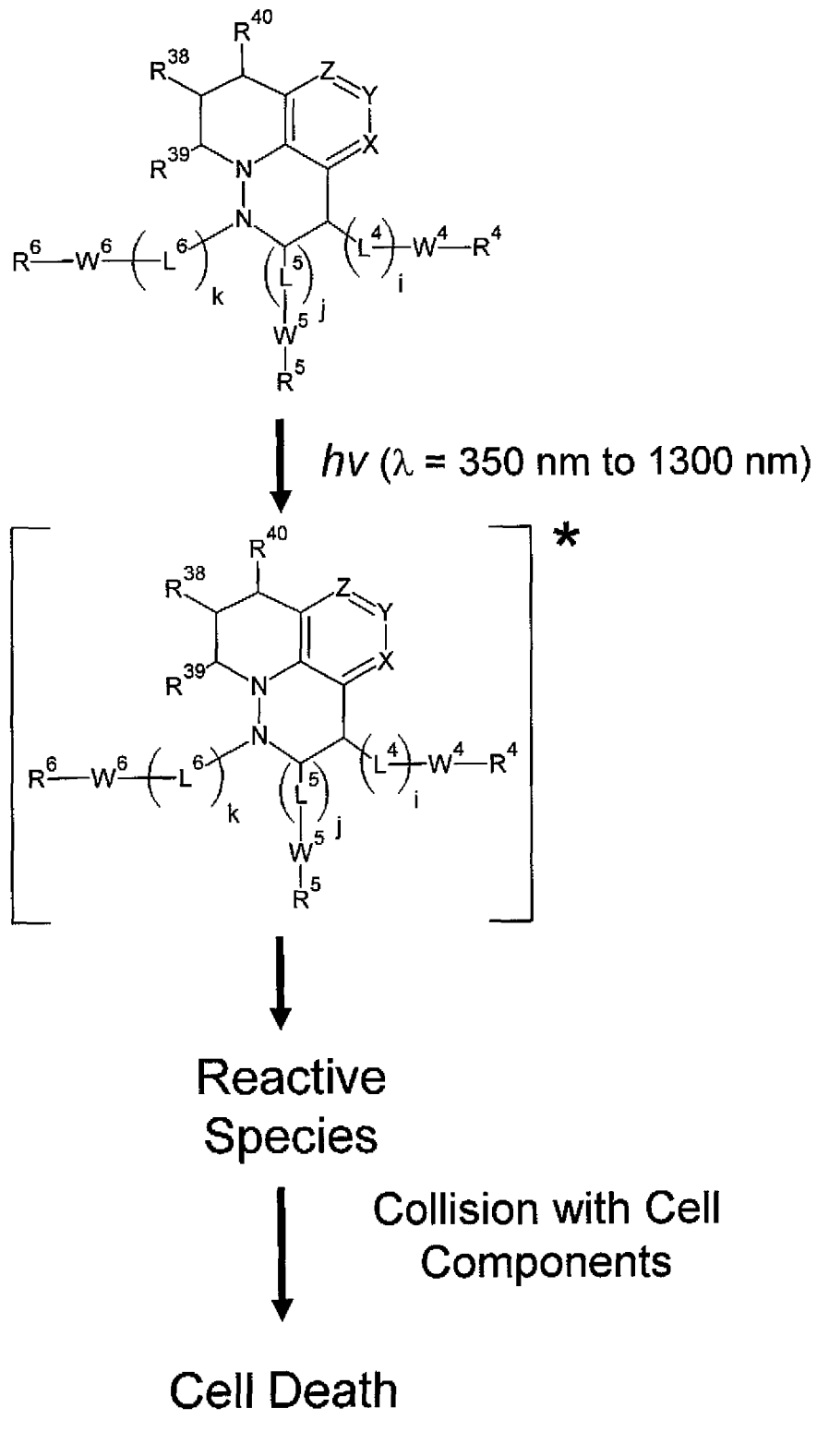
Figure 1D:
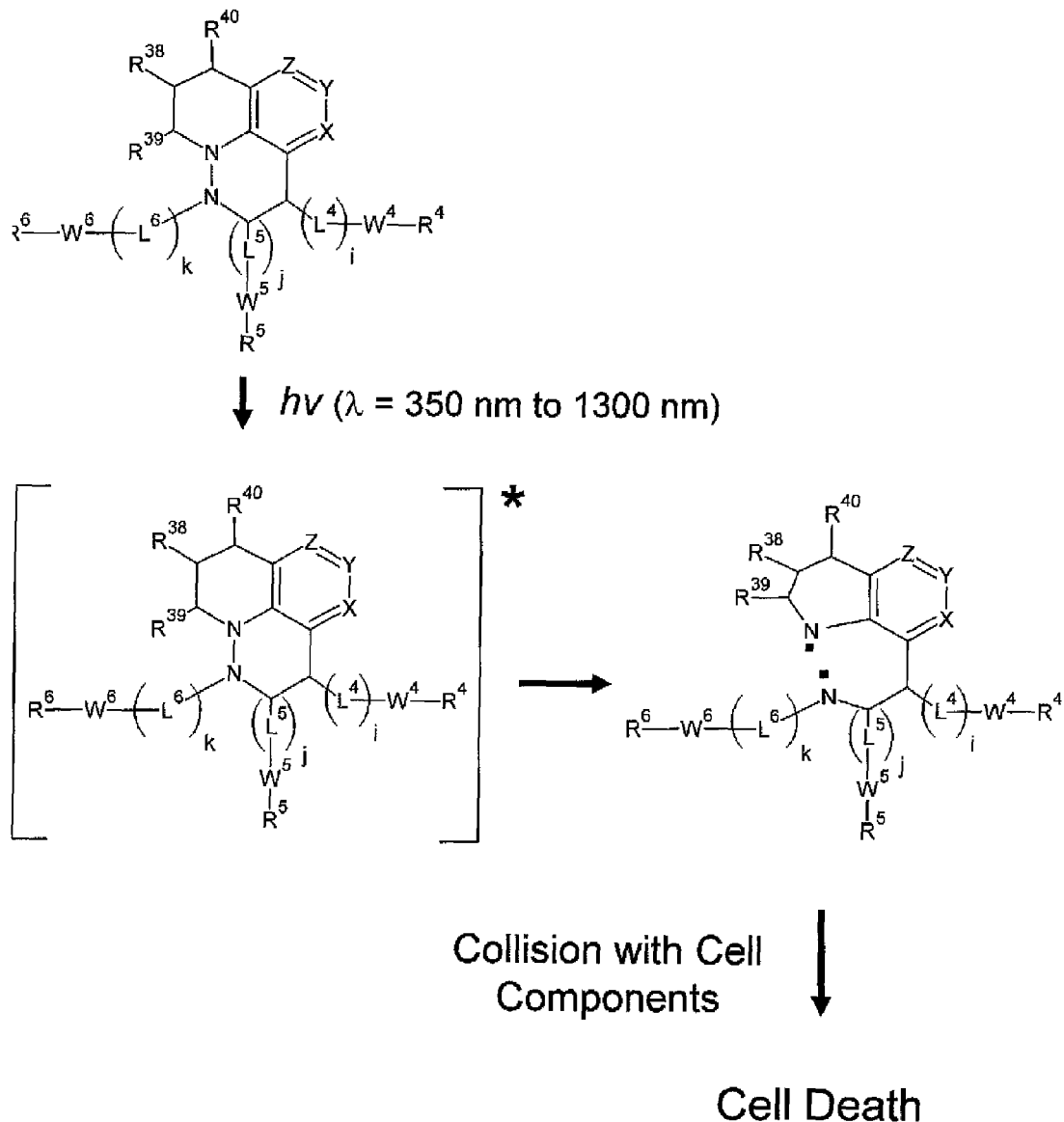

Some compounds of the invention operate through the Type 1 phototherapy mechanism as schematically illustrated in FIGS. 1A-1D wherein the N—N bond of a central diaza ring of a photosensitizer undergoes cleavage upon photoactivation, thereby producing reactive species. FIGS. 1A-1D provides schematic representations of reaction mechanisms for phototherapeutic agents having an alicyclic diaza ring with a photolabile N—N bond, wherein exposure to electromagnetic radiation activates the phototherapeutic agent, for example, resulting in bond cleavage and generating reactive species. FIGS. 1A and 1B provide schematic representations of reaction mechanisms for phototherapeutic agents comprising a compound having formula (FX5), and FIGS. 1C and 1D provide schematic representations of reaction mechanisms for phototherapeutic agents comprising a compound having formula (FX30). As schematically represented by the arrow and hv in FIGS. 1A-1D, compounds of the present invention are photoactivated by exposure to visible or near infrared electromagnetic radiation, for example electromagnetic radiation having wavelengths ranging from 350 nm to 1300 nm. Absorption of at least a portion of the applied electromagnetic radiation generates a therapeutically effective amount of photoactivated phototherapeutic agent, which is schematically represented in FIGS. 1A-1D by the compound provided in brackets with a star. Activation of the phototherapeutic agent may occur via a single photon absorption process, a mulitphoton absorption process or a combination of via a single photon absorption process and a mulitphoton absorption process. The activated photosensitizer subsequently undergoes processes, such as internal energy transfer and/or bond cleavage processes, resulting in formation of reactive species capable of causing a desired therapeutic result. Reactive species generated by the compounds of the invention may include free radicals, intramolecular diradicals, ions, electrons, electrophiles, nitrene, vibrationally excited species, and translationally excited species. As illustrated in FIGS. 1B and 1D, excitation of the photosensitizer in these embodiments causes cleavage of the N—N bond of the central diaza ring, thereby generating free radicals. In the mechanism shown in FIGS. 1B and 1D excitation of a $C_5$-$C_{30}$ aryl or $C_5$-$C_{30}$ heteroaryl results in rapid intramolecular energy transfer to the photolabile N—N bond resulting in bond cleavage and radical formation. The coupling between the $C_5$-$C_{30}$ aryl or $C_5$-$C_{30}$ heteroaryl and the central diaza ring having the N—N bond may be selected to enhance the intramolecular energy transfer process(es) and provide efficient and selective photoinitated bond cleavage. In some embodiments, for example, the central diaza ring is directly coupled to one or more rings of an aromatic group or heterocyclic aromatic group of a $C_5$-$C_{30}$ aryl or $C_5$-$C_{30}$ heteroaryl. In some embodiments, the reactive species generated upon excitation of the photosensitizer collide, react with, or otherwise interact with cell components of a target organ or tissue class, thereby resulting in cell death.

Type 1 phototherapeutic agents useful for certain phototherapy applications incorporate one or more $C_5$-$C_{30}$ aryl or $C_5$-$C_{30}$ heteroaryl, including aromatic groups, heterocyclic aromatic groups, polycyclic aromatic groups and polycyclic heterocyclic aromatic groups, that absorb strongly in the visible and/or NIR region of the electromagnetic spectrum. $C_5$-$C_{30}$ aryl and $C_5$-$C_{30}$ heteroaryl groups providing effective photoactivation by electromagnetic radiation having wavelengths selected over the range of 600 nm to 1300 nm include, but are not limited to, azulenes, anthracenes, pyrazines, pyridazines, quinolines, quinoxalines, courmarins, phenoxazines, phenothiazines, rhodamines, and the like. The invention further includes phototherapeutic agents having one or more $C_5$-$C_{30}$ aryl or $C_5$-$C_{30}$ heteroaryl comprising aromatic group(s) and heterocyclic aromatic group(s) that are functionalized by incorporation of heteroatom ring members and substituents on the ring structure(s) providing excitation wavelength selection and/or tunability. In some embodiments, for example, the $C_5$-$C_{30}$ aryl or $C_5$-$C_{30}$ heteroaryl comprises one or more aromatic or heterocyclic aromatic groups independently having one or more electron donating and/or electron withdrawing groups provided as ring substituents for providing selected excitation characteristics, such as a selected absorption spectrum and/or strong absorption in the visible and/or NIR regions.

Selection of $R^1$-$R^{43}$ in the compounds of any one of formulae (FX1)-(FX41) establishes, at least in part, the physical, chemical, optical and/or pharmacokinetic properties of optical agents for the present compositions and methods. In some embodiments, for example $R^1$-$R^{43}$ are selected to provide optical properties supporting and enabling use of these compositions in phototherapeutic methods, such as providing one or more of the following: (i) large extinction coefficients; (ii) strong absorption in the visible and/or infrared regions of the electromagnetic spectrum (e.g., 350 to 1300 nanometers, preferably for some applications 350-900 nanometers); and (iii) a large quantum yield for the production of reactive species, such as free radicals or ions, capable of causing photoactivation initiated tissue damage. Selection of the composition of $R^1$-$R^{43}$ in the compounds of any one of formulae (FX1)-(FX41) may also be based, at least in part, on a number of pharmacokinetic and physical properties supporting effective delivery and clearance of the optical agents of the present methods and compositions. Such factors may include solubility, toxicity, immune response, biocompatibility, and bioclearance considerations. In some embodiments, any one of $R^1$-$R^{43}$ comprises a hydrophilic group, a lipophilic group, hydrophobic group, or an amphiphilic group. In an embodiment, at least one of $R^1$-$R^6$, $L^1$-$L^6$ and $R^{38}$-$R^{43}$ is a substituent comprising poly(ethylene glycol) (PEG; —$(CH_2OCH_2)_b$—), or a derivative of PEG.

In an embodiment, a phototherapeutic agent of the invention incorporates one or more aromatic groups and/or heterocyclic aromatic groups that are derivatized by the addition of at least one electron withdrawing group and at least one electron donating group bonded directly or indirectly to a carbon atom of the ring structure. In an embodiment, for example, one or more the electron withdrawing (EWG) and electron donating (EDG) group(s) are directly attached to the ring structure of an aromatic group. In another embodiment, EWG and EDG are indirectly attached to the ring structure of the aromatic group through an unsaturated spacer that is in conjugation with the double bonds of a $C_5$-$C_{30}$ aryl or $C_5$-$C_{30}$ heteroaryl group. Electron donating and withdrawing groups in these dye compositions may be positioned ortho, meta or para to each other with respect to the to the ring structure of the aromatic group. In some embodiments, for example, two electron withdrawing groups are positioned pare to each other on the ring structure of the aromatic group and two electron donating groups are positioned pare to each other on the ring structure of the aromatic group. In some embodiments, electron withdrawing groups and electron donating groups are positioned so as to make the overall compound symmetrical.

Optical agents of the invention support a broad therapeutic platform useful for a variety of in vivo phototherapy procedures, for example for the treatment of cancer, stenosis, inflammation, infection, vascular diseases, and arthritis. Optical agents of the invention are optionally multifunctional agents capable of providing a useful combination of photodiagnostic, phototherapeutic, molecular recognition and/or targeting functionality. In an embodiment, for example, a dye component is incorporated into the phototherapeutic agent of the present compositions for imparting useful optical functionality, for example by functioning as an optical absorber, chromophore, and/or fluorophore. This functionality is useful for targeted administration and excitation of the therapeutic agent. Optionally, optical agents of the invention further comprise a targeting component, such as a targeting ligand. In an embodiment, for example, an optical agent of the invention comprises a targeting ligand integrated with a photosensitizer component to access enhanced administration, delivery and photoactivation functionality for phototherapy. Optical agents and bioconjugates thereof are provided having one or more targeting ligands covalently bonded to or non-covalently associated with the phototherapeutic agents of the present invention, thereby providing specificity for administering, targeting, delivery and/or localizing an optical agent to a specific biological environment, such as a target tissue such as a specific organ, tissue, cell type or tumor site.

In the compounds of formulae (FX1)-(FX41), Bm is a targeting ligand, optionally providing molecular recognition functionality. In some embodiments, the targeting ligand is a particular region of the compound that is recognized by, and binds to, the target site on the organ, tissue, tumor or cell.

Targeting ligands are often, but not always, associated with biomolecules or fragments thereof which include hormones, amino acids, peptides, peptidomimetics, proteins, nucleosides, nucleotides, nucleic acids, enzymes, carbohydrates, glycomimetics, lipids, albumins, mono- and polyclonal antibodies, receptors, inclusion compounds such as cyclodextrins, and receptor binding molecules. Specific examples of biomolecules include steroid hormones for the treatment of breast and prostate lesions, somatostatin, bombesin, and neurotensin receptor binding molecules for the treatment of neuroendocrine tumors, cholecystekinin receptor binding molecules for the treatment of lung cancer; heat sensitive bacterioendotoxin (ST) receptor and carcinoembryonic antigen (CEA) binding molecules for the treatment of colorectal cancer, dihydroxyindolecarboxylic acid and other melanin producing biosynthetic intermediates for melanoma, integrin receptor and atheroscleratic plaque binding molecules for the treatment of vascular diseases, and amyloid plaque binding molecules for the treatment of brain lesions. Biomolecules for use in the invention may also include synthetic polymers. Examples of synthetic polymers include polyaminoacids, polyols, polyamines, polyacids, oligonucleotides, aborols, dendrimers, and aptamers. Coupling of phototherapeutic and/or diagnostic agents to biomolecules can be accomplished by methods well known in the art as disclosed in Hnatowich et al., *Radioactive Labeling of Antibody. A simple and efficient method. Science,* 1983, 220, 613-615; A. Pelegrin et al., *Photoimmunodiagnosis with antibody-fluorescein conjugates: in vitro and in vivo preclinical studies. Journal of Cellular Pharmacology,* 1992, 3, 141-145; and U.S. Pat. No. 5,714,342, each of which are expressly incorporated by reference herein in their entirety. Successful specific targeting of fluorescent dyes to tumors using antibodies and peptides for diagnostic imaging of tumors has been demonstrated, for example, S. A. Achilefu et al., *Novel receptor-targeted fluorescent contrast agents for in vivo tumor imaging, Investigative Radiology,* 2000, 35(8), 479-485; B. Ballou et al., *Tumor labeling in vivo using cyanine-conjugated monoclonal antibodies,* Cancer Immunology and Immunotherapy, 1995, 41, 247-263; K. Licha et al., *New contrast agent for optical imaging: acid-cleavable conjugates of cyanine dyes with biomolecules,* In Biomedical Imaging: Reporters, Dyes, and Instrumentation, D. J. Bomhop, C. Contag, and E. M. Sevick-Muraca (Eds.), Proceedings of SPIE, 1999, 3600, 29-35, each of which are expressly incorporated by reference herein in their entirety. Therefore, the inventive receptor-targeted phototherapeutic agents are expected to be effective in the treatment of various lesions.

The optical agents of this example may contain additional functionalities that can be used to attach various types of biomolecules, synthetic polymers, and organized aggregates for selective delivery to various organs or tissues of interest. Examples of synthetic polymers include polyaminoacids, polyols, polyamines, polyacids, oligonucleotides, aborols, dendrimers, and aptamers. The invention includes, but is not limited to, phototherapeutic agents comprising a photosensitizer—biomolecule conjugate which provide advantages over nonspecific phototherapeutic agents or the conjugation of photosensitizers to very large biomolecules. These conjugates provide enhanced localization and rapid visualization of tumors which is beneficial for both diagnosis and therapy. The agents are rapidly cleared from blood and non-target tissues so there is less concern for accumulation and for toxicity. A variety of high purity compounds may be easily synthesized for combinatorial screening of new targets, e.g., to identify receptors or targeting agents, and for the ability to affect the pharmacokinetics of the conjugates by minor structural changes.

In some embodiments, a liposome or micelle may be utilized as a carrier or vehicle for the composition. For example, in some embodiments, a phototherapeutic agent comprise a photosensitizer that may be a part of the lipophilic bilayers or micelle, and the targeting ligand, if present, may be on the external surface of the liposome or micelle. As another example, a targeting ligand may be externally attached to the liposome or micelle after formulation for targeting the liposome or micelle (which contains the inventive phototherapeutic agent/photosensitizer) to the desired tissue, organ, or other site in the body.

1b. Synthesis of Phototherapeutic Agents

Figure 2:
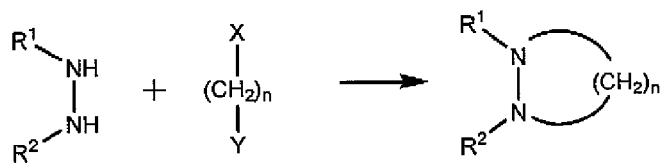
FIG. 2 provides schemes for the general syntheses of 1,2-diaza heterocycles useful as phototherapeutic agents of the present invention.
Figure 2:
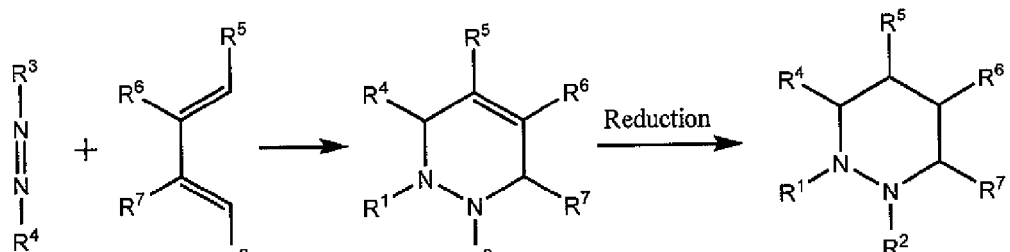

Methods for the synthesis of cyclic 1,2-diaza compounds are known in the art. In general, these compounds may be prepared by the alkylation of hydrazines with dihalides. For 5-membered cyclic diaza compounds, one can employ very well established 1,3-dipolar cycloaddition reactions involving diazoalky and diazoraryl derivatives with alkenes (Padwa, A. Intramolecular 1,3-dipolar cycloadditions. In 1,3-Dipolar Cycloaddition Chemistry, Volume 2, pp. 277-378. Padwa, A. (Ed.)., Wiley Interscience, New York, N.Y. 1984). The 6-membered cyclic 1,2-diaza compounds can be prepared by Diels-Alder reactions involving azo compounds (Gillis, B. T. Azo compounds as dienophiles. In 1,4-Cycloaddition Reactions: The Diels-Alder Reaction in Heterocyclic Syntheses, Hamer, J. (Ed.)., Academic Press, Volume 8, pp. 143-175, New York, N.Y. 1967). FIG. 2 provides schemes for the general syntheses of 1,2-diaza heterocycles useful as phototherapeutic agents of the present invention.

Figure 3:
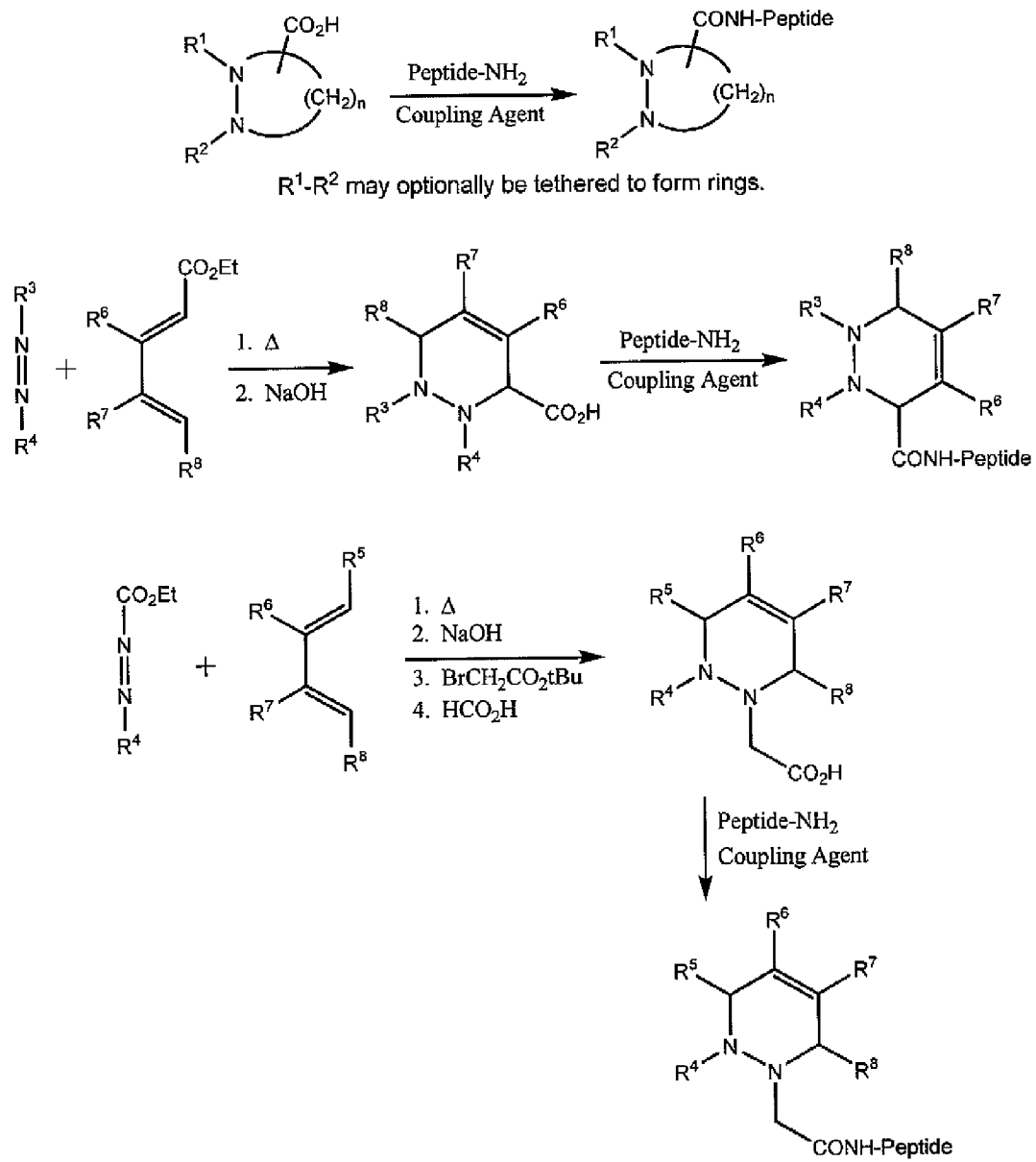
FIG. 3 provides schemes for the general preparation of 1,2-diaza heterocycle bioconjugates useful as phototherapeutic agents of the present invention.

Synthetic pathways for coupling photosensitizers to targeting ligands comprising biomolecules is well known in the art. FIG. 3 provides schemes for the general preparation of 1,2-diaza heterocycle bioconjugates useful as phototherapeutic agents of the present invention.

Figure 4:
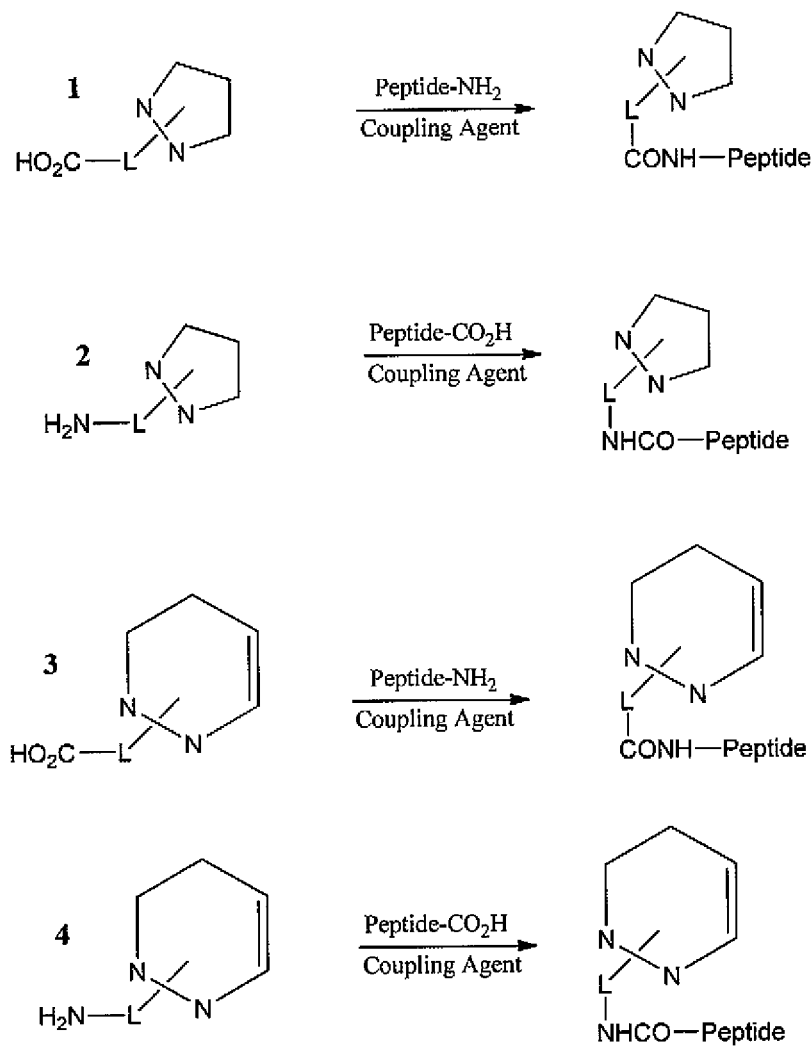
FIG. 4 illustrates examples of peptide coupling reactions useful for synthesis of diaza optical agents of the invention having peptide targeting ligands.
Figure 5A:
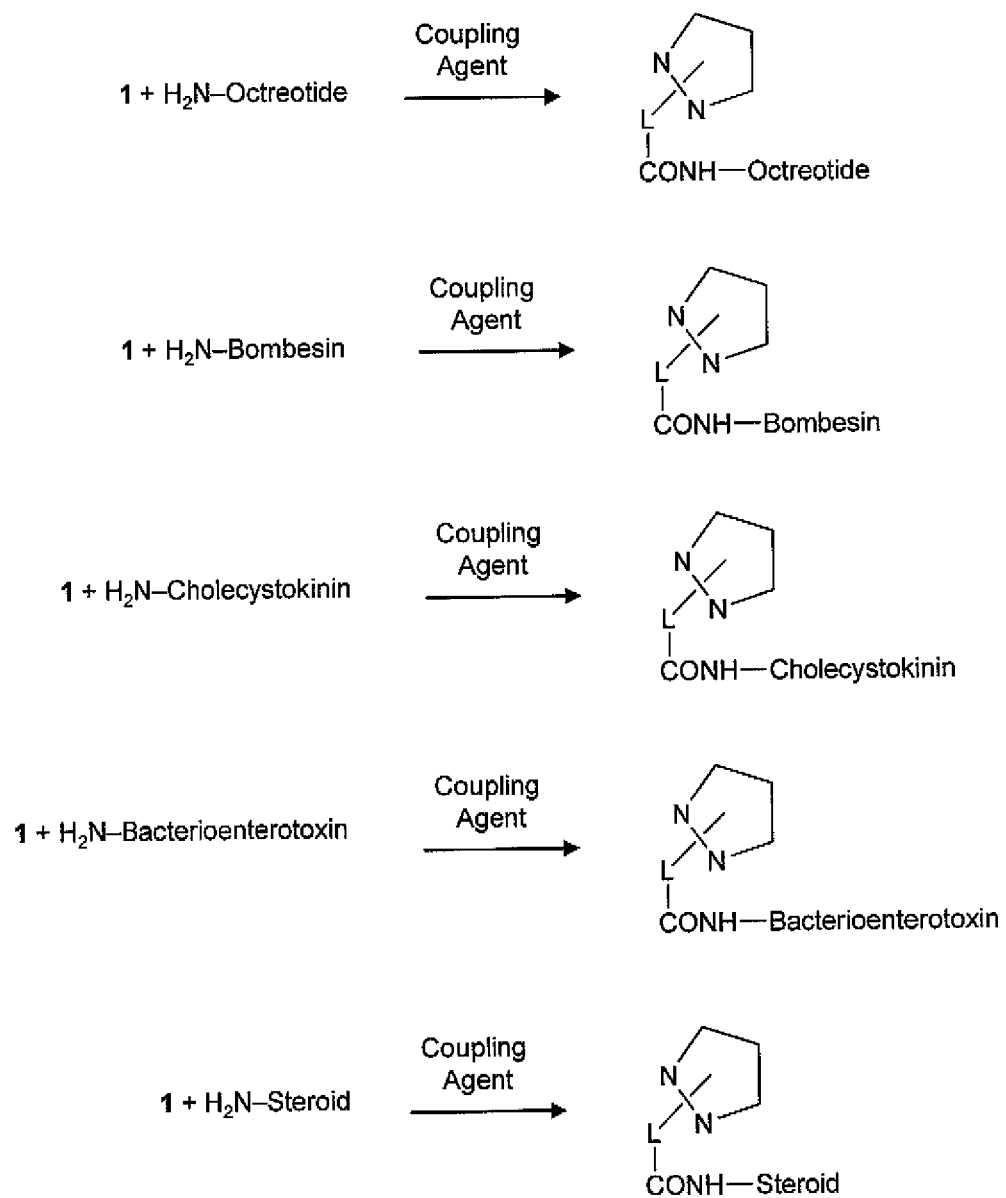
FIGS. 5A-5D illustrate examples of coupling reactions useful for synthesis of diaza optical agents of the invention having specific targeting ligands.
Figure 5B:
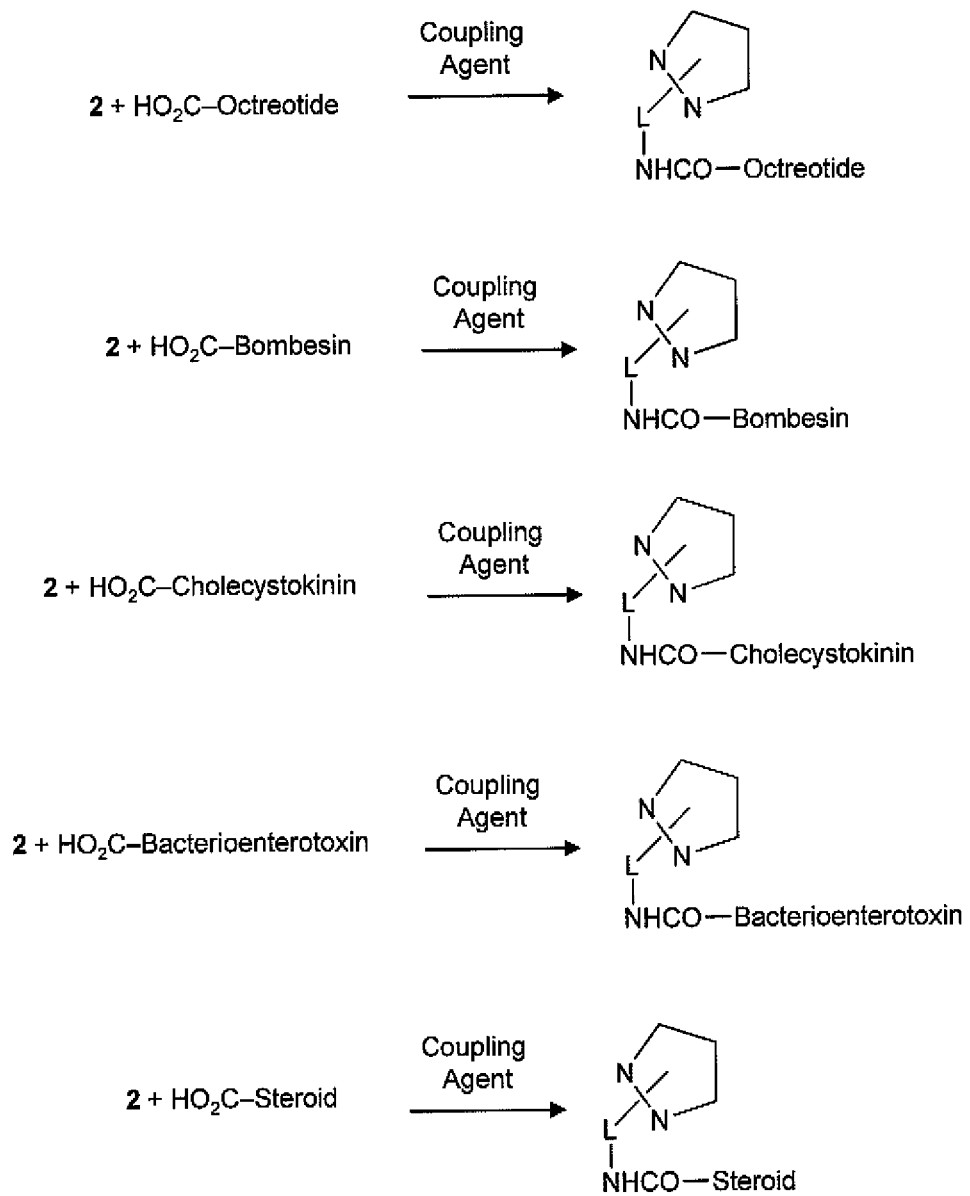
Figure 5C:
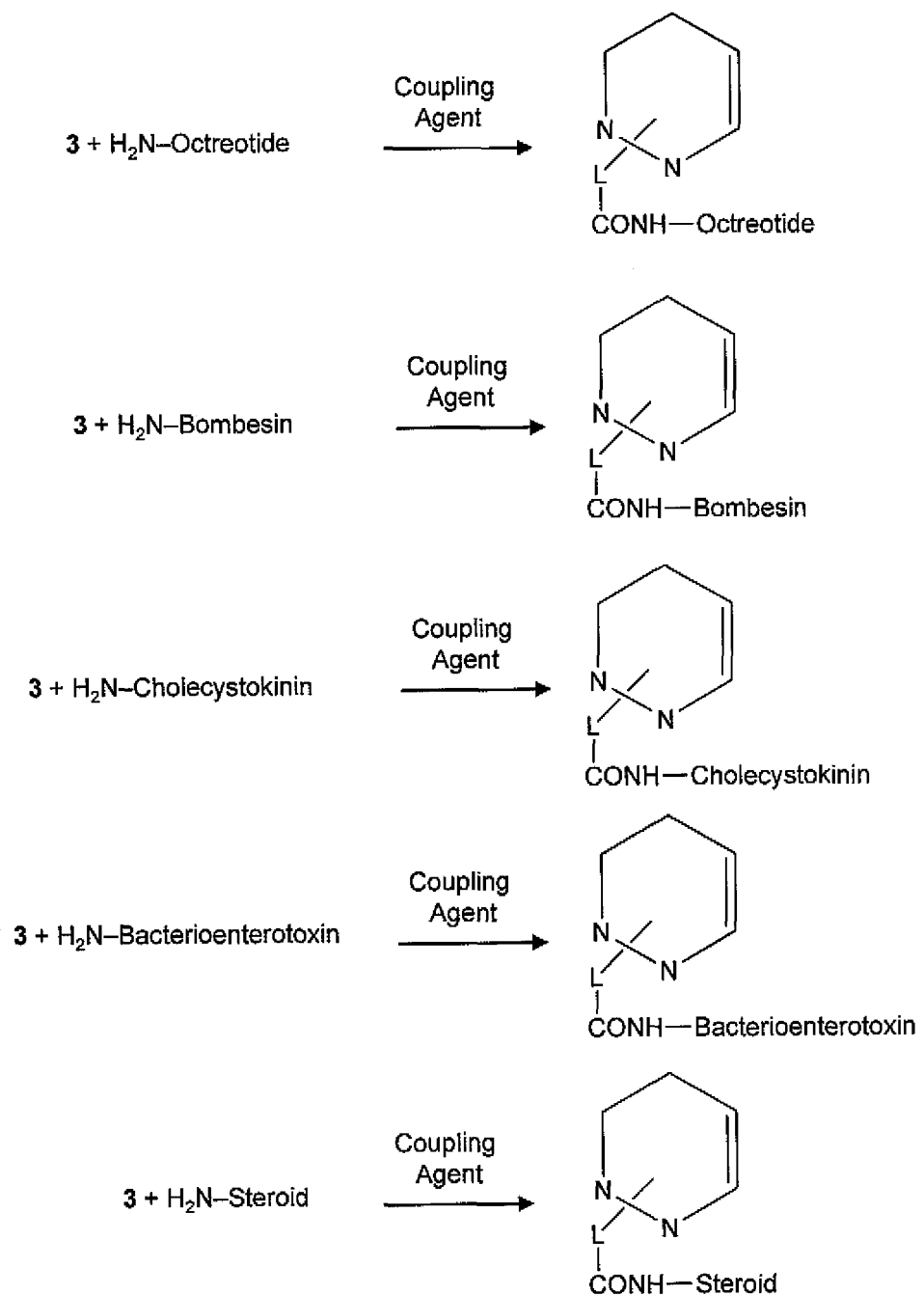
Figure 5D:
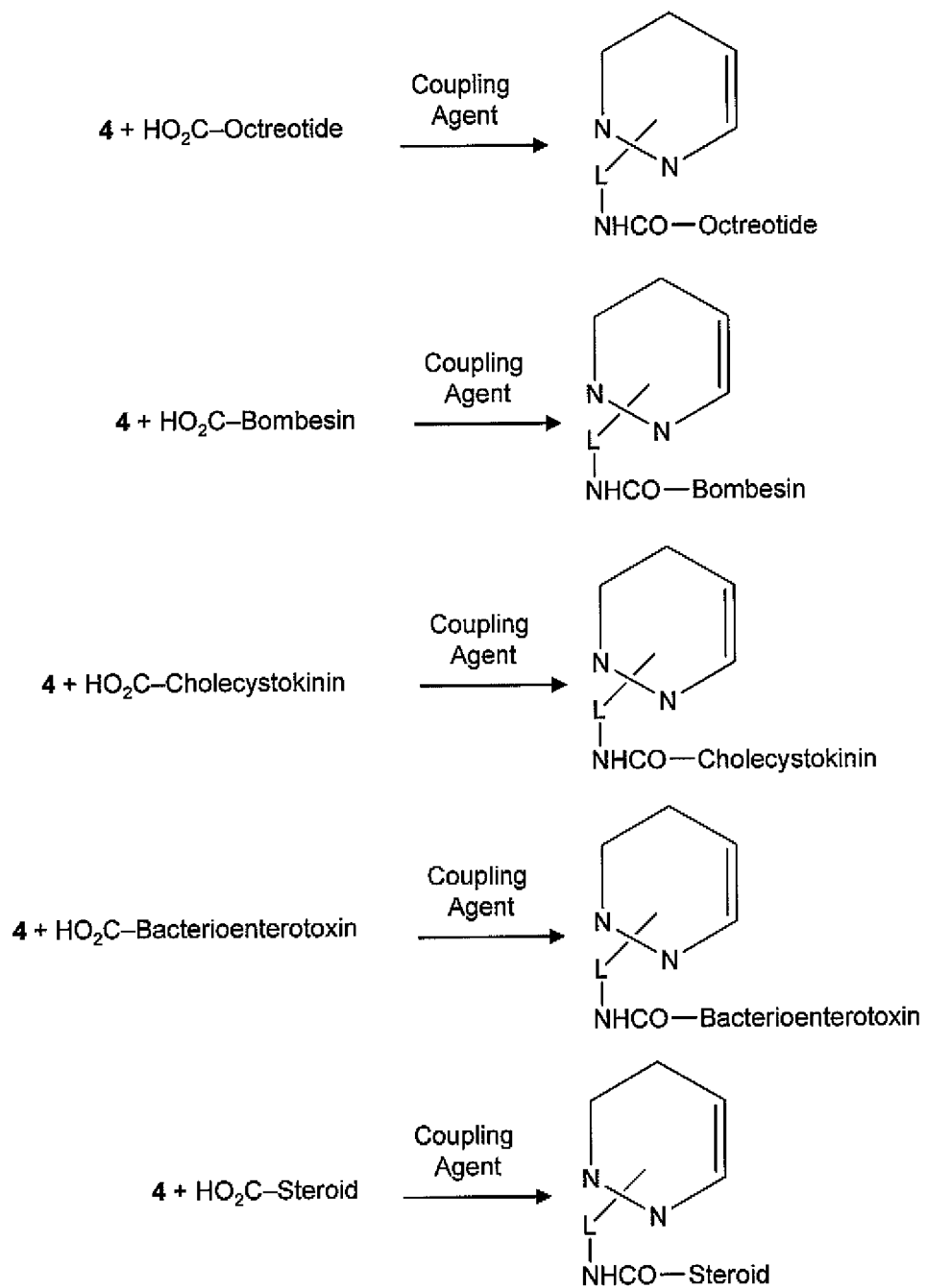

FIG. 4 illustrates examples of peptide coupling reactions useful for synthesis of diaza optical agents of the invention having peptide targeting ligands. As shown in examples in FIG. 4, a peptide targeting ligand may be coupled by reaction with a pendant amine group or carboxylic acid group in the presence of an appropriate coupling agent. FIG. 4 exemplifies such coupling approaches in the context of five-membered and six-membered diaza optical agents of the invention. FIGS. 5A-5D illustrate examples of coupling reactions useful for synthesis of diaza optical agents of the invention having specific targeting ligands. As shown in FIG. 5A, the diaza compound (1) of FIG. 4 having a pendant carboxyl group is linked to octreotide, bombesin, cholecystokinin, bacterioenterotoxin and steroid targeting ligands via formation of an amide bond. As shown in FIG. 5B, the diaza compound (2) of FIG. 4 having a pendant amine group is linked to octreotide, bombesin, cholecystokinin, bacterioenterotoxin and steroid targeting ligands via formation of an amide bond. As shown in FIG. 5C, the diaza compound (3) of FIG. 4 having a pendant carboxyl group is linked to octreotide, bombesin, cholecystokinin, bacterioenterotoxin and steroid targeting ligands via formation of an amide bond. As shown in FIG. 5D, the diaza compound (4) of FIG. 4 having a pendant amine group is linked to octreotide, bombesin, cholecystokinin, bacterioenterotoxin and steroid targeting ligands via formation of an amide bond. In FIGS. 4 and 5A-5D, L is an optional spacer group (e.g., $L^1$-$L^6$). As will be understood by a person having skill in the art, a variety of coupling agents are useful for linking the diaza backbone to the targeting ligands including dicyclohexylcarbodiimide (DCC), 1-ethyl-3-(3-dimethylaminopropyl)carbodiimide (EDC), benzotriazol-1-yl-oxytripyrrolidinophosphonium hexafluorophosphate (PyBOP), disuccinimdyl carbonate, N-hydroxysuccinimide, methylformamide, isobutylchloroformate, etc.

As will be understood by one of skill in the art, the synthetic approaches shown in FIGS. 2, 3, 4 and 5A-5D are applicable to synthesis of other diaza optical agents of the invention, including diaza optical agents having formulas (FX1)-(FX41).

EXAMPLE 1.b(i)

Preparation of 3,4-diaza-3,4-bis(ethxoycarbonyl)-1, 2-dihydrophenanthrene (FX36)

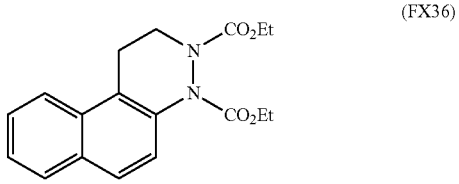 [SMILES: CCOC(=O)N1CCc2c(ccc3ccccc23)N1C(=O)OCC]

(FX36)

A mixture of diethyl azodicarboxylate (DEAD) (2.20 g, 0.01 mot) and 1-vinylnaphthlane (1.32 g, 0.01 mol) in 1,2-dichloroethane (10 mL) is heated under reflux until complete consumption of the starting materials. The solvent is evaporated in vacua and the crude product (FX36) is purified by silica gel flash chromatography.

EXAMPLE 1.b(ii)

Preparation of 3,4-diaza-1,2-dihydro-phenanthrene (FX37)

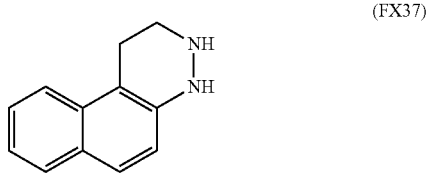 [SMILES: c1ccc2c3c(ccc2c1)NNCC3]

(FX37)

The diethyl ester (FX36) in Example 1.b(i) is added to a solution of potassium hydroxide (1.68 g, 0.03 mol) in methanol (25 mL), and the mixture is heated under reflux for 16 hours. The solvent is evaporated in vacuo and the product (FX37) is purified by silica gel flash chromatography.

EXAMPLE 1.b(iii)

Preparation of 3,4-diaza-3,4-bis(carboxymethyl)-1,2-dihydro-phenanthrene (FX38)

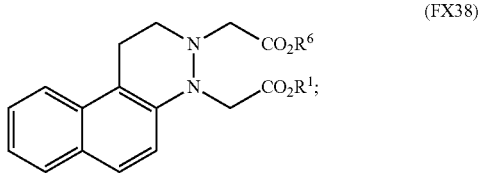

(FX38)

wherein $R^1$ and $R^2$ are each t-Bu or H.

Step 1. A mixture of the hydrazine derivative (FX37) in Example 1.b(ii) (1.84 g, 0.010 mol), t-butyl bromoacetate (4.28 g, 0.021 mol), and finely-ground anhydrous potassium carbonate (4.14 g, 0.030 mol) in glyme (25 mL) is heated under reflux until the starting materials are consumed. The reaction mixture is then filtered to remove potassium bromide and the filtrate evaporated in vacua. The crude product is purified by silica gel flash chromatography to give (FX38) wherein R is t-Bu.

Step 2. A solution of the di-t-butyl ester (FX38) wherein $R^1$ and $R^2$ are each t-Bu in Step 1 (2.01 g, 5 mmol) in 96% formic acid (20 mL) is heated to boiling, allowed to cool to ambient temperature, and kept at ambient temperature for 16 hours. The solved is evaporated in vacua, and the crude product is purified by silica gel flash chromatography or recrystallization to give (FX38) wherein $R^1$ and $R^2$ are each H.

EXAMPLE 1.b(iv)

Preparation of 3,4-diaza-3,4-bis(carboxymethyl)-1,2-dihydro-phenanthrene anhydride (FX39)

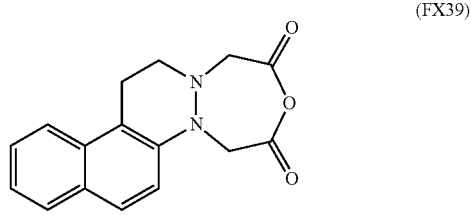 [SMILES: O=C1CN2CCc3c(ccc4ccccc34)N2CC(=O)O1]

(FX39)

A mixture of the diacid (FX38) wherein $R^1$ and $R^2$ are each H in Example 1.b(iii) (3.00 g, 0.01 mol) and dicyclohexyl-carbodiimide (DCC) (2.38 g, 0.011 mol) in anhydrous acetone (25 mL) is stirred under ambient temperature until complete consumption of the starting material. The reaction mixture is filtered to remove clicyclohexyl urea (DCU) and the filtrate evaporated in vacuo. The material is used as such for conjugation purposes.

EXAMPLE 1.b(v)

General synthesis of 1,2-diazaheterocycle-bombesin (7-14) conjugate (FX35)—Automated Procedure

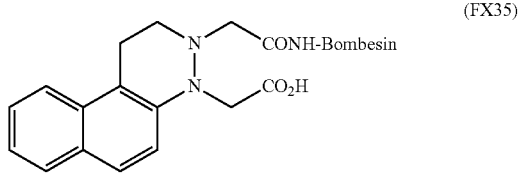

(FX35)

A typical procedure for the preparation of bombesin-1,2-diazaheterocycle conjugate (FX35) using an automated peptide synthesizer is described. It should be noted that other 1,2-diazaheterocycle conjugates may be conjugated to bombesin or any other peptide (Bm) by the same procedure. The bombesin peptide is prepared by fluorenylmethoxycarbonyl (Fmoc) solid phase peptide synthesis strategy with a commercial peptide synthesizer from Applied Biosystems (Model 432A SYNERGY Peptide Synthesizer). The first peptide cartridge contains Wang resin pre-loaded with an amide resin on 25-µmole scale. The amino acid cartridges are placed on the peptide synthesizer and the product is synthesized from the C- to the N-terminal position. Coupling of the Fmoc-protected amino acids (75 µmol) to the resin-bound free terminal amine (25 µmol) is carried out with 2-(1H-benzotriazol-1-yl)-1,1,3,3-tetramethyluronium hexafluorophosphate (HBTU, 75 μmol)/N-hydroxybenzotriazole (HOBt, 75 μmol). Each Fmoc protecting group on solid support is removed with 20% piperidine in dimethylformamide before the subsequent amino acid is coupled to it. The last cartridge contains the 1,2-diazaheterocycle carboxylic acid derivative of formula 1, which is coupled to the peptide automatically, thus avoiding the need for post-synthetic manipulations.

After the synthesis is completed, the product is cleaved from the solid support with a cleavage mixture containing trifluoroacetic acid (85%):water (5%):phenol (5%):thioanisole (5%) for 6 hours. The peptide-1,2-diazaheterocycle conjugate is precipitated with t-butyl methyl ether and lyophilized in water:acetonitrile (2:3) mixture. The conjugate is purified by HPLC and analyzed with LC/MS.

EXAMPLE 1.b(vi)

General synthesis of 1,2-diazaheterocycle-bombesin (7-14) conjugate (5)—Solution Phase Mixed Anhydride Procedure

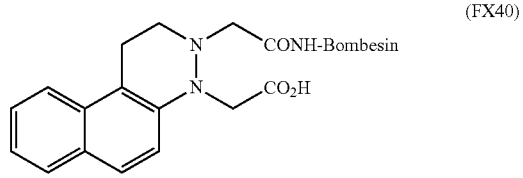

(FX40)

A typical procedure for the preparation of bombesin-1,2-diazaheterocycle conjugate (FX35) using mixed anhydride coupling procedure is described. It should be noted that other 1,2-diazaheterocycle 14-20 may be conjugated to bombesin or any other peptide targeting group by the same procedure. A solution of the 1,2-diazaheterocycle (FX38) wherein R is H (120 μmol) and triethylamine (250 μmol) in anhydrous dimethylformamide (DMF) (500 μL) is stirred and cooled to 0-10° C. Thereafter isobutylchloroformate (120 μmmol) is added and the mixture is stirred at 0-10° C. for about 30 minutes. Bombesin (7-14) peptide (100 μmol) in DMF is added to the above mixture and allowed to come to ambient temperature (about 20° C. to about 22° C.) and stirred at ambient temperature for about one hour. The conjugate is purified by HPLC and analyzed with LC/MS. The acyclic 1,2-diazaheterocycle -bombesin (7-14) conjugate has one of the following structures of formula 1 [Formula 1]-R2-Gln-Trp-Ala-Val-Gly-His-Leu-Met-NH$_2$ or [Formula 1]-R3-Gln-Trp-Ala-Val-Gly-His-Leu-Met-NH$_2$.

EXAMPLE 1.b(vii)

General synthesis of 1,2-diazaheterocycle -bombesin (7-14) conjugate (FX40)—Solution Phase Direct Acylation Procedure

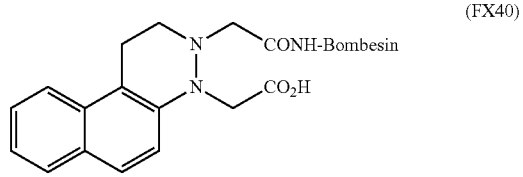

(FX40)

A typical procedure for the preparation of bombesin-1,2-diazaheterocycle conjugate (FX35) direct acylation procedure is described. It should be noted that other 1,2-diazaheterocycle 14-20 may be conjugated to bombesin or any other peptide targeting group by the same procedure. A solution of the 1,2-diazaheterocycle ((FX39) (120 μmol) and triethylamine (250 μmol) in anhydrous dimethylformamide (DMF) (500 μL) is stirred at ambient temperature (about 20° C. to about 22° C.) for about 16 hours. The conjugate is purified by HPLC and analyzed with LC/MS. The acyclic 1,2-diazaheterocycle -bombesin (7-14) conjugate has one of the following structures of formula 1 [Formula 1)-R2-Gln-Trp-Ala-Val-Gly-His-Leu-Met-NH$_2$ or [Formula 1]-R3-Gln-Trp-Ala-Val-Gly-His-Leu-Met-NH$_2$.

EXAMPLE 1.b(viii)

Optical Agent For Phototherapy Having Formula (FX41)

The invention provides an optical agent for phototherapy having formula (FX41).

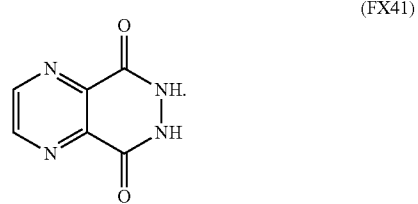 [SMILES: O=c1[nH][nH]c(=O)c2nccnc12]

(FX41)

EXAMPLE 1.b(ix)

General Procedure for Measuring Cell Viability upon Exposure of Tumor Cells to Photosensitizer and Light A general procedure is carried out for measuring cell viability upon exposure of tumor cells to photosensitizer and light. In this procedure, 0397 Leukemia cells (0.5×10$^6$) are plated in standard T-25 cell culture flasks, and are exposed to four controls and a series of test conditions corresponding to a range of photosensitizer concentrations.

TABLE 2

| Control and Test Conditions for Cell Viability Measurements | |
|---|---|
| Control 1 | no light, no photosensitizer |
| Control 2 | light, no photosensitizer |
| Control 3 | no light, photosensitizer |
| Control 4 | light, dimethylsulfoxide (DMSO) |
| Test Condition | light, photosensitizer |

The photosensitizers are dissolved in 20-30% DMSO at an initial concentration of 2-4 mM and are serially diluted to the final desired value. The cells are incubated at 37° C. with the photosensitizer for about 30 minutes prior to the exposure of light. The light source is a B-100SP High Intensity Lamp from UVP. The cells were exposed to light at desired time intervals, typically 5, 10, 20, and 30 minutes. Once exposure is complete, cells are processed to determine percent viability using Hank's Balanced Salt Solution (HBSS), Trypan blue stain, and a hemacytometer to count live and dead cells. The number of viable cells is determined and percent viability is determined $$\text{Percent Viability} = \frac{\text{No. of Viable Cells Counted} \times 100}{\text{Total No. of Cells Counted}}$$

The cells are incubated with the photosensitizer at the concentration range of 0 to 6 µM, are exposed to light for 0, 5, 10, and 20 minutes.

EXAMPLE 2

Photherapeutic Methods

The invention includes phototherapy methods wherein a phototherapeutic agent comprising a compound of any one of the formulae (FX1)-(FX41) is administered to a patient, for example, wherein a therapeutically effective amount of such a component is administered to a patient in need of treatment. Upon administration, the phototherapeutic agent is allowed to accumulate in a target region of interest (e.g., target tissue, tumor, or organ). To induce selective tissue damage, the phototherapeutic agent is activated by exposure to electromagnetic radiation. In an embodiment, the phototherapeutic agent is activated after an effective concentration of the phototherapeutic agent has accumulated in a target tissue. An effective concentration of a compound of the invention depends on the nature of the formulation, method of delivery, target tissue, activation method and toxicity to the surrounding normal non-target tissue. Exposure to electromagnetic radiation and activation of the phototherapeutic agent may occur during or after administration of the phototherapeutic agent and accumulation at the target tissue.

For photoactivation, the target region is illuminated with electromagnetic radiation having wavelengths in the range of about 350 nm to about 1300 nm, preferably for some applications in the range of about 350 nm to about 900 nm. In some embodiments, the wavelengths of the electromagnetic radiation correspond to a peak in the absorption spectrum of the phototherapeutic agent, for example is within 20 nanometers of a peak in the absorption spectrum of the phototherapeutic agent. In some phototherapeutic procedures the target site is exposed to electromagnetic radiation having sufficient fluence and/or power sufficient to activate the phototherapeutic agent so as to induce cell death, for example via necrosis or apoptosis processes. In some embodiments, electromagnetic radiation of low energy, power and/or fluence is needed to activate the phototherapeutic agent. If the region of interest is, for example a lesion on the skin surface, the region can be directly illuminated. Otherwise, endoscopic catheters equipped with a electromagnetic radiation source may be employed to provide a photodiagnostic and/or the phototherapeutic effect.

Appropriate power and intensity of the electromagnetic radiation depends on the size, depth, and the pathology of the lesion, as is known to one skilled in the art. In an embodiment, the fluence of the electromagnetic radiation is preferably, but not always, kept below 200 mW/cm² to minimize undesirable thermal effects. The intensity, power, and duration of the illumination, and the wavelength of the electromagnetic radiation may vary widely depending on the body location, the lesions site, the effect to be achieved, etc. Appropriate power depends on the size, depth, and the pathology of the lesion, as is known to one skilled in the art. In an embodiment, the power is preferably selected over the range of 1-500 mW/cm², and optionally selected over the range of 1-200 mW/cm². In an embodiment, the duration of the exposure to electromagnetic radiation selected over the range of 1 second to 60 minutes.

The inventive compounds can be formulated into pharmaceutical, therapeutic and/or diagnostic compositions for enteral (oral or rectal), parenteral, topical, or cutaneous administration. Topical or cutaneous delivery of the photosensitizer may also include aerosol formulation, creams, gels, solutions, etc. The compounds are administered in doses effective to achieve the desired diagnostic or therapeutic effect. Such doses may vary widely depending upon the particular complex employed, the organs or tissues to be examined, the equipment employed in the clinical procedure, the efficacy of the treatment achieved, and the like. In an embodiment, a phototherapeutic agent of the invention comprises an effective amount of a compound of any of formula (FX1)-(FX41) and one or more pharmaceutical carriers and excipients appropriate for the type of administration contemplated. These compositions may also include stabilizing agents and tissue penetration enhancing agents.

In an embodiment, the invention provides a method of using a phototherapeutic agent, the method comprising: (i) administering a therapeutically effective amount of a phototherapeutic agent to a subject, the phototherapeutic agent comprising a compound being of the formula (FX1):

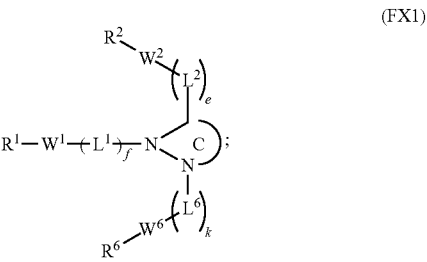

wherein ring C is:

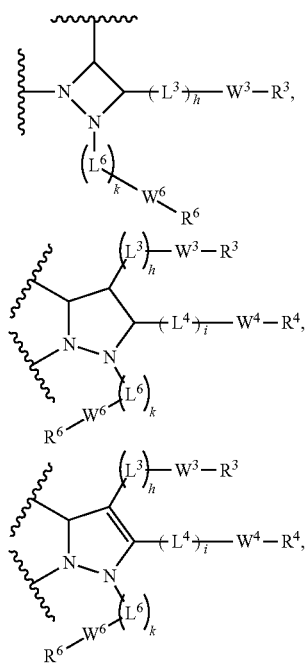

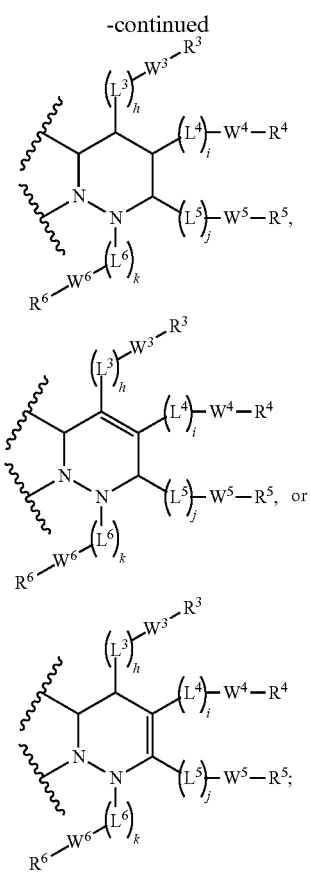

or a pharmaceutically acceptable salt or ester thereof;

each of $L^1$-$L^6$, if present, is independently $C_1$-$C_{10}$ alkylene, $C_3$-$C_{10}$ cycloalkylene, $C_2$-$C_{10}$ alkenylene, $C_3$-$C_{10}$ cycloalkenylene, $C_2$-$C_{10}$ alkynylene, ethenylene, ethynylene, phenylene, 1-aza-2,5-dioxocyclopentylene, —(CH$_2$CH$_2$O)$_m$—, —(CHOH)$_m$—, or 1,4-diazacyclohexylene;

each of $W^1$ and $W^6$ is independently a single bond, —(CH$_2$)$_n$—, —(HCCH)$_n$—, —O—, —S—, —SO—, —SO$_2$—, —SO$_3$—, —OSO$_2$—, —NR$^7$—, —CO—, —COO—, —OCOO—, —CONR$^8$—, —CONR$^8$—, —NR$^9$CO—, —OCONR$^{10}$—, —NR$^{11}$COO—, —NR$^{12}$CONR$^{13}$—, or —NR$^{14}$CSNR$^{15}$—;

each of $W^2$-$W^5$ is independently a single bond, a double bond, —(CH$_2$)$_n$—, —(HCCH)$_n$—, —(HCCH)$_n$—, —O—, —S—, —SO—, —SO$_2$—, —SO$_3$—, —OSO$_2$—, —NR$^7$—, —CO—, —COO—, —OCO—, —OCOO—, —CONR$^8$—, —NR$^9$CO—, —OCONR$^{10}$—, —NR$^{11}$COO—, —NR$^{12}$CONR$^{13}$—, or —NR$^{14}$CSNR$^{15}$—;

each of $R^1$ and $R^6$ is independently hydrogen, $C_1$-$C_{20}$ alkyl, $C_3$-$C_{20}$ cycloalkyl, $C_5$-$C_{30}$ aryl, $C_5$-$C_{30}$ heteroaryl, $C_1$-$C_{20}$ acyl, $C_2$-$C_{20}$ alkenyl, $C_2$-$C_{20}$ alkynyl, $C_5$-$C_{20}$ alkylaryl, $C_1$-$C_6$ alkoxycarbonyl, halo, halomethyl, dihalomethyl, trihalomethyl, —CN, —CO$_2$R$^{16}$, —CONR$^{17}$R$^{16}$, —COR$^{19}$, —NO$_2$, —SOR$^{26}$, —OSR$^{21}$, —SO$_2$R$^{22}$, —SO$_2$OR$^{23}$, —SO$_2$NR$^{24}$R$^{25}$, —PO$_3$R$^{26}$R$^{27}$, —OR$^{26}$, —SR$^{29}$, —NR$^{30}$R$^{31}$, —NR$^{32}$COR$^{33}$, —(CHOH)$_m$R$^{34}$, —(CH$_2$CH$_2$O)$_m$R$^{35}$, —CH(R$^{36}$)CO$_2$H, —CH(R$^{37}$)NH$_2$, a dye, or Bm;

each of $R^2$-$R^5$ is independently hydrogen, $C_1$-$C_{20}$ alkyl, $C_3$-$C_{20}$ cycloalkyl, $C_5$-$C_{30}$ aryl, $C_5$-$C_{30}$ heteroaryl, $C_1$-$C_{20}$ acyl, $C_2$-$C_{20}$ alkenyl, $C_2$-$C_{20}$ alkynyl, $C_5$-$C_{20}$ alkylaryl, $C_1$-$C_6$ alkoxycarbonyl, halo, halomethyl, dihalomethyl, trihalomethyl, =O, =S, —CN, —CO$_2$R$^{16}$, —CONR$^{17}$R$^{18}$, —COR$^{19}$, —NO$_2$, —SOR$^{20}$, —OSR$^{21}$, —SO$_2$R$^{22}$, —SO$_2$OR$^{23}$, —SO$_2$NR$^{24}$R$^{25}$, —PO$_3$R$^{26}$R$^{27}$, —OR$^{28}$, —SR$^{29}$, —NR$^{30}$R$^{31}$, —NR$^{32}$COR$^{33}$, —(CHOH)$_m$R$^{34}$, —(CH$_2$CH$_2$O)$_m$R$^{35}$, —CH(R$^{36}$)CO$_2$H, —CH(R$^{37}$)NH$_2$, a dye, or Bm;

or wherein at least two of $R^1$-$R^6$ combine to form one or more alicyclic or aromatic, carbocyclic or heterocyclic 5 or 6 membered rings;

wherein at least one of $R^1$-$R^6$ is $C_5$-$C_{30}$ aryl or $C_5$-$C_{30}$ heteroaryl, or wherein at least two of $R^1$-$R^6$ combine to form $C_5$-$C_{30}$ aryl or $C_5$-$C_{30}$ heteroaryl;

each m is independently an integer selected from the range of 1 to 100;

each n is independently an integer selected from the range of 1 to 10;

each of f, e, h, i, j and k is independently 0 or 1;

each of $R^7$-$R^{33}$ is independently hydrogen, $a_1$-$C_{20}$ alkyl, $C_5$-$C_{30}$ aryl or $C_5$-$C_{30}$ heteroaryl;

each of $R^{34}$ and $R^{35}$ is independently hydrogen or $C_1$-$C_{10}$ alkyl;

each of $R^{36}$ and $R^{37}$ is independently a side chain residue of a natural a-amino acid; and each Bm is independently an amino acid, a peptide, a protein, a nucleoside, a nucleotide, an enzyme, a carbohydrate, a glycomimetic, an oligomer, a lipid, a polymer, an antibody, an antibody fragment, a mono- or polysaccharide comprising 1 to 50 carbohydrate units, a glycopeptide, a glycoprotein, a peptidomimetic, a drug, a steroid, a hormone, an aptamer, a receptor, a metal chelating agent, a polynucleotide comprising 2 to 50 nucleic acid units, a peptoid comprising 2 to 50 N-alkylaminoacetyl residues, a glycopeptide comprising 2 to 50 amino acid and carbohydrate units, or a polypeptide comprising 2 to 30 amino acid units; and (ii) exposing the phototherapeutic agent administered to the patient to electromagnetic radiation. In an embodiment, the phototherapeutic agent is exposed to a therapeutically effective amount of electromagnetic radiation. As used herein, a therapeutically effective amount of electromagnetic radiation is an amount for achieving a desired therapeutic result, for example an amount for generating a therapeutically effective amount of reactive species for damaging or causing cell death of a selected target tissue. In an embodiment, the method further comprises generating one or more reactive species from said compound administered to the patient via the exposure of the phototherapeutic agent to applied electromagnetic radiation. In an embodiment, for example, the method further comprises the step of cleaving a photolabile N—N bond of the central alicyclic diaza group of the compound so as to generate reactive species comprising free radicals. In an embodiment, the method further comprises targeting the phototherapeutic agent to a selected organ in the patient or to a selected tissue type in the patient. In an embodiment, a therapeutically effective dose of the phototherapeutic agent is administered to a patient in need of treatment.

Embodiments of this aspect may comprise a method of carrying out an in vivo therapeutic and/or diagnostic procedure. In an embodiment, the invention comprises a method of carrying out an in vivo phototherapeutic, photoactivation, and/or photosensitizing procedure. The present methods have broad clinical utility which includes, but is not limited to, phototherapy of tumors, inflammatory processes, and impaired vasculature. In embodiments, subjects of the invention may be any mammal, such as a human, and optionally the subject of the present methods is a patient in need of treatment and/or diagnosis. The present methods are also useful in ex vivo and in vitro procedures, including medical therapeutic and diagnostic procedures.

Phototherapeutic agents useful in the present methods include alicyclic diaza compounds containing at least one N—N bond directly or indirectly coupled to a $C_5$-$C_{30}$ aryl or $C_5$-$C_{30}$ heteroaryl comprising one or more aromatic and/or heterocyclic aromatic groups. Phototherapeutic agents useful in the present methods include compounds optionally having a ligand for targeted administration. Phototherapeutic agents useful in the present methods include compounds optionally having a dye component, such as a fluorophore or chromophore, for imaging and/or visualization functionality. In an embodiment, the method of the invention comprises administering to a patient a compound having any one of formula selected from (FX1)-(FX41), including any of the specific compositions classes and compounds described in connection with formula (FX1)-(FX41). As will be understood by one of skill in the art, the present methods expressly include methods of using phototherapeutic agents wherein the phototherapeutic agent includes the compound classes, compounds, and all variations thereof, described herein, including the compound classes, compounds and variations described in connection with any one of formulae (FX1)-(FX41).

Methods of the invention may optionally further comprise a number of other steps. In an embodiment, the present methods further comprise the step of administering the phototherapeutic agent into a bodily fluid of the subject. The phototherapeutic agent may be introduced into the patient by any suitable method, including intravenous, intraperitoneal or subcutaneous injection or infusion, oral administration, transdermal absorption through the skin, or by inhalation. In an embodiment, the method further comprises contacting a target tissue, such as a organ, tissue, tumor, lesion, or cell type with a compound of any one of formulae (FX1)-(FX41) prior to or during the exposure step. In an embodiment, the method further comprises allowing the compound to accumulate in a target tissue prior to exposure of the phototherapeutic agent to electromagnetic radiation. In an embodiment, the method further comprises targeting the diagnostic agent to a selected organ, tissue, tumor, inflammation, lesion, or cell type. In an embodiment, the phototherapeutic agent is administered to the skin, a tumor, surgical site, or a wound site. In an embodiment, for example, the phototherapeutic agent is administered and/or delivered to a blood vessel, lung, heart, throat, ear, rectum, bladder, stomach, intestines, esophagus, liver, brain, prostrate, breast or pancreas of the subject.

In an embodiment, a therapeutically effective amount of the phototherapeutic agent is provided to the subject. For example, parenteral administration advantageously contains a sterile aqueous solution or suspension of the phototherapeutic agent having a concentration of a compound of any one of formulae (FX1)-(FX41) ranging from about 1 nM to about 0.5M. Preferred parenteral formulations have a concentration of the compound of any one of formulae (FX1)-(FX41) selected over the range of 1 μM to 10 mM. Such solutions also may contain pharmaceutically acceptable buffers, emulsifiers, surfactants, and, optionally, electrolytes such as sodium chloride. In an embodiment, the dose of the compound of any one of formulae (FX1)-(FX41) may vary from 0.1 to 500 mg/kg body weight, preferably from 0.5 to 2 mg/kg body weight.

In methods of the present invention, the phototherapeutic agent can be formulated for enteral (oral or rectal), parenteral, topical, or cutaneous administration. Topical or cutaneous delivery of the phototherapeutic agent may also include aerosols, creams, gels, solutions, emulsions and colloids. The compositions are administered in doses effective to achieve the desired diagnostic or therapeutic objective. Such doses may vary widely depending upon the particular complex employed, the organs or tissues to be examined or treated, the equipment employed in the clinical procedure, the efficacy of the treatment achieved, and the like. These compositions contain an effective amount of the phototherapeutic agent along with conventional pharmaceutical carriers and excipients appropriate for the type of administration contemplated. These compositions may also include stabilizing agents and skin penetration enhancing agents and also may contain pharmaceutically acceptable buffers, emulsifiers, surfactants, and, optionally, electrolytes such as sodium chloride. Formulations for enteral administration may vary widely, as is well known in the art. In general, such formulations are liquids, which include an effective amount of the complexes in aqueous solution or suspension. Such enteral compositions may optionally include buffers, surfactants, emulsifiers, thixotropic agents, and the like. Compounds for oral administration may also contain flavoring agents and other ingredients for enhancing their organoleptic qualities. Formulations for topical delivery may also contain liquid or semisolid excipients to assist in the penetration of the photosensitizer. The compounds may also be delivered in an aerosol spray. As will be understood by one having skill in the art, the optical conditions for the step of exposing the phototherapeutic agent administered to the patient to electromagnetic radiation will vary considerably with the (i) therapeutic and/or diagnostic objectives, and (ii) the condition of the subject (e.g., height, weight, state of health etc.). In an embodiment, the applied electromagnetic radiation has wavelengths, energy and/or fluence sufficient to achieve a desired therapeutic and/or diagnostic result. In an embodiment, the electromagnetic radiation has wavelengths, energy and/or fluence sufficient to activate the phototherapeutic agent, for example wavelengths, energy and/or fluence sufficient to result in generation of reactive species by cleavage of a N—N bond of the central diaza ring. In a method, the electromagnetic radiation exposed to the phototherapeutic agent has wavelengths selected over the range of 350 nm-1300 nm, preferably for some applications 350 nm-900nm, preferably for some applications 600 nm to 900 nm. In an embodiment, the electromagnetic radiation exposed to the phototherapeutic agent has wavelengths corresponding to a maximum in the absorption spectrum of the phototherapeutic agent, preferably for some applications a maximum in the visible or NIR regions of the electromagnetic spectrum. Optionally, excitation is achieved using electromagnetic substantially free (e.g., less than about 10% of total radiant energy), of ultraviolet radiation, for example, to minimize exposure of the subject to electromagnetic radiation capable of causing unwanted cell or tissue damage. Electromagnetic radiation may be provided to the phototherapeutic agent using a range of optical sources and/or surgical instrumentation, including a laser, light emitting diodes, fiber optic device, endoscope, catheter, optical filters, or any combination of these. Example 3: Targeted Optical Agents 3.a. Targeting Methods The invention includes methods for phototherapy using an optical agent providing targeted delivery to a selected target tissue. Embodiments of this aspect use an optical agent, such as a photosensitizer, having a targeting ligand. As will be understood by one of skill in the art, selection of the composition of a targeting ligand in the present methods will dependent on therapeutic and/or diagnostic objectives, the condition of the subject and the chemical composition and properties of the target tissue of interest.

In one example, a targeted compound can contain all or part of a steroid hormone or a steroid receptor binding compound, and therefore target steroid hormone sensitive receptors. In this example, the targeted compound is administered, targets and preferably accumulates in the desired site such as breast and/or prostate lesion and is photoactivated for monitoring, imaging, or therapy remotely or at the target site. Similar target binding molecules and uses will be recognized by one skilled in the art. For example, the targeted compound can be a compound that targets and binds to a somatostatin, bombesin, CCK, and/or neurotensin receptor binding molecule, or can be a carcinogenic embryonic antigen-binding compound that binds to a carcinogenic embryonic antigen. These are then photoactivated at, for example, lung cancer cells with CCK receptor binding molecules, colorectal cancer cells with ST receptor and carcinoembryonic antigen (CEA) binding molecules, melanoma cells with dihydroxyindolecarboxylic acid, vascular sites of atherosclerotic plaque with integrin receptor binding molecules, brain lesions with amyloid plaque binding molecules, and the like.

Successful specific targeting of photoactive compounds to tumors using antibodies and peptides for diagnostic imaging of tumors has been described in Achilefu et al., Novel receptor-targeted fluorescent contrast agents for in vivo imaging of tumors, *Investigative Radiology,* 2000, 35, pp. 479-485; Ballou et al., Tumor labeling in vivo using cyanine conjugated monoclonal antibodies, *Cancer Immunology and Immunotherapy,* 1995, 41, pp. 257-263; and Licha et al., New contrast agent for optical imaging: acid cleavable conjugates of cyanine dyes with biomolecules, in *Biomedical Imaging: Reporters, Dyes and Instrumentation, Proceedings of SPIE,* 1999, 3600, pp. 29-35. As such, it is widely accepted that targeted photochemicals are effective in targeting, detecting and treating a wide range of physiological and biological sites.

The optical agents of this example can contain additional functionalities that can be used to attach various types of biomolecules, synthetic polymers, and organized aggregates for selective delivery to various organs or tissues of interest. Examples of synthetic polymers include polyaminoacids, polyols, polyamines, polyacids, oligonucleotides, aborols, dendrimers, and aptamers. The invention includes, but is not limited to, phototherapeutic agents comprising an optical agent—biomolecule conjugate which provides advantages over nonspecific optical agents or the conjugation of optical agents to very large biomolecules. These conjugates provide enhanced localization in, and rapid visualization of, tumors which is beneficial for imaging, monitoring, diagnosis and therapy. The agents are rapidly cleared from blood and non-target tissues so there is less concern for accumulation and for toxicity. A variety of high purity compounds can be easily synthesized for combinatorial screening of new targets, e.g., to identify receptors or targeting agents, and for the ability to affect the pharmacokinetics of the conjugates by minor structural changes.

In some embodiments, a liposome or micelle can be utilized as a carrier or vehicle for the composition. For example, in some embodiments, an optical agent comprises a compound of the invention that can be a part of the lipophilic bilayers or micelle, and the targeting ligand, if present, can be on the external surface of the liposome or micelle. As another example, a targeting ligand can be externally attached to the liposome or micelle after formulation for targeting the liposome or micelle (which contains a phototherapeutic agent/ photosensitizer compound of the invention) to the desired tissue, organ, or other site in the body.

In embodiments, compounds of the invention are useful for both oncology and non-oncology applications. Some specific targets are tumors accessible via endoscope. In an application, a compound that targets a protein, polypeptide, oligonucleotide or other biomolecule associated with such a tumor is administered to the tumor via endoscope or other useful method. Then, the compounds of the invention can be used in phototherapeutic applications, monitoring applications, diagnosis applications or imaging applications. Other specific target tissues include colon, lung, ovarian, cervical, esophageal, bladder, blood, stomach cancers, endometriosis, and bacterial infections.

3b: Targeting Ligands

The estrogen receptor is an example of a steroid receptor to which steroid receptor binding molecules would bind. The following compounds are known to bind to the estrogen receptor: estratriol; 17β-aminoestrogen (AE) derivatives such as prolame and butolame; drugs such as tamoxifen, ICI-164384, raloxifene, and genistein; 17β-estradiol; glucocorticoids; progesterone; estrogens; retinoids; fatty acid derivatives; and phytoestrogens. In addition, commercially available kits can identify compounds specific for binding to the estrogen receptor (e.g., Estrogen Receptor-alpha Competitor Assay Kit, Red; and Estrogen Receptor-beta Competitor Assay Kit, Red (Invitrogen Corp., Carlsbad Calif.).

The glucose receptor is an example of a carbohydrate receptor to which carbohydrate receptor binding molecules would bind. The glucose conjugate N-palmitoyl glucosamine [NPG] is known to bind the glucose receptor (Dufes et al., Pharm. Res. 17:1250, 2000). The glycoprotein hormone receptor is another example of a carbohydrate receptor to which carbohydrate receptor binding molecules would bind. Follicle stimulating hormone (FSH) is known to bind the glycoprotein hormone receptor (Tilly et al., Endocrinology 131: 799, 1992). Other compounds known to bind the carbohydrate receptor, and hence examples of carbohydrate receptor binding molecules, are: polysialic acid, bacterial adhesins (specialized surface proteins that mediate binding of many pathogenic bacteria, such as enterohemorrhagic *E. coli* (EHEC) and *Shigella dysenteriae,* to host cells, which allow these bacteria to colonize host cell surfaces), soluble carbohydrate receptor analogs, artificial glycopolymers and other multivalent glycoconjugates such as an acrylamide copolymer carrying -L-fucopyranoside and 3-sulfo-D-galactopyranoside in clusters, isomeric carbohydrates, synthetic derivatives, neoglycoproteins, neoglycolipids, glycosidases, and glycosyltransferases. Carbohydrate binding proteins can be screened with phage display libraries as known to a person of ordinary skill in the art.

Somatostatin receptor binding molecules include somatostatin and somatostatin receptor analogs, octreotide, glycosylated somatostatin-14 (somatostatin-dextran"), seglitide, and peptides P587 and P829 as described in Vallabhajosula et al., J. Nuclear Med., 37:1016, 1996.

Cholecystokinin receptor binding molecules include the endogenous peptides cholecystekinin (CCK)-4, CCK-8, CCK-33, and gastrin; antagonists devazepide and lorglumide; agonists BC264 [Tyr($SO_3$H)-gNle-mGly-Trp-(NMe)Nle-Asp-Phe-$NH_3$] and desulfated CCK-8; Kinevac (synthetic cholecystekinin, sincalide); and CCK analogues modified at the sulfated tyrosyl at position 27.

Neurotensin receptor binding molecules include neurotensin, neuromedin N, JMV449 (H-Lysψ($CH_2$NH)-Lys-Pro-Tyr-Ile-Leu), the non-peptide antagonist SR142948A (2-([5-2,6-dimethoxyphenyl)-1-(4-(N-[3-dimethylaminopropyl]-

N-methylcarbamoyl)-2-isopropylphenyl)-1H-pyrazole-3-carbonyl)amino)adamantane-2-carboxylic acid hydrochloride), and levocobastine. Commercially available neurotensin receptor binding kits can evaluate potential neurotensin receptor binding molecules (e.g., DELFIA Neurotensin Receptor Binding Kit, PerkinElmer (Boston Mass.)).

Bombesin receptor binding molecules include the endogenous ligands gastrin-releasing peptide (GRP), neuromedin B (NMB), and GRP-18-27, and antagonists including JMV-1458 (glycine-extended bombesin (paraphydroxy-phenyl-propionyl-Gln-Trp-Ala-Val-Gly-His-Leu-Met-Gly-OH)), JMV-641, JMV-1799, and JMV-1802, PD165929, 1-naphthoyl-[DAla$^{24}$,DPro$^{26}$,ψ26-27]GRP-20-27, kuwanon H, and kuwanon G. Commercially available bombesin receptor binding kits can evaluate potential bombesin receptor binding molecules (e.g., DELFIA Bombesin Receptor Binding Kit, PerkinElmer (Boston Mass.)).

ST receptor binding molecules include native ST peptide, and SEQ ID NO:2, SEQ ID NO:3, SEQ ID NOS:5-54 and fragments and derivatives thereof from U.S. Pat. No. 5,518,888.

Compounds of the invention can contain all or part of a targeting ligand, receptor or peptide known to bind to a specific target, such as a target tissue.

Targeting ligands may be linked to the backbone or other portion of the present compounds using a range of synthetic approaches known in the art, including the synthetic approaches for conjugating biomolecule targeting ligands to optical agents as disclosed in Hnatowich et al., Radiolabeling of Antibodies: A simple and efficient method, *Science*, 1983, 220, p. 613; Pelegrin et al., Photoimmunodiagnostics with antibody-fluorescein conjugates: in vitro and in vivo preclinical studies, *Journal of Cellular Pharmacology*, 1992, 3, pp. 141-145; Achilefu et al., Novel receptor-targeted fluorescent contrast agents for in vivo imaging of tumors, *Investigative Radiology*, 2000, 35, pp. 479-485; Ballou et al., Tumor labeling in vivo using cyanine conjugated monoclonol antibodies, *Cancer Immunology and Immunotherapy*, 1995, 41, pp. 257-263; and Licha et al., New contrast agent for optical imaging: acid cleavable conjugates of cyanine dyes with biomolecules, in *Biomedical Imaging: Reporters, Dyes and Instrumentation, Proceedings of SPIE*, 1999, 3600, pp. 29-35; and U.S. Pat. No. 5,714,342.

Linking of biomolecule targeting ligands having an amine group, for example, may be achieved by techniques involving succinimido active esters. For example, a carboxyl group of a compound of the invention is activated by making a mixed anhydride in situ with isobutylchloroformate. The activated compound is subsequently reacted with any biomolecule bearing an amino group, such as a polypeptide, protein, enzyme, antibody or fragment thereof, to achieve linking of the biomolecule to the compound so as to provide a targeting ligand covalently bond to the compound. Alternatively, a carboxyl group of the present compounds may be first esterified with N-hydroxysuccinimide, and subsequently reacted with the amino group of a biomolecule, such as a polypeptide, protein, enzyme, antibody or fragment thereof, to form an amide bond linking the biomolecule to the compound so as to provide a targeting ligand covalently bond to the compound.

EXAMPLE 4

Administration and Formulation

4a: Salts and Prodrugs

The invention contemplates pharmaceutically active compounds either chemically synthesized or formed by in vivo biotransformation to compounds set forth herein.

Compounds of this invention and compounds useful in the methods of this invention include those of the compounds and formula(s) described herein and pharmaceutically-acceptable salts and esters of those compounds. In embodiments, salts include any salts derived from the acids and bases of the formulas herein which are acceptable for use in human or veterinary applications. In embodiments, the term ester refers to hydrolyzable esters of compounds of the names and formulas herein. In embodiments, salts and esters of the compounds of the formulas herein can include those which have the same or better therapeutic, diagnostic, or pharmaceutical (human or veterinary) general properties as the compounds of the formulas herein. In an embodiment, a composition of the invention is a compound or salt or ester thereof suitable for pharmaceutical formulations.

Compounds of the invention can have prodrug forms. Prodrugs of the compounds of the invention are useful in embodiments including compositions and methods. Any compound that will be converted in vivo to provide a biologically, pharmaceutically, diagnostically, or therapeutically active form of a compound of the invention is a prodrug. Various examples and forms of prodrugs are well known in the art. Examples of prodrugs are found, inter alia, in: Design of Prodrugs, edited by H. Bundgaard, (Elsevier, 1985); Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191 (1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392). A prodrug, such as a pharmaceutically acceptable prodrug, can represent prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of a compound described herein, for example, by hydrolysis in blood or by other cell, tissue, organ, or system processes. Further discussion is provided in: T. Higuchi and V. Stella, Pro-drugs as Novel Delivery Systems, V. 14 of the A.C.S. Symposium Series; and in Edward B. Roche, ed., Bioreversible Carriers in Drug Design, American Pharmaceutical Association and Pergamon Press (1987).

Optical agents of the invention can be formulated with pharmaceutically-acceptable anions and/or cations. Pharmaceutically-acceptable cations include among others, alkali metal cations (e.g., Li$^+$, Na$^+$, K$^+$), alkaline earth metal cations (e.g., Ca$^{2+}$, Mg$^{2+}$), non-toxic heavy metal cations and ammonium (NH$_4^+$) and substituted ammonium (N(R')$_4$', where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include, among others, halides (e.g., F$^-$, Cl$^-$, Br$^-$, At$^-$), sulfate, acetates (e.g., acetate, trifluoroacetate), ascorbates, aspartates, benzoates, citrates, and lactate.

Pharmaceutically acceptable salts comprise pharmaceutically-acceptable anions and/or cations. As used herein, the term "pharmaceutically acceptable salt" can refer to acid addition salts or base addition salts of the compounds in the present disclosure. A pharmaceutically acceptable salt is any salt which retains at least a portion of the activity of the parent compound and does not impart significant deleterious or undesirable effect on a subject to whom it is administered and in the context in which it is administered. Pharmaceutically acceptable salts include metal complexes and salts of both inorganic and organic acids. Pharmaceutically acceptable salts include metal salts such as aluminum, calcium, iron, magnesium, manganese and complex salts. Pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, cilexetil, citric, edetic, edisylic, estolic, esyl, esylic, formic, fumaric, gluceptic, gluconic, glutamic, glycolic, glycolylarsanilic, hexamic, hexylresorcjnoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanlic, sulfonic, sulfuric, tannic, tartaric, teoclic, toluenesulfonic, and the like. Pharmaceutically acceptable salts can be derived from amino acids, including, but not limited to, cysteine. Other pharmaceutically acceptable salts can be found, for example, in Stahl et al., Handbook of Pharmaceutical Salts: Properties, Selection, and Use, Wiley-VCH, Verlag Helvetica Chimica Acta, Zürich, 2002. (ISBN 3-906390-26-6).

4b: Efficacy

Typically, a compound of the invention, or pharmaceutically acceptable salt thereof, is administered to a subject in a diagnostically or therapeutically effective amount. One skilled in the art generally can determine an appropriate dosage.

Compositions for oral administration can be, for example, prepared in a manner such that a single dose in one or more oral preparations contains at least about 20 mg of the diaza compound per square meter of subject body surface area, or at least about 50, 100, 150, 200, 300, 400, or 500 mg of the diaza compound per square meter of subject body surface area (the average body surface area for a human is, for example, 1.8 square meters). In particular, a single dose of a composition for oral administration can contain from about 20 to about 600 mg, and in certain aspects from about 20 to about 400 mg, in another aspect from about 20 to about 300 mg, and in yet another aspect from about 20 to about 200 mg of the diaza compound per square meter of subject body surface area. Compositions for parenteral administration can be prepared in a manner such that a single dose contains at least about 20 mg of the diaza compound per square meter of subject body surface area, or at least about 40, 50, 100, 150, 200, 300, 400, or 500 mg of the diaza compound per square meter of subject body surface area. In particular, a single dose in one or more parenteral preparations contains from about 20 to about 500 mg, and in certain aspects from about 20 to about 400 mg, and in another aspect from about 20 to about 450 mg, and in yet another aspect from about 20 to about 350 mg of the diaza compound per square meter of subject body surface area. It should be recognized that these oral and parenteral dosage ranges represent generally preferred dosage ranges, and are not intended to limit the invention. The dosage regimen actually employed can vary widely, and, therefore, can deviate from the generally preferred dosage regimen. It is contemplated that one skilled in the art will tailor these ranges to the individual subject.

Toxicity and therapeutic efficacy of such compounds and bioconjugates can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$. Compounds and bioconjugates that exhibit large therapeutic indices are preferred. While compounds and bioconjugates exhibiting toxic side effects can be used, care should be taken to design a delivery system that targets such compounds and bioconjugates to the site affected by the disease or disorder in order to minimize potential damage to unaffected cells and reduce side effects.

Data obtained from the cell culture assays and animal studies can be used in formulating a range of dosages for use in humans and other mammals. The dosage of such compounds and bioconjugates lies preferably within a range of circulating plasma or other bodily fluid concentrations that include the $ED_{50}$ and provides clinically efficacious results (i.e., reduction in disease symptoms). The dosage can vary within this range depending upon the dosage form employed and the route of administration utilized. For any compound and bioconjugate of the present invention, the therapeutically effective amount can be estimated initially from cell culture assays. A dosage can be formulated in animal models to achieve a circulating plasma concentration range that includes the $ED_{50}$ (the concentration of the test compound that achieves a half-maximal inhibition of symptoms) as determined in cell culture. Such information can be used to more accurately determine useful dosages in humans and other mammals. Compound and bioconjugate levels in plasma can be measured, for example, by high performance liquid chromatography.

An amount of a compound or bioconjugate that can be combined with a pharmaceutically acceptable carrier to produce a single dosage form will vary depending upon the patient treated and the particular mode of administration. It will be appreciated by those skilled in the art that the unit content of a compound/bioconjugate contained in an individual dose of each dosage form need not in itself constitute a therapeutically effective amount, as the necessary therapeutically effective amount could be reached by administration of a number of individual doses. The selection of dosage depends upon the dosage form utilized, the condition being treated, and the particular purpose to be achieved according to the determination of those skilled in the art.

The dosage and dosage regime for treating a disease or condition can be selected in accordance with a variety of factors, including the type, age, weight, sex, diet and/or medical condition of the patient, the route of administration, pharmacological considerations such as activity, efficacy, pharmacokinetic and/or toxicology profiles of the particular compound/bioconjugate employed, whether a compound/bioconjugate delivery system is utilized, and/or whether the compound/bioconjugate is administered as a pro-drug or part of a drug combination. Thus, the dosage regime actually employed can vary widely from subject to subject, or disease to disease and different routes of administration can be employed in different clinical settings.

The identified compounds/bioconjugates monitor, treat, inhibit, control and/or prevent, or at least partially arrest or partially prevent, diseases and conditions of interest and can be administered to a subject at therapeutically effective amounts and optionally diagnostically effective amounts. Compositions/formulations of the present invention comprise a therapeutically effective amount (which can optionally include a diagnostically effective amount) of at least one compound or bioconjugate of the present invention. Subjects receiving treatment that includes a compound/bioconjugate of the invention are preferably animals (e.g., mammals, reptiles and/or avians), more preferably humans, horses, cows, dogs, cats, sheep, pigs, and/or chickens, and most preferably humans.

4c: Administration

The preferred composition depends on the route of administration. Any route of administration can be used as long as the target of the compound or pharmaceutically acceptable salt is available via that route. Suitable routes of administration include, for example, oral, intravenous, parenteral, inhalation, rectal, nasal, topical (e.g., transdermal and intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual, and intestinal administration.

In an embodiment, the invention provides a method for treating a medical condition comprising administering to a subject (e.g. patient) in need thereof, a therapeutically effective amount of a composition of the invention, such as a compound of any one of formulas (FX1)-(FX41). In an embodiment, the invention provides a method for diagnosing or aiding in the diagnosis of a medical condition comprising administering to a subject in need thereof, a diagnostically effective amount of a composition of the invention. In an embodiment, the medical condition is cancer, or various other diseases, injuries, and disorders, including cardiovascular disorders such as atherosclerosis and vascular restenosis, inflammatory diseases, ophthalmic diseases and dermatological diseases.

The diagnostic and therapeutic formulations of this invention can be administered alone, but can be administered with a pharmaceutical carrier selected upon the basis of the chosen route of administration and standard pharmaceutical practice.

Any suitable form of administration can be employed in connection with the diagnostic and therapeutic formulations of the invention. The diagnostic and therapeutic formulations of this invention can be administered intravenously, in oral dosage forms, intraperitoneally, subcutaneously, or intramuscularly, all using dosage forms well known to those of ordinary skill in the pharmaceutical arts.

The present compositions, preparations and formulations can be formulated into diagnostic or therapeutic compositions for enteral, parenteral, topical, aerosol, inhalation, or cutaneous administration. Topical or cutaneous delivery of the compositions, preparations and formulations can also include aerosol formulation, creams, gels, solutions, etc. The present compositions, preparations and formulations are administered in doses effective to achieve the desired diagnostic and/or therapeutic effect. Such doses can vary widely depending upon the particular compositions employed in the composition, the organs or tissues to be examined, the equipment employed in the clinical procedure, the efficacy of the treatment achieved, and the like. These compositions, preparations and formulations contain an effective amount of the composition(s), along with conventional pharmaceutical carriers and excipients appropriate for the type of administration contemplated. These compositions, preparations and formulations can also optionally include stabilizing agents and skin penetration enhancing agents.

(i) Parenteral Administration

Compounds and bioconjugates of the present invention can be formulated for parenteral administration by injection (e.g., by bolus injection or continuous infusion). Formulations for injection can be presented in unit dosage form in ampoules or in multi-dose containers with an optional preservative added. The parenteral preparation can be enclosed in ampoules, disposable syringes or multiple dose vials made of glass, plastic or the like. The formulation can take such forms as suspensions, solutions or emulsions in oily or aqueous vehicles, and can contain formulatory agents such as suspending, stabilizing and/or dispersing agents.

For example, a parenteral preparation can be a sterile injectable solution or suspension in a nontoxic parenterally acceptable diluent or solvent (e.g., as a solution in 1,3-butanediol). Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid can be used in the parenteral preparation.

Alternatively, compounds and bioconjugates of the present invention can be formulated in powder form for constitution with a suitable vehicle, such as sterile pyrogen-free water, before use. For example, a compound/bioconjugate suitable for parenteral administration can include a sterile isotonic saline solution containing between 0.1 percent and 90 percent weight per volume of the compound/bioconjugate. By way of example, a solution can contain from about 5 percent to about 20 percent, more preferably from about 5 percent to about 17 percent, more preferably from about 8 to about 14 percent, and still more preferably about 10 percent weight per volume of the compound/bioconjugate. The solution or powder preparation can also include a solubilizing agent and a local anesthetic such as lignocaine to ease pain at the site of the injection. Other methods of parenteral delivery of compounds/bioconjugates will be known to the skilled artisan and are within the scope of the invention.

(ii) Oral Administration

For oral administration, a compound/bioconjugate of the invention can be formulated to take the form of tablets or capsules prepared by conventional means with one or more pharmaceutically acceptable carriers (e.g., excipients such as binding agents, fillers, lubricants and disintegrants).

(iii) Controlled-Release Administration

Controlled-release (or sustained-release) preparations can be formulated to extend the activity of a compound/bioconjugate and reduce dosage frequency. Controlled-release preparations can also be used to effect the time of onset of action or other characteristics, such as blood levels of the compound/bioconjugate, and consequently affect the occurrence of side effects.

Controlled-release preparations can be designed to initially release an amount of a compound/bioconjugate that produces the desired therapeutic effect, and gradually and continually release other amounts of the compound/bioconjugate to maintain the level of therapeutic effect over an extended period of time. In order to maintain a near-constant level of a compound/bioconjugate in the body, the compound/bioconjugate can be released from the dosage form at a rate that will replace the amount of compound/bioconjugate being metabolized and/or excreted from the body. The controlled-release of a compound/bioconjugate can be stimulated by various inducers, e.g., change in pH, change in temperature, enzymes, water, and/or other physiological conditions or molecules.

Controlled-release systems can include, for example, an infusion pump which can be used to administer the compound/bioconjugate in a manner similar to that used for delivering insulin or chemotherapy to the body generally, or to specific organs or tumors. Typically, using such a system, the compound/bioconjugate is administered in combination with a biodegradable, biocompatible polymeric implant that releases the compound/bioconjugate over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target (e.g., organ, tissue, or group of cells), thus requiring only a fraction of a systemic dosage.

Compounds/bioconjugates of the invention can be administered by other controlled-release means or delivery devices that are well known to those of ordinary skill in the art. These include, for example, hydropropylmethyl cellulose, other polymer matrices, gels, permeable membranes, osmotic systems, multilayer coatings, microparticles, liposomes, microspheres, or the like, or a combination of any of the above to provide the desired release profile in varying proportions. Other methods of controlled-release delivery of compounds/bioconjugates will be known to the skilled artisan and are within the scope of the invention.

(iv) Inhalation Administration

Compounds/bioconjugates of the invention can be administered directly to the lung of a patient/subject by inhalation. For administration by inhalation, a compound/bioconjugate can be conveniently delivered to the lung by a number of different devices. For example, a Metered Dose Inhaler ("MDI") which utilizes canisters that contain a suitable low boiling point propellant, e.g., dichlorodifluoromethane, trichlorofluoromethane, dichlorotetrafluoroethane, carbon dioxide or other suitable gas can be used to deliver a compound/bioconjugate directly to the lung. MDI devices are available from a number of suppliers such as 3M Corporation, Aventis, Boehringer Ingleheim, Forest Laboratories, GlaxoSmithKline, Merck & Co. and Vectura.

Alternatively, a Dry Powder Inhaler (DPI) device can be used to administer a compound/bioconjugate to the lung. DPI devices typically use a mechanism such as a burst of gas to create a cloud of dry powder inside a container, which can then be inhaled by the patient. DPI devices are also well known in the art and can be purchased from a number of vendors which include, for example, GlaxoSmithKline, Nektar Therapeutics, Innovata and Vectura. A popular variation is the multiple dose DPI ("MDDPI") system, which allows for the delivery of more than one therapeutic dose. MDDPI devices are available from companies such as AstraZeneca, GlaxoSmithKline, TEVA, Merck & Co., SkyePharma and Vectura. For example, capsules and cartridges of gelatin for use in an inhaler or insufflator can be formulated containing a powder mix of the compound/bioconjugate and a suitable powder base such as lactose or starch for these systems.

Another type of device that can be used to deliver a compound/bioconjugate to the lung is a liquid spray device supplied, for example, by Aradigm Corporation. Liquid spray systems use extremely small nozzle holes to aerosolize liquid compound/bioconjugate formulations that can then be directly inhaled into the lung. For example, a nebulizer device can be used to deliver a compound/bioconjugate to the lung. Nebulizers create aerosols from liquid compound/bioconjugate formulations by using, for example, ultrasonic energy to form fine particles that can be readily inhaled. Examples of nebulizers include devices supplied by Aventis and Battelle.

In another example, an electrohydrodynamic ("EHD") aerosol device can be used to deliver a compoundlbioconjugate to the lung. EHD aerosol devices use electrical energy to aerosolize liquid compoundlbioconjugate solutions or suspensions. The electrochemical properties of the compound/bioconjugate formulation are important parameters to optimize when delivering this compoundlbioconjugate to the lung with an EHD aerosol device. Such optimization is routinely performed by one of skill in the art. Other methods of intra-pulmonary delivery of compounds/bioconjugates will be known to the skilled artisan and are within the scope of the invention.

Liquid compound/bioconjugate formulations suitable for use with nebulizers and liquid spray devices and EHD aerosol devices will typically include the compound/bioconjugate with a pharmaceutically acceptable carrier. In one exemplary embodiment, the pharmaceutically acceptable carrier is a liquid such as alcohol, water, polyethylene glycol or a perfluorocarbon. Optionally, another material can be added to alter the aerosol properties of the solution or suspension of the compound/bioconjugate. For example, this material can be a liquid such as an alcohol, glycol, polyglycol or a fatty acid. Other methods of formulating liquid compound/bioconjugate solutions or suspensions suitable for use in aerosol devices are known to those of skill in the art.

(v) Depot Administration

A compound/bioconjugate of the invention can be formulated as a depot preparation. Such long-acting formulations can be administered by implantation (e.g., subcutaneously or intramuscularly) or by intramuscular injection. Accordingly, the compound/bioconjugate can be formulated with suitable polymeric or hydrophobic materials such as an emulsion in an acceptable oil or ion exchange resin, or as sparingly soluble derivatives such as a sparingly soluble salt. Other methods of depot delivery of compounds/bioconjugates will be known to the skilled artisan and are within the scope of the invention.

(vi) Topical Administration

For topical application, a compound/bioconjugate can be combined with a pharmaceutically acceptable carrier so that an effective dosage is delivered, based on the desired activity ranging from an effective dosage, for example, of 1.0 µM to 1.0 mM. In one aspect of the invention, a topical formulation of a compound/bioconjugate can be applied to the skin. The pharmaceutically acceptable carrier can be in the form of, for example, and not by way of limitation, an ointment, cream, gel, paste, foam, aerosol, suppository, pad or gelled stick.

A topical formulation can include a therapeutically effective amount of a compound/bioconjugate in an ophthalmologically acceptable excipient such as buffered saline, mineral oil, vegetable oils such as corn or arachis oil, petroleum jelly, Miglyol 182, alcohol solutions, or liposomes or liposome-like products. Any of these formulations of such compounds/bioconjugates can include preservatives, antioxidants, antibiotics, immunosuppressants, and other, biologically or pharmaceutically effective agents that do not exert a significant detrimental effect on the compouncl/bioconjugate. Other methods of topical delivery of compounds/bioconjugates will be known to the skilled artisan and are within the scope of the invention.

(vii) Rectal Administration

Compounds/bioconjugates of the invention can be formulated in rectal formulations such as suppositories or retention enemas that include conventional suppository bases such as cocoa butter or other glycerides and/or binders and/or carriers such as triglycerides, microcrystalline cellulose, gum tragacanth or gelatin. Rectal formulations can contain a compound/bioconjugate in the range of 0.5% to 10% by weight, for example. Other methods of rectal delivery of compounds/bioconjugates will be known to the skilled artisan and are within the scope of the invention.

(viii) Other Systems of Administration

Various other delivery systems are known in the art and can be used to administer the compounds/bioconjugates of the invention. Moreover, these and other delivery systems can be combined and/or modified to promote optimization of the administration of compounds/bioconjugates of the present invention. Exemplary formulations that include compounds/bioconjugates of the present invention are described elsewhere herein (the compounds/bioconjugates of the present invention are indicated as the active ingredient, but those of skill in the art will recognize that pro-drugs and compound combinations are also meant to be encompassed by this term).

4d: Formulation

In an embodiment, the invention provides a medicament which comprises a therapeutically effective amount of one or more compositions of the invention, such as a compound of any one of formulas (FX1)-(FX41). In an embodiment, the invention provides a medicament which comprises a diagnostically effective amount of one or more compositions of the invention. In an embodiment, the invention provides a method for making a medicament for treatment of a condition described herein, such as the treatment of cancer, inflammation, stenosis or a vascular disease. In an embodiment, the invention provides a method for making a medicament for diagnosis or aiding in the diagnosis of a condition described herein, such as the diagnosis of cancer, inflammation, stenosis or a vascular disease. In an embodiment, the invention provides the use of one or more compositions set forth herein for the making of a medicament for the treatment of cancer, inflammation, stenosis or a vascular disease. In an embodiment, the invention provides the use of one or more compositions set forth herein for the treatment of a disease. In an embodiment, the invention provides the use of one or more compositions set forth herein for the diagnosis of a disease. Compositions of the invention include formulations and preparations comprising one or more of the present optical agents provided in an aqueous solution, such as a pharmaceutically acceptable formulation or preparation. Optionally, compositions of the invention further comprise one or more pharmaceutically acceptable surfactants, buffers, electrolytes, salts, carriers, binders, coatings, preservatives and/or excipients.

In an embodiment, the invention provides a pharmaceutical formulation having an active ingredient comprising a composition of the invention, such as a compound of any one of formulas (FX1)-(FX41). In an embodiment, the invention provides a method of synthesizing a composition of the invention or a pharmaceutical formulation thereof, such as a compound of any one of formulas (FX1)-(FX41). In an embodiment, a pharmaceutical formulation comprises one or more excipients, carriers, diluents, and/or other components as would be understood in the art. Preferably, the components meet the standards of the National Formulary ("NF"), United States Pharmacopoeia ("USP"; United States Pharmacopeial Convention Inc., Rockville, Md.), or Handbook of Pharmaceutical Manufacturing Formulations (Sarfaraz K. Niazi, all volumes, ISBN: 9780849317521, ISBN 10: 0849317525; CRC Press, 2004). See, e.g., United States Pharmacopeia and National Formulary (USP 30-NF 25), Rockville, Md.: United States Pharmacopeia] Convention (2007 and 2008), and each of any earlier editions; The Handbook of Pharmaceutical Excipients, published jointly by the American Pharmacists Association and the Pharmaceutical Press (Pharmaceutical Press (2005) (ISBN-10: 0853696187, ISBN-13: 978-0853696186)); Merck Index, Merck & Co., Rahway, N.J.; and Gilman et al., (eds) (1996); Goodman and Gilman's: The Pharmacological Bases of Therapeutics, 8th Ed., Pergamon Press. In embodiments, the formulation base of the formulations of the invention comprises physiologically acceptable excipients, namely, at least one binder and optionally other physiologically acceptable excipients. Physiologically acceptable excipients are those known to be usable in the pharmaceutical technology sectors and adjacent areas, particularly, those listed in relevant pharmacopeias (e.g. DAB, Ph. Eur., BP, NF, USP), as well as other excipients whose properties do not impair a physiological use.

This invention also is directed, in part, to pharmaceutical compositions including a therapeutically effective amount of a compound or salt of this invention, as well as processes for making such compositions. Such compositions generally include one or more pharmaceutically acceptable carriers (e.g., excipients, vehicles, auxiliaries, adjuvants, diluents) and can include other active ingredients. Formulation of these compositions can be achieved by various methods known in the art. A general discussion of these methods can be found in, for example, Hoover, John E., Remington's Pharmaceutical Sciences (Mack Publishing Co., Easton, Pa.: 1975). See also, Lachman, L., eds., Pharmaceutical Dosage Forms (Marcel Decker, New York, N. Y., 1980).

The diagnostic and therapeutic formulations of this invention and medicaments of this invention can further comprise one or more pharmaceutically acceptable carriers, excipients, buffers, emulsifiers, surfactants, electrolytes or diluents. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985).

Compositions of the invention include formulations and preparations comprising one or more of the present compounds provided in an aqueous solution, such as a pharmaceutically acceptable formulation or preparation. Optionally, compositions of the invention further comprise one or more pharmaceutically acceptable surfactants, buffers, electrolytes, salts, carriers, binders, coatings, preservatives and/or excipients.

Compounds and bioconjugates of the present invention can be formulated by known methods for administration to a subject using several routes which include, but are not limited to, parenteral, oral, topical, intradermal, intramuscular, intraperitoneal, intravenous, subcutaneous, intranasal, epidural, and ophthalmic routes. An individual compound/bioconjugate can be administered in combination with one or more additional compounds/bioconjugates of the present invention and/or together with other biologically active or biologically inert agents. Such biologically active or inert agents can be in fluid or mechanical communication with the compound(s)/bioconjugate(s) or attached to the compound(s)/bioconjugate(s) by ionic, covalent, Van der Waals, hydrophobic, hydrophilic or other physical forces. It is preferred that administration is localized in a subject, but administration can also be systemic.

Compounds and bioconjugates of the present invention can be formulated by any conventional manner using one or more pharmaceutically acceptable carriers. Thus, the compound(s)/bioconjugate(s) and their pharmaceutically acceptable salts and solvates can be specifically formulated for administration, e.g., by inhalation or insufflation (either through the mouth or the nose) or oral, buccal, parenteral or rectal administration. The compounds/bioconjugates can take the form of charged, neutral and/or other pharmaceutically acceptable salt forms. Examples of pharmaceutically acceptable carriers include, but are not limited to, those described in REMINGTON'S PHARMACEUTICAL SCIENCES (A.R. Gennaro, Ed.), 20th edition, Williams & Wilkins Pa., USA (2000).

Compounds and bioconjugates of the present invention can be formulated in the form of solutions, suspensions, emulsions, tablets, pills, capsules, powders, controlled- or sustained-release formulations and the like. Such formulations will contain a therapeutically effective amount of the compound/bioconjugate, preferably in purified form, together with a suitable amount of carrier so as to provide the form for proper administration to the patient. The formulation should suit the mode of administration.

Pharmaceutically acceptable carriers that can be used in conjunction with the compounds of the invention are well known to those of ordinary skill in the art. Carriers can be selected based on a number of factors including, for example, the particular diaza compound(s) or pharmaceutically acceptable salt(s) used; the compound's concentration, stability, and intended bioavailability; the condition being treated; the subject's age, size, and general condition; the route of administration; etc. A general discussion related to carriers can be found in, for example, J. G. Nairn, Remington's Pharmaceutical Science, pp. 1492-1517 (A. Gennaro, ed., Mack Publishing Co., Easton, Pa. (1985)).

Solid dosage forms for oral administration include, for example, capsules, tablets, gelcaps, pills, dragees, troches, powders, granules, and lozenges. In such solid dosage forms, the compounds or pharmaceutically acceptable salts thereof can be combined with one or more pharmaceutically acceptable carriers. The compounds and pharmaceutically acceptable salts thereof can be mixed with carriers including, but not limited to, lactose, sucrose, starch powder, corn starch, potato starch, magnesium carbonate, microcrystalline cellulose, cellulose esters of alkanoic acids, cellulose alkyl esters, talc, stearic acid, magnesium stearate, magnesium oxide, sodium and calcium salts of phosphoric and sulfuric acids, sodium carbonate, agar, mannitol, sorbitol, sodium saccharin, gelatin, acacia gum, alginic acid, sodium alginate, tragacanth, colloidal silicon dioxide, croscarmellose sodium, polyvinylpyrrolidone, and/or polyvinyl alcohol, and then tableted or encapsulated for convenient administration. Such capsules or tablets can contain a controlled-release formulation, as can be provided in a dispersion of the compound or salt in hydroxypropylmethyl cellulose. In the case of capsules, tablets, and pills, the dosage forms also can include buffering agents, such as sodium citrate, or magnesium or calcium carbonate or bicarbonate. Tablets and pills additionally can, for example, include a coating (e.g., an enteric coating) to delay disintegration and absorption. The concentration of the diaza compound in a solid oral dosage form can be from about 5 to about 50% for example, and in certain aspects from about 8 to about 40%, and in another aspect from about 10 to about 30% by weight based on the total weight of the composition.

Liquid dosage forms of the compounds of the invention for oral administration include, for example, pharmaceutically acceptable emulsions, solutions, suspensions, syrups, and elixirs containing inert diluents commonly used in the art (e.g., water). Such compositions also can include adjuvants, such as wetting, emulsifying, suspending, flavoring (e.g., sweetening), and/or perfuming agents. The concentration of the diaza compound in the liquid dosage form can be from about 0.01 to about 5 mg, and in certain aspects from about 0.01 to about 1 mg, and in another aspect from about 0.01 to about 0.5 mg per ml of the composition. Low concentrations of the compounds of the invention in liquid dosage form can be prepared in the case that the diaza compound is more soluble at low concentrations. Techniques for making oral dosage forms useful in the invention are generally described in, for example, Modern Pharmaceutics, Chapters 9 and 10 (Banker & Rhodes, Editors (1979)). See also, Lieberman et al., Pharmaceutical Dosage Forms: Tablets (1981). See also, Ansel, Introduction to Pharmaceutical Dosage Forms (2nd Edition (1976)).

In some aspects of the invention, tablets or powders for oral administration can be prepared by dissolving the diaza compound in a pharmaceutically acceptable solvent capable of dissolving the compound to form a solution and then evaporating when the solution is dried under vacuum. A carrier can also be added to the solution before drying. The resulting solution can be dried under vacuum to form a glass. The glass can then be mixed with a binder to form a powder. This powder can be mixed with fillers or other conventional tableting agents, and then processed to form a tablet. Alternatively, the powder can be added to a liquid carrier to form a solution, emulsion, suspension, or the like.

In some aspects, solutions for oral administration are prepared by dissolving the diaza compound in a pharmaceutically acceptable solvent capable of dissolving the compound to form a solution. An appropriate volume of a carrier is added to the solution while stirring to form a pharmaceutically acceptable solution for oral administration.

In some embodiments, a liposome or micelle can be utilized as a carrier or vehicle for the composition. For example, in some embodiments, the diaza compound can be a part of the lipophilic bilayers or micelle, and the targeting ligand, if present, can be on the external surface of the liposome or micelle. As another example, a targeting ligand can be externally attached to the liposome or micelle after formulation for targeting the liposome or micelle (which contains the diaza optical agents) to the desired tissue, organ, or other site in the body.

Injectable preparations (e.g., sterile injectable aqueous or oleaginous suspensions) can be formulated according to the known art using suitable dispersing, wetting agents, and/or suspending agents. Acceptable vehicles for parenteral use include both aqueous and nonaqueous pharmaceutically-acceptable solvents. Suitable pharmaceutically acceptable aqueous solvents include, for example, water, saline solutions, dextrose solutions (such as DW5), electrolyte solutions, etc.

In one embodiment, the present diaza compounds are formulated as nanoparticles or microparticles. Use of such nanoparticle or microparticle formulations can be beneficial for some applications to enhance delivery, localization, target specificity, administration, etc. of the diaza compound. Potentially useful nanoparticles and microparticles include, but are not limited to, micelles, liposomes, microemulsions, nanoemulsions, vesicles, tubular micelles, cylindrical micelles, bilayers, folded sheets structures, globular aggregates, swollen micelles, inclusion complex, encapsulated droplets, microcapsules, nanocapsules or the like. As will be understood by those having skill in the art, the present diaza compounds can be located inside the nanoparticle or microparticle, within a membrane or wall of the nanoparticle or microparticle, or outside of (but bonded to or otherwise associated with) the nanoparticle or microparticle. The agent formulated in nanoparticles or microparticles can be administered by any of the routes previously described. In a formulation applied topically, the diaza compound is slowly released over time. In an injectable formulation, the liposome, micelle, capsule, etc., circulates in the bloodstream and is delivered to the desired site (e.g., target tissue).

Preparation and loading of nanoparticles and microparticles are well known in the art. As one example, liposomes can be prepared from dipalmitoyl phosphatidylcholine (DPPC) or egg phosphatidylcholine (PC) because this lipid has a low heat transition. Liposomes are made using standard procedures as known to one skilled in the art (e.g., Braun-Falco et al., (Eds.), Griesbach Conference, Liposome Dermatics, Springer-Verlag, Berlin (1992), pp. 69 81; 91 117.

Polycaprolactone, poly(glycolic) acid, poly(lactic) acid, polyanhydride or lipids can be formulated as microspheres. As an illustrative example, the present diaza compounds can be mixed with polyvinyl alcohol (PVA), the mixture then dried and coated with ethylene vinyl acetate, then cooled again with PVA. In a liposome, the present diaza compounds can be within one or both lipid bilayers, in the aqueous between the bilayers, or within the center or core. Liposomes can be modified with other molecules and lipids to form a cationic liposome. Liposomes can also be modified with lipids to render their surface more hydrophilic which increases their circulation time in the bloodstream. The thus-modified liposome has been termed a "stealth" liposome, or a long-lived liposome, as described in U.S. Pat. No. 6,258,378, and in Stealth Liposomes, Lasic and Martin (Eds.) 1995 CRC Press, London. Encapsulation methods include detergent dialysis, freeze drying, film forming, injection, as known to one skilled in the art and disclosed in, for example, U.S. Pat. No. 6,406,713. Optionally, the present compositions and methods include a micelle delivery system, for example, involving one or more PEG-based amphiphilic polymers developed for drug delivery including: PEG-poly(E-caprolactone), PEG-poly(amino acid), PEG-polylactide or PEG-phospholipid constructs; a cross linked poly(acrylic acid) polymer system, a phospholipid-based system and/or block copolymer systems comprising one or more of the following polymer blocks: a poly(lactic acid) polymer block; a poly(propylene glycol) polymer block; a poly(amino acid) polymer block; a poly(ester) polymer block; a poly (E-caprolactone) polymer block; a poly(ethylene glycol) block, a poly(acrylic acid) block; a polylactide block; a polyester block; a polyamide block; a polyanhydride block; a polyurethane block; a polyimine block; a polyurea block; a polyacetal block; a polysaccharide block; and a polysiloxane block.

Suitable pharmaceutically-acceptable nonaqueous solvents include, but are not limited to, the following (as well as mixtures thereof):

(i) Alcohols (these include, for example, α-glycerol formal, β-glycerol formal, 1,3-butyleneglycol, aliphatic or aromatic alcohols having from 2 to about 30 carbons (e.g., methanol, ethanol, propanol, isopropanol, butanol, t-butanol, hexanol, octanol, amylene hydrate, benzyl alcohol, glycerin (glycerol), glycol, hexylene, glycol, tetrahydrofuranyl alcohol, cetyl alcohol, and stearyl alcohol), fatty acid esters of fatty alcohols (e.g., polyalkylene glycols, such as polypropylene glycol and polyethylene glycol), sorbitan, sucrose, and cholesterol);

(ii) Amides, which include, for example, dimethylacetamide (DMA), benzyl benzoate DMA, dimethylformamide, N-hydroxyethyO-lactamide, N,N-dimethylacetamide-amides, 2-pyrrolidinone, 1-methyl-2-pyrrolidinone, and polyvinylpyrrolidone;

(iii) Esters, which include, for example, acetate esters (e.g., monoacetin, diacetin, and triacetin), aliphatic and aromatic esters (e.g., ethyl caprylate or octanoate, alkyl oleate, benzyl benzoate, or benzyl acetate), dimethylsulfoxide (DMSO), esters of glycerin (e.g., mono, di, and tri-glyceryl citrates and tartrates), ethyl benzoate, ethyl acetate, ethyl carbonate, ethyl lactate, ethyl oleate, fatty acid esters of sorbitan, glyceryl monostearate, glyceride esters (e.g., mono, di, or tri-glycerides), fatty acid esters (e.g., isopropyl myristrate), fatty acid derived PEG esters (e.g., PEG-hydroxyoleate and PEG-hydroxystearate), N-methyl pyrrolidinone, pluronic 60, polyoxyethylene sorbitol oleic polyesters (e.g., poly(ethoxylated)$_{30-60}$ sorbitol poly(oleate)$_{2-4}$, poly(oxyethylene)$_{15-20}$ monooleate, poly(oxyethylene)$_{15-20}$ mono 12-hydroxystearate, and poly(oxyethylene)$_{15-20}$ mono ricinoleate), polyoxyethylene sorbitan esters (e.g., polyoxyethylene-sorbitan monooleate, polyoxyethylene-sorbitan monopalmitate, polyoxyethylene-sorbitan monolaurate, polyoxyethylene-sorbitan monostearate, and POLYSORBATE 20, 40, 60, and 80 (from ICI Americas, Wilmington, Del.)), polyvinylpyrrolidone, alkyleneoxy modified fatty acid esters (e.g., polyoxyl 40 hydrogenated castor oil and polyoxyethylated castor oils, such as CREMOPHOR EL solution or CREMOPHOR RH 40 solution), saccharide fatty acid esters (i.e., the condensation product of a monosaccharide (e.g., pentoses, such as, ribose, ribulose, arabinose, xylose, lyxose, and xylulose; hexoses, such as glucose, fructose, galactose, mannose, and sorbose; trioses; tetroses; heptoses; and octoses), disaccharide (e.g., sucrose, maltose, lactose, and trehalose), oligosaccharide, or a mixture thereof with one or more $C_4$-$C_{22}$ fatty acids (e.g., saturated fatty acids, such as caprylic acid, capric acid, lauric acid, myristic acid, palmitic acid, and stearic acid; and unsaturated fatty acids, such as palmitoleic acid, oleic acid, elaidic acid, erucic acid, and linoleic acid), and steroidal esters;

(iv) Ethers, for example, alkyl, aryl, and cyclic ethers having from 2 to about 30 carbons. Examples include diethyl ether, tetrahydrofuran, dimethyl isosorbide, diethylene glycol monoethyl ether), and giycofurol (tetrahydrofurfuranyl alcohol polyethylene glycol ether);

(v) Ketones which typically have from about 3 to about 30 carbons. Examples include acetone, methyl ethyl ketone, and methyl isobutyl ketone;

(vi) Hydrocarbons which are typically aliphatic, cycloaliphatic, or aromatic hydrocarbons having from about 4 to about 30 carbons. Examples include benzene, cyclohexane, dichloromethane, dioxolanes, hexane, n-decane, n-dodecane, n-hexane, sulfolane, tetramethylenesulfone, tetramethylenesulfoxide, toluene, dimethylsulfoxide (DMSO); and tetramethylene sulfoxide;

(vii) Oils which include, for example, oils of mineral, vegetable, animal, essential, or synthetic origin. These include: mineral oils, such as aliphatic and wax-based hydrocarbons, aromatic hydrocarbons, mixed aliphatic and aromatic based hydrocarbons, and refined paraffin oil; vegetable oils, such as linseed, tung, safflower, soybean, castor, cottonseed, groundnut, rapeseed, coconut, palm, olive, corn, corn germ, sesame, persic, and peanut oil; glycerides, such as mono-, di-, and triglycerides; animal oils, such as fish, marine, sperm, cod-liver, haliver, squaiene, squalane, and shark liver oil; oleic oils; and polyoxyethylated castor oil;

(viii) Alkyl, alkenyl, or aryl halides which include, for example, alkyl or aryl halides having from 1 to about 30 carbons and one or more halogen substituents. Examples include: methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (SOLUTOL HS-15, from BASF, Ludwigshafen, Germany); polyoxyethylene glycerol; sodium laurate; sodium oleate; and sorbitan monooleate.

Other pharmaceutically acceptable solvents for use in the invention are well known to those of ordinary skill in the art. General discussion relating to such solvents can be found in, for example, The Chemotherapy Source Book (Williams & Wilkens Publishing), The Handbook of Pharmaceutical Excipients, (American Pharmaceutical Association, Washington, D.C., and The Pharmaceutical Society of Great Britain, London, England, 1968), Modern Pharmaceutics 3d ed., (G. Banker et. al., eds., Marcel Dekker, Inc., New York, New York (1995)), The Pharmacological Basis of Therapeutics, (Goodman & Gilman, McGraw Hill Publishing), Pharmaceutical Dosage Forms, (H. Lieberman et. al., eds., Marcel Dekker, inc., New York, New York (1980)), Remington's Pharmaceutical Sciences, 19th ed., (A. Gennaro, ed., Mack Publishing, Easton, Pa., (1995)), The United States Pharmacopeia 24, The National Formulary 19, (National Publishing, Philadelphia, Pa. (2000)); Spiegel, A.J., et al., "Use of Nonaqueous Solvents in Parenteral Products," J. Pharma. Sciences, Vol. 52, No. 10, pp. 917-927 (1963).

Solvents useful in the invention include, but are not limited to, those known to stabilize diaza compounds or pharmaceutically acceptable salts thereof. These can include, for example, oils rich in triglycerides, such as safflower oil, soybean oil, and mixtures thereof; and alkyleneoxy-modified fatty acid esters, such as polyoxyl 40 hydrogenated castor oil and polyoxyethylated castor oils (e.g., CREMOPHOR EL solution or CREMOPHOR RH 40 solution). Commercially available triglycerides include INTRALIPID emulsified soybean oil (Kabi-Pharmacia Inc., Stockholm, Sweden), NUTRALIPID emulsion (McGaw, Irvine, California), LIPOSYN II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), LIPOSYN III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels of from about 25 to about 100% (by weight based on the total fatty acid content) (DHASCO from Martek Biosciences Corp., Columbia, MD; DHA MAGURO from Daito Enterprises, Los Angeles, CA; SOYACAL; and TRAVEMULSION). Ethanol in particular is a useful solvent for dissolving a diaza compound or pharmaceutically acceptable salt thereof to form solutions, emulsions, and the like.

Additional components can be included in the compositions of this invention for various purposes generally known in the pharmaceutical industry. These components tend to impart properties that, for example, enhance retention of the diaza compound or salt at the site of administration, protect the stability of the composition, control the pH, and facilitate processing of the diaza compound or salt into pharmaceutical formulations, and the like Specific examples of such components include cryoprotective agents; agents for preventing reprecipitation of the diaza compound or salt surface; active, wetting, or emulsifying agents (e.g., lecithin, polysorbate-80, TWEEN 80, pluronic 60, and polyoxyethylene stearate); preservatives (e.g., ethyl-p-hydroxybenzoate); microbial preservatives (e.g., benzyl alcohol, phenol, m-cresol, chlorobutanol, sorbic acid, thimerosal, and paraben): agents for adjusting pH or buffering agents (e.g., acids, bases, sodium acetate, sorbitan monolaurate, etc.); agents for adjusting osmolarity (e.g., glycerin); thickeners (e.g., aluminum monostearate, stearic acid, cetyl alcohol, stearyl alcohol, guar gum, methyl cellulose, hydroxypropylcellulose, tristearin, cetyl wax esters, polyethylene glycol, etc.); colorants; dyes; flow aids; non-volatile silicones (e.g., cyclomethicone); clays (e.g., bentonites); adhesives; bulking agents; flavorings; sweeteners; adsorbents; fillers (e.g., sugars such as lactose, sucrose, mannitol, sorbitol, cellulose, calcium phosphate, etc.); diluents (e.g., water, saline, electrolyte solutions, etc.); binders (e.g., gelatin; gum tragacanth; methyl cellulose; hydroxypropyl methylcellulose; sodium carboxymethyl cellulose; polyvinylpyrrolidone; sugars; polymers; acacia; starches, such as maize starch, wheat starch, rice starch, and potato starch; etc.); disintegrating agents (e.g., starches, such as maize starch, wheat starch, rice starch, potato starch, and carboxymethyl starch; cross-linked polyvinyl pyrrolidone; agar; alginic acid or a salt thereof, such as sodium alginate; croscarmellose sodium; crospovidone; etc); lubricants (e.g., silica; talc; stearic acid and salts thereof, such as magnesium stearate; polyethylene glycol; etc.); coating agents (e.g., concentrated sugar solutions including gum arabic, talc, polyvinyl pyrrolidone, carbopol gel, polyethylene glycol, titanium dioxide, etc.); and antioxidants (e.g., sodium metabisulfite, sodium bisulfite, sodium sulfite, dextrose, phenols, thiophenols, etc.).

Techniques and compositions for making parenteral dosage forms are generally known in the art. Formulations for parenteral administration can be prepared from one or more sterile powders and/or granules having a compound or salt of this invention and one or more of the carriers or diluents mentioned for use in the formulations for oral administration. The powder or granule typically is added to an appropriate volume of a solvent (typically while agitating (e.g., stirring) the solvent) that is capable of dissolving the powder or granule. Particular solvents useful in the invention include, for example, water, polyethylene glycol, propylene glycol, ethanol, corn oil, cottonseed oil, peanut oil, sesame oil, benzyl alcohol, sodium chloride, and/or various buffers.

Emulsions for parenteral administration can be prepared by, for example, dissolving a compound or salt of this invention in any pharmaceutically acceptable solvent capable of dissolving the compound to form a solution; and adding an appropriate volume of a carrier to the solution while stirring to form the emulsion. Solutions for parenteral administration can be prepared by, for example, dissolving a compound or salt of this invention in any pharmaceutically acceptable solvent capable of dissolving the compound to form a solution; and adding an appropriate volume of a carrier to the solution while stirring to form the solution.

Suppositories for rectal administration can be prepared by, for example, mixing the drug with a suitable nonirritating excipient that is solid at ordinary temperatures, but liquid at the rectal temperature and will therefore melt in the rectum to release the drug. Suitable excipients include, for example, cocoa butter; synthetic mono-, di-, or triglycerides; fatty acids; and/or polyethylene glycols.

Every formulation or combination of components described or exemplified herein can be used to practice the invention, unless otherwise stated.

(i) Binding Agents

Binding agents include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof. Suitable forms of microcrystalline cellulose include, for example, the materials sold as AVICEL-PH-101, AVICEL-PH-103 and AVICEL-PH-105 (available from FMC Corporation, American Viscose Division, Avicel Sales, Marcus Hook, Pennsylvania, USA). An exemplary suitable binder is a mixture of microcrystalline cellulose and sodium carboxymethyl cellulose sold as AVICEL RC-581 by FMC Corporation.

(ii) Fillers

Fillers include, but are not limited to, talc, calcium carbonate (e.g., granules or powder), lactose, microcrystalline cellulose, powdered cellulose, dextrates, kaolin, mannitol, silicic acid, sorbitol, starch, pre-gelatinized starch, and mixtures thereof.

(iii) Lubricants

Lubricants include, but are not limited to, calcium stearate, magnesium stearate, mineral oil, electromagnetic radiation mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, and mixtures thereof. Additional lubricants include, for example, a syloid silica gel (AEROSIL 200, manufactured by W.R. Grace Co. of Baltimore, Md., USA), a coagulated aerosol of synthetic silica (marketed by Deaussa Co. of Plano, Tex., USA), CAB-O-SIL (a pyrogenic silicon dioxide product sold by Cabot Co. of Boston, Mass., USA), and mixtures thereof.

(iv) Disintegrants

Disintegrants include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Tablets or capsules can optionally be coated by methods well known in the art. If binders and/or fillers are used with a compound/bioconjugate of the invention, they are typically formulated as about 50 to about 99 weight percent of the compoundlbioconjugate. In one aspect, about 0.5 to about 15 weight percent of disintegrant, and particularly about 1 to about 5 weight percent of disintegrant, can be used in combination with the compound. A lubricant can optionally be added, typically in an amount of less than about 1 weight percent of the compound/bioconjugate. Techniques and pharmaceutically acceptable additives for making solid oral dosage forms are described in Marshall, SOLID ORAL DOSAGE FORMS, Modern Pharmaceutics (Banker and Rhodes, Eds.), 7:359-427 (1979). Other formulations are known in the art.

Liquid preparations for oral administration can take the form of solutions, syrups or suspensions. Alternatively, the liquid preparations can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and/or preservatives (e.g., methyl or propyl-p-hydroxybenzoates or sorbic acid). The preparations can also contain buffer salts, flavoring, coloring, perfuming and sweetening agents as appropriate. Preparations for oral administration can also be formulated to achieve controlled release of the compound/bioconjugate. Oral formulations preferably contain 10% to 95% compound/bioconjugate. In addition, a compound/bioconjugate of the present invention can be formulated for buccal administration in the form of tablets or lozenges formulated in a conventional manner. Other methods of oral delivery of compounds/bioconjugates of the invention will be known to the skilled artisan and are within the scope of the invention. Formulation 1

Hard gelatin capsules are prepared using the following ingredients:

TABLE F1

| Ingredients | (mg/capsule) |
|---|---|
| Active Ingredient | 250.0 |
| Starch | 305.0 |
| Magnesium stearate | 5.0 |

The above ingredients are mixed and filled into hard gelatin capsules in 560 mg quantities. Formulation 2

A tablet formula is prepared using the following ingredients:

TABLE F2

| Ingredients | (mg/tablet) |
|---|---|
| Active Ingredient | 250.0 |
| Cellulose, microcrystalline | 400.0 |
| Colloidal silicon dioxide | 10.0 |
| Stearic acid | 5.0 |

The components are blended and compressed to form tablets, each weighing 665 mg. Formulation 3

A dry powder inhaler formulation is prepared containing the following components:

TABLE F3

| Ingredients | Weight % |
|---|---|
| Active ingredient | 5 |
| Lactose | 95 |

The active ingredient is mixed with the lactose and the mixture is added to a dry powder inhaling appliance. Formulation 4

Tablets, each containing 60 mg of active ingredient, are prepared as follows:

TABLE F4

| Ingredients | milligrams |
|---|---|
| Active ingredient | 60.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 150.0 |

The active ingredient, starch and cellulose are passed through a No. 20 mesh U.S. sieve and mixed thoroughly. The solution of polyvinylpyrrolidone is mixed with the resultant powders which are then passed through a 16 mesh U.S. sieve. The granules as produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg. Formulation 5

Capsules, each containing 80 mg of active ingredient are made as follows:

TABLE F5

| Ingredients | milligrams |
|---|---|
| Active ingredient | 80.0 |
| Starch | 109.0 |
| Magnesium stearate | 1.0 |
| Total | 190.0 |

The active ingredient, cellulose, starch, and magnesium stearate are blended, passed through a No. 20 mesh U.S. sieve, and filled into hard gelatin capsules in 190 mg quantities. Formulation 6

Suppositories, each containing 225 mg of active ingredient, are made as follows:

TABLE F6

| Ingredients | milligrams |
|---|---|
| Active Ingredient | 225 |
| Saturated fatty acid glycerides to | 2000 |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation 7

Suspensions, each containing 50 mg of active ingredient per 5.0 ml dose are made as follows:

TABLE F7

| Ingredients | milligrams |
|---|---|
| Active ingredient | 50.0 mg |
| Xanthan gum | 4.0 mg |
| Sodium carboxymethyl cellulose | (11%) |
| Microcrystalline cellulose | (89%) 50.0 mg |
| Sucrose | 1.75 g |
| Sodium benzoate | 10.0 mg |
| Flavor | q.v. |
| Color | q.v. |
| Purified water to | 5.0 ml |

The active ingredient, sucrose and xantham gum are blended, passed through a No. 10 mesh U.S. sieve, and mixed with a previously made solution of the microcrystalline cellulose and sodium carboxymethyl cellulose in water. The sodium benzoate, flavor, and color are diluted with some of the water and added with stirring. Sufficient water is then added to produce the required volume. Formulation 8

Capsules, each containing 150 mg of active ingredient, are made as follows:

TABLE F8

| Ingredients | milligrams |
|---|---|
| Active ingredient | 150.0 |
| Starch | 407.0 |
| Magnesium stearate | 3.0 |
| Total | 560.0 |

The active ingredient, cellulose, starch, and magnesium stearate are blended, passed through a No. 20 mesh U.S. sieve, and filled into hard gelatin capsules in 560 mg quantities. 3f: Kits Various embodiments of the present invention include kits. Such kits can include a compound/bioconjugate of the present invention, optionally one or more ingredients for preparing a pharmaceutically acceptable formulation of the compoundlbioconjugate, and instructions for use (e.g., administration). When supplied as a kit, different components of a compound/bioconjugate formulation can be packaged in separate containers and admixed immediately before use. Such packaging of the components separately can, if desired, be presented in a pack or dispenser device which can contain one or more unit dosage forms containing the compound/bioconjugate. The pack can, for example, comprise metal or plastic foil such as a blister pack. Such packaging of the components separately can also, in certain instances, permit long-term storage without losing activity of the components. In addition, if more than one route of administration is intended or more than one schedule for administration is intended, the different components can be packaged separately and not mixed prior to use. In various embodiments, the different components can be packaged in one combination for administration together.

It is further contemplated that the diaza compounds and salts of this invention can be used in the form of a kit that is suitable for use in performing the methods described herein, packaged in a container. The kit can contain the diaza compound or compounds and, optionally, appropriate diluents, devices or device components suitable for administration and instructions for use in accordance with the methods of the invention. The devices can include parenteral injection devices, such as syringes or transdermal patch or the like. Device components can include cartridges for use in injection devices and the like. In one aspect, the kit includes a first dosage form including a diaza compound or salt of this invention and a second dosage form including another active ingredient in quantities sufficient to carry out the methods of the invention. The first dosage form and the second dosage form together can include a therapeutically effective amount of the compounds for treating the targeted condition(s).

In certain embodiments, kits can be supplied with instructional materials. Instructions can be printed on paper or other substrate, and/or can be supplied as an electronic-readable medium, such as a floppy disc, mini-CD-ROM, CD-ROM, DVD-ROM, Zip disc, videotape, audio tape, and the like. Detailed instructions can not be physically associated with the kit; instead, a user can be directed to an Internet web site specified by the manufacturer or distributor of the kit, or supplied as electronic mail.

If desired, the emulsions or solutions described above for oral or parenteral administration can be packaged in IV bags, vials, or other conventional containers in concentrated form, and then diluted with a pharmaceutically acceptable liquid (e.g., saline) to form an acceptable diaza compound concentration before use.

Kits can include reagents in separate containers such as, for example, sterile water or saline to be added to a lyophilized active component packaged separately. For example, sealed glass ampules can contain lyophilized superoxide dismutase mimetics and in a separate ampule, sterile water, sterile saline or sterile each of which has been packaged under a neutral non-reacting gas, such as nitrogen. Ampules can consist of any suitable material, such as glass, organic polymers, such as polycarbonate, polystyrene, ceramic, metal or any other material typically employed to hold reagents. Other examples of suitable containers include bottles that can be fabricated from similar substances as ampules, and envelopes that can consist of foil-lined interiors, such as aluminum or an alloy. Other containers include test tubes, vials, flasks, bottles, syringes, and the like. Containers can have a sterile access port, such as a bottle having a stopper that can be pierced by a hypodermic injection needle. Other containers can have two compartments that are separated by a readily removable membrane that upon removal permits the components to mix. Removable membranes can be glass, plastic, rubber, and the like.

Statements Regarding Incorporation by Reference and Variations

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Optical agents of the present invention may be formulated with pharmaceutically-acceptable anions and/or cations. Pharmaceutically-acceptable cations include among others, alkali metal cations (e.g., $Li^+$, $N^{30}$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., Br), sulfate, acetates (e.g., acetate, trifluoroacetate), ascorbates, aspartates, benzoates, citrates, and lactate.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

In some embodiments, a liposome or micelle may be utilized as a carrier or vehicle for the composition. For example, in some embodiments, the diaza compound may be a part of the lipophilic bilayers or micelle, and the targeting ligand, if present, may be on the external surface of the liposome or micelle. As another example, a targeting ligand may be externally attached to the liposome or micelle after formulation for targeting the liposome or micelle (which contains the diaza optical agents) to the desired tissue, organ, or other site in the body.

Every formulation or combination of components described or exemplified herein can be used to practice the invention, unless otherwise stated.

The present compositions, preparations and formulations can be used both as a diagnostic agent as well as a phototherapy agent concomitantly. For example, an effective amount of the present compositions, preparations and formulations in a pharmaceutically acceptable formulation is administered to a patient. Administration is followed by a procedure that combines photodiagnosis and phototherapy. For example, a composition comprising compounds for combined photodiagnosis and phototherapy is administered to a patient and its concentration, localization, or other parameters is determined at the target site of interest. More than one measurement may be taken to determine the location of the target site. The time it takes for the compound to accumulate at the target site depends upon factors such as pharmacokinetics, and may range from about thirty minutes to two days. Once the site is identified, the phototherapeutic part of the procedure may be done either immediately after determining the site or before the agent is cleared from the site. Clearance depends upon factors such as pharmacokinetics.

The present compositions, preparations and formulations can be formulated into diagnostic or therapeutic compositions for enteral, parenteral, topical, aerosol, inhalation, or cutaneous administration. Topical or cutaneous delivery of the compositions, preparations and formulations may also include aerosol formulation, creams, gels, solutions, etc. The present compositions, preparations and formulations are administered in doses effective to achieve the desired diagnostic and/or therapeutic effect. Such doses may vary widely depending upon the particular compositions employed in the composition, the organs or tissues to be examined, the equipment employed in the clinical procedure, the efficacy of the treatment achieved, and the like. These compositions, preparations and formulations contain an effective amount of the composition(s), along with conventional pharmaceutical carriers and excipients appropriate for the type of administration contemplated. These compositions, preparations and formulations may also optionally include stabilizing agents and skin penetration enhancing agents.

Methods of this invention comprise the step of administering an "effective amount" of the present diagnostic and therapeutic compositions, formulations and preparations containing the present compounds, to diagnosis, image, monitor, evaluate, treat, reduce, alleviate, ameliorate or regulate a biological condition and/or disease state in a patient. The term "effective amount," as used herein, refers to the amount of the diagnostic and therapeutic formulation, that, when administered to the individual is effective diagnosis, image, monitor, evaluate, treat, reduce alleviate, ameliorate or regulate a biological condition and/or disease state. As is understood in the art, the effective amount of a given composition or formulation will depend at least in part upon, the mode of administration (e.g. intravenous, oral, topical administration), any carrier or vehicle employed, and the specific individual to whom the formulation is to be administered (age, weight, condition, sex, etc.). The dosage requirements needed to achieve the "effective amount" vary with the particular formulations employed, the route of administration, and clinical objectives. Based on the results obtained in standard pharmacological test procedures, projected daily dosages of active compound can be determined as is understood in the art.

Any suitable form of administration can be employed in connection with the diagnostic and therapeutic formulations of the present invention. The diagnostic and therapeutic formulations of this invention can be administered intravenously, in oral dosage forms, intraperitoneally, subcutaneously, or intramuscularly, all using dosage forms well known to those of ordinary skill in the pharmaceutical arts.

The diagnostic and therapeutic formulations of this invention can be administered alone, but may be administered with a pharmaceutical carrier selected upon the basis of the chosen route of administration and standard pharmaceutical practice.

The diagnostic and therapeutic formulations of this invention and medicaments of this invention may further comprise one or more pharmaceutically acceptable carrier, excipient, buffer, emulsifier, surfactant, electrolyte or diluent. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985).

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of does not exclude materials or steps that do not materially affect the basic and novel characteristics of the claim. In each instance herein any of the terms "comprising", "consisting essentially of and "consisting of may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of treating cancer, a cancer-associated disorder, inflammation or an inflammation -associated disorder, the method comprising: (i) administering to a patient a therapeutically effective amount of a phototherapeutic agent to a target tissue of said patient, the phototherapeutic agent comprising a compound being of the formula (FX38); and (ii) exposing the phototherapeutic agent administered to the patient at the target tissue to electromagnetic radiation having wavelengths selected over the range of 350 nm and 1300 nm sufficient to result in injury or death to cells at the target tissue; wherein

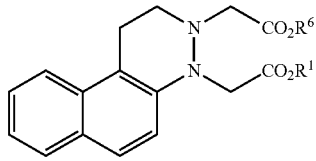

(FX38)

each of $R^1$ and $R^6$ is independently hydrogen, $C_1$-$C_{20}$ alkyl, $C_3$-$C_{20}$ cycloalkyl, $C_5$-$C_{30}$ aryl, $C_5$-$C_{30}$ heteroaryl, $C_1$-$C_{20}$ acyl, $C_2$-$C_{20}$ alkenyl, $C_2$-$C_{20}$ alkynyl, $C_5$-$C_{20}$ alkylaryl, —$(CHOH)_m R^{34}$, —$(CH_2CH_2O)_m R^{35}$, —$CH(R^{36})CO_2H$, or —$CH(R^{37})NH_2$ each of $R^{34}$ and $R^{35}$ is independently hydrogen or $C_1$-$C_{10}$ alkyl;

$R^{37}$ is independently a side chain residue of a natural α-amino acid and m is independently an integer selected from the range of 1 to 100 wherein the exposing cleaves the N—N bond forming two N radicals; and wherein the method is a Type 1 phototherapy procedure.

2. The method of claim 1, wherein at least one of $R^1$ and $R^6$ is a dye that is excited upon exposure to electromagnetic radiation having wavelengths selected over the range of 350 nm to 1300 nanometers; wherein said dye selected from the group consisting of a pyrazine, a thiazole, a phenylxanthene, a phenothiazine, a phenoselenazine, a cyanine, an indocyanine, a squaraine, a dipyrrolo pyrimidone, an anthraquinone, a tetracene, a quinoline, an acridine, an acridone, a phenanthridine, an azo dye, a rhodamine, a phenoxazine, an azulene, an azaazulene, a triphenyl methane dye, an indole, a benzoindole, an indocarbocyanine, a Nile Red dye, or a benzoindocarbocyanine.

3. The method of claim 1, wherein the compound is of the formula FX(36):

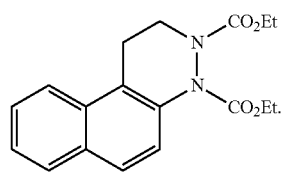

(FX36)

4. The method of claim 1, wherein the target tissue is a colon, prostate, gastric, esophageal, uterine, endometrial, pancreatic, breast, cervical, brain, skin, gallbladder, lung, throat, kidney, testicular, prostate, gastric, or ovary tissue.

5. The method of claim 1, wherein the target tissue is cancerous tissue, or a tumor.

6. The method of claim 1, wherein said electromagnetic radiation has wavelengths selected over the range of 350 nm to about 900 nm.

7. The method of claim 1, wherein $R^1$ and $R^6$ are each t-Bu or H.

\* \* \* \* \*